(12) United States Patent
Zhi et al.

(10) Patent No.: US 6,777,420 B2
(45) Date of Patent: Aug. 17, 2004

(54) HETEROCYCLIC ANTIBACTERIAL COMPOUNDS

(75) Inventors: Chengxin Zhi, Worcester, MA (US); George E. Wright, Worcester, MA (US)

(73) Assignee: Microbiotix, Inc., Worcester, MA (US)

( * ) Notice: Subject to any disclaimer, the term of this patent is extended or adjusted under 35 U.S.C. 154(b) by 0 days.

(21) Appl. No.: 10/173,376

(22) Filed: Jun. 17, 2002

(65) Prior Publication Data

US 2003/0181719 A1 Sep. 25, 2003

Related U.S. Application Data

(60) Provisional application No. 60/349,837, filed on Jan. 17, 2002, provisional application No. 60/348,839, filed on Jan. 14, 2002, and provisional application No. 60/298,534, filed on Jun. 15, 2001.

(51) Int. Cl.$^7$ .................... C07D 239/47; C07D 239/54; A61K 31/506; A61P 31/04
(52) U.S. Cl. ................ 514/272; 514/274; 544/310; 544/312; 544/320; 544/321
(58) Field of Search ........................... 514/254.14, 269, 514/270, 271, 272, 273, 274, 275, 476; 544/295, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 346

(56) References Cited

U.S. PATENT DOCUMENTS

| 4,563,459 A | * | 1/1986 | Grohe et al. ........... 514/253.08 |
| 4,665,079 A | * | 5/1987 | Culbertson et al. ......... 514/312 |
| 5,468,742 A | | 11/1995 | Petersen et al. ............ 514/187 |
| 5,516,905 A | | 5/1996 | Brown et al. ................ 544/312 |

FOREIGN PATENT DOCUMENTS

| EP | 0 132 845 | 2/1985 |
| WO | WO 94/15938 | 7/1994 |
| WO | WO 99/21849 | 5/1999 |
| WO | WO 2003/00665 A1 | * | 3/2003 |
| WO | WO 2001/29010 A1 | * | 4/2003 |

OTHER PUBLICATIONS

Paquette, L.A., "Principles of Modern Heterocyclic Chemistry", Benjamin, New York, 1968, pp. 312–315.*
Andriole, Vincent T. edt., *The Quinolones*, 2nd ed., chapter 2, (Academic Press, San Diego, CA, 1998).
Andriole, Vincent T. edt., *The Quinolones*, 3rd ed., chapter 2, (Academic Press, San Diego, CA, 2000).
Barnes et al., *Nucleic Acids Res.*, 6: 1203–1219 (1979).
Brown et al., *J. Med. Chem.*, 20: 1186–1189 (1977).
Daly et al., *Antimicrob. Agents Chemother.*, 44: 2217–2221 (2000).
Domagala et al., *J. Med. Chem.*, 29: 394–404 (1986).
Domagala et al., *J. Med. Chem.*, 31: 991–1001 (1988).
Egawa et al., *J. Heterocycl. Chem.*, 24(1): 181–185 (1987).
Hamilton–Miller, J. *Antimicrobial Chemotherapy*, 33: 197–202 (1994).
Hammond and Brown, *Protein Exp. Purif.*, 3: 65–70 (1992).
Jendrella et al., *Heterocycles*, 41(6): 1291–1298 (1995).
Jucker and Rissi, *Helv. Chim. Acta.*, 272: 2383 (1962).
Jung et al., *J. Med. Chem.*, 42: 3899–3909 (1999).
Li et al., *Med. Res. Rev.*, 20: 231–293 (2000).
Morden et al., *Am Fam. Physician*, 62: 1870–1876 (2000).
Pfleiderer W., *Chem. Ber.*, 90: 2272 (1957).
Tarantino et al., *Antimicrob. Agents Chemother.*, 43: 1982–1987 (1999).
Tarantino et al., *J. Med. Chem.*, 42, 2035–2040 (1999).
Wright and Gambino, *J. Med. Chem.*, 27: 181–185 (1984).
Wright et al., *Curr. Opin. Anti–Infective Investig. Drugs*, 1: 45–48 (1999).

* cited by examiner

*Primary Examiner*—Richard L. Raymond
*Assistant Examiner*—Thomas McKenzie
(74) *Attorney, Agent, or Firm*—Yankwich & Associates; Thomas R. Berka; Leon R. Yankwich

(57) ABSTRACT

The invention provides heterocyclic organic compounds that inhibit bacterial DNA polymerase IIIC and type II bacterial topoisomerase. The invention further provides compounds that are useful as intermediates in the synthesis of such heterocyclic organic compounds. Syntheses and uses of such heterocyclic organic molecules are also described.

16 Claims, 4 Drawing Sheets

| COMPOUND | R | X | L |
|---|---|---|---|
| 10 | cPr | H | (CH$_2$)$_4$.MeSO$_2$ |
| 4 | Et | H | (CH$_2$)$_4$.MeSO$_2$ |
| 5 | Et | Cl | (CH$_2$)$_4$ |
| 6 | Et | (aza) | (CH$_2$)$_4$ |
| 7 | Et | F | (CH$_2$)$_4$ |
| 8 | cPr | H | (CH$_2$)$_7$ |
| 12 | dFPh | H | (CH$_2$)$_4$ |

HETEROCYCLIC ANTIBACTERIAL COMPOUNDS

CROSS REFERENCE TO RELATED APPLICATIONS

This application claims the benefit under 35 U.S.C. §119 (e) of U.S. provisional application No. 60/298,534, filed Jun. 15, 2001; U.S. provisional application No. 60/348,839, filed Jan. 14, 2002; and U.S. provisional application No. 60/349,837, filed Jan. 17, 2002.

STATEMENT AS TO FEDERALLY SPONSORED RESEARCH

The invention described herein was supported in whole or in part by SBIR grant number 1 R43 GM60828-01 from the National Institutes of Health. The United States Government may have certain rights in the invention.

FIELD OF THE INVENTION

This invention is generally in the field of heterocyclic organic molecules that have antibacterial activity.

BACKGROUND OF THE INVENTION

Bacterial pathogens continue to pose a serious threat to public health as indicated by a worldwide resurgence of bacterial diseases. One aspect of this resurgence appears to be the result of prior widespread, and largely effective, therapeutic and prophylactic use of antibiotics, which, unfortunately, over time has also selected for resistant strains of various bacterial pathogens. Of particular concern to the public health has been the emergence and proliferation of bacterial strains that are resistant to multiple antibiotics in the current arsenal of antimicrobial agents. Such multi-antibiotic resistant ("MAR") bacterial strains include species of Gram positive bacteria, such as, antibiotic resistant strains of *Staphylococcus aureus, Enterococcus fecalis*, and *Enterococcus fecium*, which, along with antibiotic resistant Gram negative strains of *Escherichia coli*, constitute the most frequent etiological agents of nosocomial (hospital-acquired) diseases, such as septicemia, endocarditis, and infections of wounds and the urinary tract. *S. aureus* is currently the most frequent cause of nosocomial bacteremia and skin or wound infection. *Streptococcus pneumoniae* causes several serious and life-threatening diseases, including a contagious meningitis, bacteremia, and otitis media. Annual mortality from *S. pneumoniae* infection alone is estimated at between 3–5 million persons globally. More recently, clinical accounts of highly aggressive skin and tissue infections by "flesh-eating" strains of Group A streptococcus bacteria, such as Streptococcus pyogenes, has heightened the concern and need for new or improved antibacterial agents.

Recently, a group of organic compounds has been described which are structural analogs of deoxynucleotides, such as $N^3$-substituted uracil and isocytosine and 9-substituted guanine and adenine compounds. Such compounds have been classified as "HPUra" (for "6-(p-hydroxyphenylazo)uracil)-like class of anti-microbial compounds or the 6-anilinouracil ("AU") family of compounds, which are non-traditional antibiotics in that they specifically bind and inhibit the bacterial DNA polymerase IIIC ("Pol IIIC") that is required for DNA replication in the "low G-C" eubacteria, which include mycoplasmas and the low G-C, Gram positive bacteria such as Streptococcus, Enterococcus, Staphylococcus, Bacillus, Clostridium, and Listeria (see, e.g., Wright et al., *Curr. Opin. Anti-Infective Investig. Drugs,* 1: 45–48 (1999); Tarantino et al., *J. Med. Chem.,* 42: 2035–2040 (1999); U.S. Pat. No. 5,516,905). Accordingly, these compounds are antibiotics capable of inhibiting Gram positive bacteria and mycoplasmas (see, e.g., U.S. Pat. No. 5,516,905).

Another approach to developing improved antibiotics has been the synthesis of hybrid molecules, such as the family of hybrid molecules consisting of a fluoroquinolone antibiotic molecule (see, e.g., Domagala et al., *J. Med. Chem.,* 29: 394–404 (1986)) linked to a β-lactam antibiotic molecule (see, e.g., Hamilton-Miller, *J. Antimicrobial Chemotherapy,* 33: 197–202 (1994)). Such hybrid molecules are "dual-action" antibiotics in that they offer the benefit of a fluoroquinolone component, which can inhibit bacterial type II topoisomerase (Topo II), and a β-lactam component, such as cephalosporins and penicillins, which inhibit bacterial cell wall synthesis (see, e.g, Hamilton-Miller, *J. Antimicrobial Chemotherapy,* 33: 197–202 (1994)). The fluoroquinolone and β-lactam components may be linked to one another via an ester linkage in a "pro-drug" form, which can undergo hydrolysis after administration to an individual (often catalyzed by esterase) to provide the two active component antibiotics. Alternatively, linkages less susceptible to spontaneous hydrolysis may be used to enhance the half-life of the hybrid molecule after administration. In this latter case, the fluoroquinolone active segment may be released in the presence of a β-lactamase, such as produced by P-lactam resistant bacteria, or when the β-lactam antibiotic is acylated during its mode of action (Id.).

A dual-action antibiotic directed against two different targets in a bacterial cell is an attractive strategy as the probability of the appearance of a resistant strain in a treated bacterial population should be quite low, i.e., equal to the product of the probabilities of occurrence of two, spontaneous and separate, resistant mutations in a single bacterial cell. The impact that currently available, hybrid antibiotics, such as the "cephaloquins" (or "quinocephs"), as described above, will have clinically remains to be determined. Moreover, as is well known, the search and development of a variety of antibiotics will continue to be necessary as it is unlikely that any one class of antibiotics will be effective against a sufficiently wide spectrum of bacteria as to treat all bacterial diseases or to be used in all patients. Thus, in addition to having an antimicrobial action against one or more clinically significant strains of bacterial pathogens, the successful development of any new and useful antibiotic depends not only on the frequency with which resistant strains may arise, but also on an understanding of such pharmaceutically and pharmacologically relevant properties as solubility, potency, patient toxicity, and the susceptibility of the antibiotic to degradation or clearance when administered to a patient by a particular route.

Clearly, needs remain for compounds that can serve as antibiotics against pathogenic bacterial species as well as for compounds that provide the structural foundation for developing future generations of new anti-microbial agents.

SUMMARY OF THE INVENTION

The invention provides a new family of molecules, which are heterocyclic compounds that have antibacterial activity against pathogenic bacterial strains and/or that provide a structural foundation (i.e., are parent molecules) for developing additional new antibacterial agents.

In one embodiment, the invention provides a compound having the formula:

P-L-T, wherein P is a segment of the compound that selectively binds and inhibits bacterial DNA polymerase IIIC in the presence of a DNA template and that is linked, directly or indirectly, to segment T of the compound; L is absent or is a linker segment of the compound comprising 1 to 10 atoms in contiguous linear connectivity that links the P and T segments; and T is a segment that is linked, directly or indirectly, to segment P and that selectively inhibits a type II bacterial topoisomerase; and wherein the compound binds and inhibits polymerase IIIC and type II bacterial topoisomerase; and pharmaceutically acceptable salts, esters, and hydrates thereof.

In another embodiment, the invention provides a compound having formula (1) or (2):

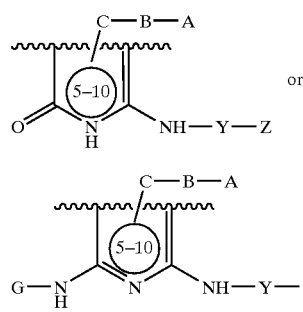

wherein the notation signifies an optionally substituted 5–10 membered mono or bicyclic heterocycle in which the ring members are, independently, selected from the group consisting of carbon, nitrogen, sulfur, and oxygen, and wherein any carbon may be optionally substituted with a lower alkyl, amino, carbonyl and thiocarbonyl; and wherein:

A–B is a segment characterized by an ability to selectively bind bacterial type II topoisomerase;

C is absent or a linker segment comprising 1–10 atoms in contiguous linear connectivity;

G is selected from the group consisting of H, aryl, arylalkyl, alkyl, acyl, and an amino protecting group;

Y is absent or selected from the group consisting of lower alkylidene, NH, and CO;

Z is aryl, which may be optionally substituted with alkyl, halo, amino, nitro, acyl, alkylamino, alkylaminoalkyl, alkoxy, alkoxyalkyl, alkylthio, alkylthioalkyl, oxo, nitro, hydroxyl, cyano, carbocyclyl, carbocyclylalkyl, carbocyclyloxy, carbocyclyloxyalkyl, carbocyclylamino, carbocyclylaminoalkyl, heterocyclyl, heterocyclylalkyl, heterocyclyloxy, heterocycloyloxyalkyl, heterocyclylamino, and heterocyclylaminoalkyl; and wherein the segment defined by A–B–C– may be attached at any position of the 5–10 membered mono or bicyclic heterocycle;

and pharmaceutically acceptable salts, esters and hydrates thereof.

In still another embodiment, the invention provides a compound having a formula selected from the group consisting of formulas (3), (4), (5), (6), (7), and (8), as indicated below:

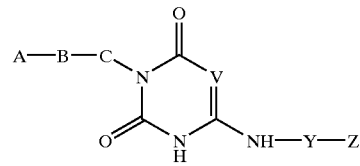

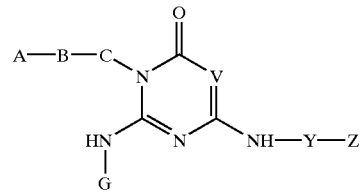

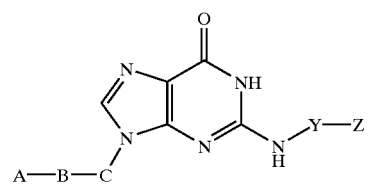

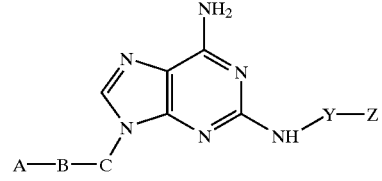

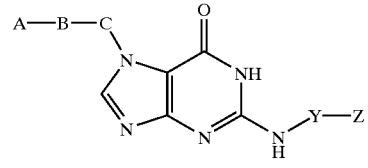

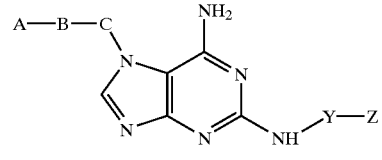

wherein:
the segment A–B is a pyridone;
C is absent or a linker segment comprising 1–10 atoms in contiguous linear connectivity;
G is selected from the group consisting of H, aryl, arylalkyl, alkyl, acyl, and an amino protecting group;
V is N or a ring carbon substituted with substituent W, wherein W is selected from the group consisting of H, lower alkyl, and halo;
Y is absent or selected from the group consisting of lower alkylidene, NH, and CO;
Z is aryl, which may be optionally substituted with a substituent selected from the group consisting of alkyl, halo, amino, nitro, acyl, alkylamino, alkylaminoalkyl, alkoxy, alkoxyalkyl, alkylthio, alkylthioalkyl, oxo, nitro, hydroxyl, cyano, carbocyclyl, carbocyclylalkyl, carbocyclyloxy, carbocyclyloxyalkyl, carbocyclylamino, carbocyclylaminoalkyl, heterocyclyl, heterocyclylalkyl, heterocyclyloxy, heterocycloyloxyalkyl, heterocyclylamino, and heterocyclylaminoalkyl; and pharmaceutically acceptable salts, esters and hydrates thereof.

In another embodiment, the invention provides a compound of any one of formulas (1)–(8), above, wherein the segment A–B is a pyridone, wherein the pyridone is selected from the group consisting of a 4-quinolone-3-carboxylic acid, 4-pyridone-3-carboxylic acid, 8-aza-4-quinolone-3-carboxylic acid, 6-aza-4-quinolone-3-carboxylic acid, 6,8-diaza-4-quinolone-3-carboxylic acid, 4-quinazolin one-3-carboxylic acid and esters thereof. The pyridone may be, e.g., a quinolone. The quinolone may be, e.g., a 6-fluoroquinolone.

The invention also comprises a compound of any one of formulas (1)–(8), wherein the segment A–B- is any one of the radicals of formulas (9), (10), and (11), be low (numbers within rings indicate numbering convention employed):

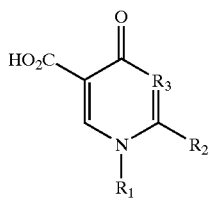

(9)

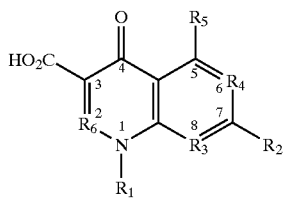

(10)

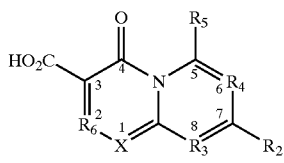

(11)

wherein
X is N or a ring carbon substituted with substituent $R_1$, wherein $R_1$ is selected from the group consisting of optionally substituted alkyl, alkenyl, alkynyl, cycloalkyl, and aryl;

$R_2$ is selected from the group consisting of optionally substituted alkyl, alkenyl, alkynyl, cycloalkyl, alkylcycloalkyl, halo, hydroxyl, and saturated or unsaturated 4–10 membered mono or bicyclic heterocyclyl containing 1, 2, or 3 heteroatoms selected from S, N, and O, that may be optionally substituted with one or more alkyl, alkenyl, alkynyl, amino, alkylamino, aminoalkyl, alkylaminoalkyl, or naturally occurring amino acid residues;

$R_3$ is N or a ring carbon substituted with substituent $R_8$, wherein $R_8$ is selected from the group consisting of H, optionally substituted aryl (e.g., unsubstituted or substituted with halo (e.g., F)) alkyl (e.g., unsubstituted or substituted with halo), alkenyl, alkynyl, alkoxy, amino, alkylamino, cyano, nitro or halo (e.g., F); or $R_1$ and $R_8$ may be joined to form an optionally substituted, fused 4–8 membered heterocyclic or carbocyclic ring (which may be saturated or unsaturated, or aromatic), wherein the heterocyclic ring comprises 1–3 heteroatoms selected from the group consisting of S, N and O;

$R_4$ is N or a ring carbon substituted with substituent $R_9$, wherein $R_9$ is selected from the group consisting of H, optionally substituted aryl (e.g., unsubstituted or substituted with halo (e.g., F)) alkyl (e.g., unsubstituted or substituted with halo), alkenyl, alkynyl, alkoxy, amino, alkylamino, cyano, nitro or halo (e.g., F); or $R_2$ and $R_9$ may be joined to form an optionally substituted, fused 4–8 membered heterocyclic or carbocyclic ring (which may be saturated or unsaturated, or aromatic), wherein the heterocyclic ring comprises 1–3 heteroatoms selected from the group consisting of S, N and O;

$R_5$ is selected from the group consisting of H, halo, amino (e.g., $NH_2$), alkylamino and lower alkyl (e.g., methyl); and $R_6$ is N or a ring carbon substituted with substituent $R_7$, wherein $R_7$ is selected from the group consisting of H, halo and lower alkyl; or $R_1$ and $R_7$ may be joined to form an optionally substituted 4–8 membered heterocycle comprising 1–3 heteroatoms selected from the group consisting of S, N, and O.

In one embodiment, compounds of this invention are useful as antibacterial agents. Such compounds inhibit at least bacterial DNA polymerase IIIC ("Pol IIIC"). The compounds of the invention may have a level of inhibitory activity toward bacterial DNA polymerase IIIC that is greater than the level of inhibitory activity of previously known Pol IIIC inhibitor compounds.

In another embodiment, the compounds of this invention inhibit bacterial type II topoisomerase ("Topo II"). Compounds of the invention inhibit both Pol IIIC and Topo II. In another embodiment, compounds of the invention are antibiotics that are effective against one or more species of bacteria, such as species of Gram positive, mycoplasma, and/or Gram negative bacteria. Compounds of the invention are antibiotics that may be effective against one or more species of Gram positive bacteria, such as, without limitation, species of Streptococcus, Enterococcus, Staphylococcus, Bacillus, Clostridium, Listeria, and combinations thereof.

The invention also provides pharmaceutical compositions comprising a compound of the invention and a pharmaceutically acceptable carrier. Such pharmaceutical compositions may contain one or more other therapeutically active compounds, such as, another antibiotic, anti-viral compound, anti-cancer compound, and the like.

The invention also provides methods of treating bacterial diseases in a patient. Such methods comprise administering a compound of the invention to a patient in need of treatment thereof. The bacterial disease may be caused by a species of mycoplasma or a Gram positive bacteria, including, without limitation, species of Streptococcus, Enterococcus, Staphylococcus, Bacillus, Clostridium, and Listeria.

The invention also provides methods for prophylactic treatment of a bacterial disease comprising administering a compound of the invention to a patient. Such methods are useful when an exact diagnosis cannot or has not been made.

Compounds of the invention may also be used in screening procedures to determine the antibiotic resistance profile of bacterial species of interest.

BRIEF DESCRIPTION OF THE DRAWINGS

FIG. 1A is a diagram of the structural formula for Compound 2 (i.e., 3-{4-[1-(1-cyclopropyl-3-carboxy-4-oxo-6-fluoro-7-quinolyl)-4-piperazinyl]butyl}-6-(3-ethyl-4-methylanilino)uracil).

FIG. 1B is a bar graph showing number of survivors in each group of five mice at 24 hours after intraperitoneal infection with $1\times10^8$ colony forming units (CFU) of Staphylococcus aureus (Smith strain) and followed 15 minutes post infection by administration of Compound 2 at a dose of 0 (Vehicle Control), 1, 3, and 10 mg of compound per kg of body weight. Vancomycin at a dose of 10 mg/kg of body weight served as a positive control for antibiotic activity. See text for details.

FIG. 2A is a diagram of the structural formula for Compound 10 (i.e., 3-{4-[1-(1-cyclopropyl-3-carboxy-4-oxo-6-fluoro-7-quinolyl)-4-piperazinyl]butyl}-6-(3-ethyl-4-methylanilino)uracil methanesulfonate).

FIG. 2B is a bar graph showing number of survivors of a group of five mice at 24 hours after intraperitoneal infection with *Staphylococcus aureus* (Smith strain) as in FIG. 1B, except that Compound 10 was administered to each animal at 0, 0.1, 0.3, 1.0, 3.0, and 10 mg/kg body weight at 15 minutes post infection. Controls were the same as in FIG. 1B. See text for details.

FIG. 3A shows a diagram of a structural formula and table of constituent groups for several representative compounds: Compound 10 is 3-{4-[1-(1-cyclopropyl-3-carboxy-4-oxo-6-fluoro-7-quinolyl)-4-piperazinyl]butyl}-6-(3-ethyl-4-methylanilino)uracil methanesulfonate); Compound 4 is 3-{4-[1-(1-ethyl-3-carboxy-4-oxo-6-fluoro-7-quinolyl)-4-piperazinyl]butyl}-6-(3-ethyl-4-methylanilino)uracil methanesulfonate; Compound 5 is 3-{4-[1-(1-ethyl-3-carboxy-4-oxo-6-fluoro-8-chloro-7-quinolyl)-4-piperazinyl]butyl}-6-(3-ethyl-4-methylanilino)uracil; Compound 6 is 3-{4-[1-(1-ethyl-3-carboxy-4-oxo-6-fluoro-8-aza-7-quinolyl)-4-piperazinyl]butyl}-6-(3-ethyl-4-methylanilino)uracil; Compound 7 is 3-{4-[1-(1-ethyl-3-carboxy-4-oxo-6,8-difluoro-7-quinolyl)-4-piperazinyl]butyl}-6-(3-ethyl-4-methylanilino)uracil; Compound 8 is 3-{7-[1-(1-cyclopropyl-3-carboxy-4-oxo-6-fluoro-7-quinolyl)-4-piperazinyl]heptyl}-6-(3-ethyl-4-methylanilino)uracil; Compound 12 is 3-{4-[1-(1-{2,4-difluorophenyl}-3-carboxy-4-oxo-6-fluoro-7-quinolyl)-4-piperazinyl]butyl}-6-(3-ethyl-4-methylanilino)uracil. Abbreviations: cPr is cyclopropyl; Et is ethyl; dFPh is 2,4-difluorophenyl.

FIG. 3B is a bar graph showing number of survivors in each group of five mice at 24 hours after intraperitoneal infection with *Staphylococcus aureus* (Smith strain) as in FIG. 1, except that 15 minutes after infection, the mice in each group received a dose of 0.5 mg/kg of body weight of compound 10, 4, 5, 6, 7, 8, or 12. Controls were the same as in FIG. 1. See text for details.

DETAILED DESCRIPTION

Figure 1A:
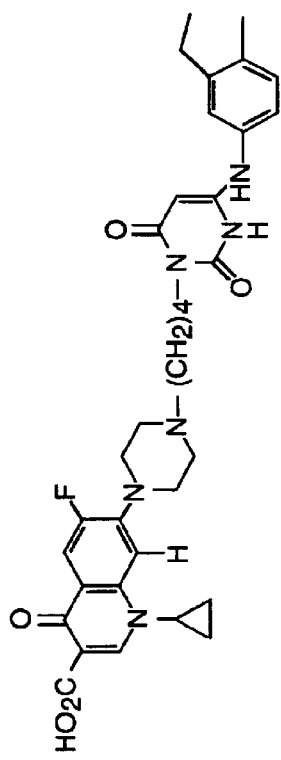
FIGS. 1A and 1B.

In order that the invention may be more clearly understood, the following abbreviations and terms are used as defined below.

Abbreviations for various substituents or side groups of organic molecules are those commonly used in the art. Such abbreviations include "shorthand" forms of such substituents. For example, "Ac" is an abbreviation for an acetyl group and "halo" indicates a halogen. "Me" and "Et" are abbreviations used to indicate methyl ($CH_3$—) and ethyl ($CH_3CH_2$—) groups, respectively, and "MeO" and "EtO" indicate methoxy ($CH_3O$—) and ethoxy ($CH_3CH_2O$—), respectively. Hydrogen atoms are not always shown in organic molecule structures or may be only selectively shown in some structures, as the presence and location of hydrogen atoms in organic molecule structures are assumed to be understood and known by persons skilled in the art. Likewise, carbon atoms are not always specifically abbreviated with "C", as the presence and location of carbon atom, e.g., between or at the end of bonds, in structural diagrams are expected to be known and understood by persons skilled in the art. Amino acids may be indicated herein using conventional three or single letter abbreviations, with or without an indication of the L- or D-steroisomerism. For example, "Ala", "ala", "L-ala", and "A" are all acceptable abbreviations for L-alanine, one of the 20 naturally occurring L-amino acids (see, e.g., Stryker, *Biochemistry Second Edition* (W. H. Freeman and Co., San Francisco, 1981) pp. 13–16).

The term "acyl" means the radical C(O)R, wherein R is selected from alkyl, aryl, alkylaryl, arylakyl (such as benzyl), alkylarylalkyl, heterocyclyl, heterocyclylalkyl, carbocyclyl, carbocyclylalkyl, alkoxyalkyl (such as methoxymethyl), alkoxyalkyl, aryloxyalkyl (such as phenoxymethyl), poly(alkyloxy)alkyl (such as polyethers like poly (methoxy)methyl), aryl (such as phenyl optionally substituted with halo, lower alkyl or lower alkoxy), arylalkyl, and alkylaryl. Specific examples of acyl segments include, without limitation, acetyl, propionyl, butyryl, pentanoyl, 3-methylbutyryl, hydrogen succinyl, 3-chlorobenzoyl, benzoyl, pivalyl, mesyl, propionyl, valeryl, caproic, capryl, lauryl, myristyl, palmityl, stearyl and oleyl.

The term "alkyl" means a saturated straight chain or branched, primary, secondary, or tertiary hydrocarbon radical, typically $C_1$–$C_{18}$, e.g., $C_1$–$C_{10}$ or $C_1$–$C_6$ including, without limitation, methyl, ethyl, propyl, butyl, pentyl, hexyl, isopropyl, isobutyl, sec-butyl, t-butyl, isopentyl, amyl, and t-pentyl. For the purposes of this invention, any carbon in the alkyl segment may be substituted with oxygen (O), sulfur (S), or nitrogen (N). Further, alkyl segments may optionally be substituted with one or more conventionally used alkyl substituents, such as amino, alkylamino, alkoxy, alkylthio, oxo, halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, heterocyclylthio, and the like.

The term "alkylamino" means an amino segment substituted with one or two alkyl groups (i.e., includes dialkyl amino radicals) wherein the alkyl groups may be the same or different.

The term "alkylaryl" means an aryl radical substituted with one or more alkyl substituents.

The term "alkenyl" means an alkyl radical having one or more double bonds. Alkenyl groups containing three or more carbon atoms may be straight or branched.

The term "alkynyl" means an alkyl radical having one or more triple bonds. Alkynyl groups containing three or more carbon atoms may be straight or branched.

The term "amino" means a —$NH_2$, —$NHR_{10}$, or —$NR_{10}R_{11}$, wherein $R_{10}$ and $R_{11}$ may be the same or different and represent a conventionally used amino substitutent. $R_{10}$ and $R_{11}$ may be independently selected from the group consisting of optionally substituted alkyl (e.g., lower alkyl), aryl, and alkylarylalkyl.

The term "antibacterial activity" of a compound or composition of the invention (and equivalent terms used herein), means either having a measurable minimum inhibitory concentration (MIC) value in vitro against whole, intact bacteria, or producing a clinically recognizable improvement of the symptoms of a bacterial infection in vivo in a patient in need thereof. MIC may be measured by techniques known to those of skill in the art, e.g., testing a compound for anti-microbial activity against one or more species of bacteria on solid medium (agar plates) supplemented with varying concentrations of the test compound. Compounds described herein are effective against one or more strains or species of Gram positive bacteria, such as Streptococcus, Enterococcus, Staphylococcus, Bacillus, Clostridium, and Listeria; species of mycoplasma bacteria; and combinations thereof. A clinically recognizable improvement of symptoms of a bacterial infection is any medically-recognized improvement in the health of a patient, including, but not limited to, survival or recovery of the patient from the bacterial infection, reduction in fever, tissue or wound healing, decrease in pain, increase in patient physical or mental vigor, increase in patient appetite, restoration of normal heartbeat, restoration of normal breathing, restoration of normal levels of white blood cells in blood, decrease in titer of antibodies to bacterial antigens in blood or other tissues, and reduction in titer of pathogenic bacteria in biological samples obtained from the patient.

The term "aryl" means a 5–8 membered monocyclic aromatic ring or a polycyclic aromatic ring or ring system having 5–8 ring members in each ring thereof, which may be carbocyclic or heterocyclic and may be unsubstituted or substituted with one or more substituents selected from, but not limited to, alkyl (e.g., lower alkyl), hydroxy, alkoxy (e.g., lower alkoxy), alkylthio, cyano, halo, amino, and nitro. Such aryl radicals may be linked to the remaining portion of the molecule through any position on the ring or substituents that results in a stable compound having the desired activity. Examples of aryl groups are phenyl, methylphenyl, dimethylphenyl, aminophenyl, nitrophenyl, hydroxyphenyl, pyrrolyl, thiazolyl, oxazolyl, pyridyl, pyrimidinyl and the like.

The term "arylalkyl" means an alkyl radical substituted with one or more aryl substituents. The number of carbon atoms specified for arylalkyl radicals refers to the alkyl portion of the segment. Examples of arylalkyl segments include benzyl, methylbenzyl, dimethylbenzyl, aminobenzyl, nitrobenzyl, hydroxybenzyl, and the like.

"Bacteria" means any strain or species of prokaryotic cell as found in the classical kingdom Monera (more recently classified as the kingdoms/domains of Bacteria and Archaea). Bacteria includes, without limitation, Gram positive, Gram negative, Gram variable, and mycoplasma prokaryotes. Examples of Gram positive bacteria include, without limitation, bacilli (such as *Bacillus subtilis* and *Bacillus anthracis*), clostridia (such as *Clostridium tetani*), staphylococci (such as *Staphylococcus aureus*), enterococci (such as *Enterococcos fecium* and *Enterococcus fecalis*), and streptococci (such as *Streptococcus pneumoniae*). Examples of Gram negative bacteria include, without limitation, *Escherichia coli, Pseudomonas aeruginosa, Salmonella typhimurium, Salmonella typhi, Shigella dysenteriae*, and *Vibrio cholerae*.

The term "carbocyclyl" means a segment comprising one or more rings, which may be independently saturated, unsaturated, or aromatic and which contain only carbon ring members. "Carbocycl" includes moieties that are unsubstituted or substituted with one or more substituents, e.g., selected from, but not limited to, alkyl (e.g., lower alkyl), hydroxy, alkoxy (e.g., lower alkoxy), alkylthio, cyano, halo, amino, and nitro. Suitable carbocycles for use in the compounds of this invention include (without limitation) phenyl, benzyl, indanyl, indenyl, naphthyl, tetralyl, decalyl, cyclopentyl, cyclopentenyl, cyclohexyl, cyclohexenyl and cycloheptyl. Carbocycles include (without limitation) cycloalkyl, cycloalkenyl and mono- or bicyclic carbocyclic aromatic rings or ring systems containing from three to ten carbon atoms.

The term "contiguous linear connectivity" means connected together so as to form an uninterrupted linear array or series of atoms. For example, a linker of the compounds described herein having a specified number of atoms in contiguous linear connectivity has at least that number of atoms connected together so as to form an uninterrupted chain, but may also have additional atoms that are not so connected (e.g., branches or atoms contained within a ring system).

The term "cycloalkyl" means a mono- or polycyclic alkyl radical.

"DNA polymerase III" or "Pol III" means a bacterial enzyme having the activity of a bacterial DNA polymerase. This class of enzymes includes, but is not limited to, DNA polymerase IIIC ("Pol EIC") of Gram-positive bacteria and DNA polymerase IIIE of Gram-negative bacteria. The compounds described herein are particularly effective at inhibiting DNA polymerase IIIC found in Gram positive bacteria, such as *Bacillus subtilis*, and in mycoplasmas.

"Effective amount" of a compound or a composition according to this invention means an amount which, when administered to a patient in need thereof, produces antibacterial activity.

"Halo" means a halogen radical, i.e., fluoro, chloro, bromo, or iodo.

"Heterocyclyl" means a heterocyclic radical containing one or more rings which may be saturated, unsaturated, or aromatic wherein at least one ring of the radical optionally contains one or more heteroatoms selected from nitrogen (N), oxygen (O), and sulfur (S) in one or more rings. Suitable heterocyclyl for use in the compounds of this invention include radicals of (without limitation) furan, dioxolane, thiophene, pyrrole, pyrazole, triazole, imidazole, pyrrolidine, pyran, pyridine, pyrimidine, morpholine, piperidine, piperazine, oxazole, isoxazole, oxazoline, oxazolidine, oxathiazole, thiazole, isothiazole, thiadiazole, tetrazole, benzofuran, indole, isoindole, quinazoline, quinoline, isoquinoline, purine, pyrrolopyrimidine, pyrazolopyrimidine, pteridine, ketal. In addition, heterocyclyl radicals may contain one or more substituents (i.e., a ring substituent, such as a halogen atom, an alkyl radical, or aryl radical) attached to a ring member atom of the heterocyclyl radical. All stable isomers of heterocyclyl groups are contemplated in this definition.

"Linker" means a diradical having from 1–10 atoms in contiguous linear connectivity (i.e., as defined above and excluding atoms present in any side chains and branches), that covalently connects one segment of a compound of this invention to the remaining portion of the compound. The atoms of the linker in contiguous linear connectivity may be connected by saturated or unsaturated covalent bonds. Linkers are alkylidene, alkenylidene, alkynylidene and cycloalkylidene (e.g., lower alkylidene, cycloalkylidene, alkylycloalkylidene and alkyl-substituted alkylidene) linkers wherein one or more (e.g., between 1 and 4, such as 1 or 2) carbon atoms may be optionally replaced with O, S, or N and wherein two or more (e.g., 2–4, such as 2 or 3) adjacent atoms may be optionally linked together to form a carbocyclic or heterocyclic moiety within the linker (which may be monocyclic, polycyclic and/or fused, and which may be saturated, unsaturated, or aromatic). Examples of linkers useful in the compounds of the invention include (without limitation) diradicals of alkyl, alkenyl, alynyl, alkoxy, alkoxyalkyl, alkylaminoalkyl, cycloalkyl, alkylcycloalkyl, and alkyl-substituted alkylcycloalkyl (wherein one or more carbon atoms in any of these linkers may be optionally replaced with O, S, or N).

"Lower" means the group to which it is applied has 1–6, e.g., 1–4, carbon atoms, except in the case of rings (such as cycloalkyl), in which case "lower" signifies 3–6 ring members. Unless noted to the contrary, substituents to compounds described herein are "lower".

"$N^{\#}$", wherein the superscript # is an integer, when used in connection with ring nomenclature, means that the named substituent (or "ligand") is located on an exocyclic amino nitrogen that is attached to the ring.

"Protecting group" means a chemical group that is known in the art to protect an otherwise reactive segment against undesirable reaction during one or more particular synthetic procedures and that is selectively removable under a given set of reaction conditions. Protecting groups may be suitable for use, for example, where a nucleoside base segment of a compound of the invention contains a free amino or carboxylic acid functionality. Suitable protecting groups for such use are well known to those of ordinary skill in the art and include, without limitation, trimethylsilyl, dimethylhexylsilyl, t-butyldimethylsilyl, t-butyldiphenylsilyl, trityl, alkyl groups, acyl groups (such as acetyl and propionyl), methanesulfonyl, and p-toluenesulfonyl. Protecting groups that are especially useful for protecting amide functionalities include (without limitation): aralkoxymethyl (e.g., benzyloxymethyl and substituted benzyloxymethyl); alkoxymethyl (e.g., methoxymethyl and trimethylsilylethoxymethyl); trialkyl/arylsilyl (e.g., trimethylsilyl, t-butyldimethylsily, t-butyldiphenylsilyl); tri alkyl/arylsilyloxymethyl (e.g., t-butyldimethylsilyloxymethyl, t-butyldiphenylsilyloxymethyl); 4-alkoxyphenyl (e.g., 4-methoxyphenyl); 2,4-di(alkoxy)phenyl (e.g., 2,4-dimethoxyphenyl); 4-alkoxybenzyl (e.g., 4-methoxybenzyl); 2,4-di(alkoxy)benzyl (e.g., 2,4-di(methoxy)benzyl); alk-1-enyl (e.g., allyl, but-1-enyl and substituted vinyl e.g., 2-phenylvinyl); allyloxycarbonyl; and lower alkoxycarbonyl and benzyloxycarbonyl. Examples of suitable protecting groups for carboxyl groups are the residue of an ester-forming aliphatic or araliphatic alcohol or of an ester-forming silanol (the alcohol or silanol, e.g., containing from 1–20 or from 1–10 carbon atoms). Protecting groups that are especially useful for protecting amino functionalities include, without limitation,: acyl groups, including acetyl, trifluoroacetyl, benzoyl; and acyloxy groups, including t-butyloxycarbonyl, benzyloxycarbonyl, fluoroethenylmethoxycarbonyl, and the like. Protecting groups may be removed by standard methods after the contemplated reaction has been completed. For a more complete description of protecting groups and their use see T. W. Greene and P. G. M. Wuts, *Protective Groups in Organic Synthesis,* 2nd ed., John Wiley & Sons, New York, 1991.

"Nucleoside base" and analogs and derivatives thereof means any purine, deazapurine, pyrimidine, or deazapyrimidine nucleoside base (e.g., adenine, guanine, cytosine, uracil, thymine, deazaadenine, deazaguanosine and pyridine) that is found in native nucleosides, or an analog thereof, which mimics such bases in that their chemical structures are similar to the native bases but may either possess additional or lack certain of the functional properties of the native bases. Nucleoside bases and analogs and derivatives thereof suitable for use in this invention will be well known to those skilled in the art. The term "analog" in reference to a nucleoside base includes analogs having one or more synthetic modifications in any suitable position. Such analogs include, without limitation, those derived by replacement of a ring carbon atom by a nitrogen atom (e.g., 5-azapyrimidines such as 5-azacytosine), replacement of a ring nitrogen atom by a carbon atom (e.g., 7-deazapurines such as 7-deazadenosine or 7-deazaguanosine) or both (e.g., 7-deaza-8-azapurines). Other analogs include, without limitation, nucleoside bases having five membered heterocyles containing one or more O, N, or S and combinations thereof in any relative position (such as thiazoles, imidazoles, oxazoles, pyrazoles, triazoles, oxathiazoles, thiadiazoles, and tetrazoles). Examples of suitable nucleoside base analogs include (without limitation) those described generally in Scheit, *Nucleotide Analogs* (John Wiley, New York, 1980). By "derivatives" of such bases or analogs are meant those compounds wherein ring substituents (or "ligands") are either incorporated, removed, or modified by synthetic means using conventional substituents known in the art. Nucleoside base analogs and derivatives thereof include (without limitation) 6-alkyl purines and $N^6$-alkyl 6-aminopurines, $N^6$-acyl 6-amino purines, $N^6$-benzyl 6-amino purines, 6-halo purines, $N^6$-halo 6-amino purines, $N^6$-vinyl 6-amino purines, $N^6$-alkynyl 6-amino purines, $N^6$-acyl 6-amino purines, $N^6$-hydroxyalkyl 6-amino purines, $N^6$-thioalkyl 6-amino purines, $N^2$-alkyl 2-amino purines, $N^4$-alkyl 4-amino pyrimidines, $N^4$-acyl 4-amino pyrimidines, 4-benzyl pyrimidines, $N^4$-ethynyl 4-amino pyrimidines, 4-acyl and $N^4$-acyl 4-amino pyrimidines, 4-hydroxyalkyl pyrimidines, 4-thioalkyl pyrimidines, 6-aza pyrimidines (such as 6-aza cytosine), 2- and 4-mercapto pyrimidines, $C^5$-benzyl pyrimidines, $C^5$-halo pyrimidines, $C^5$-vinyl pyrimidines, $C^5$-ethynyl pyrimidines, $C^5$-acyl pyrimidines, $C^5$-hydroxy and -hydroxyalkyl pyrimidines, $C^5$-amido and -amidoalkyl pyrimidines, $C^5$-cyano pyrimidines, $C^5$-nitro pyrimidines, $C^5$-amino pyrimidines, $N^2$-alkyl-6-thio-2-amino purines, imidazolopyridines, pyrrolopyrimidines and pyrazolopyrimidines. Nucleoside bases and analogs and derivatives thereof include (without limitation) 9- and/or $N^2$-substituted guanine, 9- and/or 2-substituted adenine, 3- and/or 6-substituted uracil, 3- and/or 6-substituted isocytosine. Exemplary nucleoside base analogs and derivatives include but are not limited to 2,6-diamino purine, hypoxanthine, pseudouridine, isocytosine, isoguanine, 2-thiopyrimidine, 5-fluorocytosine, 5-methylcytosine, 6-azapyrimidines (including 6-azacytosine), 5-azacytidine, 5-azauracil, 5-halouracil (including 5-fluorouracil) and triazolopyridine. Nucleoside bases and analogs and derivatives thereof include (without limitation): uracil linked through the 3-position, isocytosine linked through the 3-position, guanine linked through the 7- or 9-position, adenine linked through the 7- or 9-position, 3-deazaguanine linked through the 7- or 9-position, 2-pyridone linked through the 3- or 4-position and 2-aminopyridine linked through the 3 or 4 position.

The choice of appropriate nucleoside bases and analogs and derivatives thereof for use in the compounds described herein should be considered together with "enzyme-specific domains" present in the compounds of this invention. Such "enzyme-specific domains" include (without limitation) appropriately substituted, carbocyclic or heterocyclic, aryl that may be linked through an exocyclic NH group, directly or indirectly through a linker (e.g., linked directly, or through a $C_1$–$C_3$, such as $CH_2$, linker) to the nucleoside base or analog or derivative thereof, such as, uracil substituted with optionally substituted anilino or benzylamino at the 6-position, isocytosine substituted with optionally substituted anilino or benzylamino in the 6-position, guanine substituted with optionally substituted phenyl or benzyl in the $N^2$-position and adenine substituted with optionally substituted anilino or benzylamino in the 2-position. Substituents for the ring portion of the enzyme-specific domains in the compounds of this invention include 3-lower alkyl, lower alkenyl, lower alkynyl or halo and/or 4-lower alkyl, lower alkenyl, lower alkynyl or halo, and substituents in which positions 3 and 4 are linked to form a fused 5 or 6 membered carbocyclic ring which may be saturated, unsaturated or aromatic (such as indanyl, tetrahydronaphthyl, indolyl or naphthyl).

The terms "patient" and "individual" are synonymous, unless noted otherwise, and mean any mammal, including without limitation, a human, who receives or may be a candidate to receive an antibacterial compound described herein. Thus, as used herein, a "patient" may or may not have exhibited a recognizable symptom of a disease, but merely be at risk for infection by a bacterial species that may cause a disease, e.g., due to exposure to a source of infection.

"Pyridone", for the purposes of this invention, means a compound having the chemical structure of a 2-pyridone or a 4-pyridone (including bicyclic structures such as quinolone, naphthyridone, benzoxazalone, pyridopyrimidone, pyrimidopyridone, and quinazolinone any of which may be optionally substituted with conventional substituents for compounds of those types (see substituents discussed and referenced in chapter 2 of *The Quinolones*, 2nd ed., Vincent T. Andriole, ed., 1998, Academic Press (San Diego, Calif.); chapter 2, *The Quinolones*, 3rd ed., Vincent T. Andriole, ed., 2000, Academic Press (San Diego, Calif.); and Q. Li et al., "The 2-Pyridone Antibacterial Agents: Bacterial Topoisomerase Inhibitors", Med Res Rev 2000 Jul, 20(4): 231–293, which are hereby incorporated by reference in their entirety). In the case where a pyridone is designated by the segment A–B in a formula described herein, segment A–B may be a pyridone having the formula 9, 10, or 11, wherein B is substituent $R_2$ and A is the remaining portion of the formula.

In one embodiment of the compounds of this invention, a pyridone has a carboxylic acid functionality positioned ortho to the carbonyl segment. For example, pyridones that are useful in the compounds of this invention include the monocyclic structure:

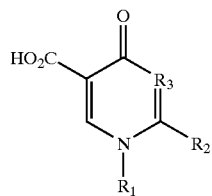

(9)

wherein $R_1$, $R_2$, and $R_3$ are each, independently, selected from conventional 4-pyridone substituents.

Pyridones useful in the compounds of this invention include those having the following structures (numbers in rings indicate numbering convention employed):

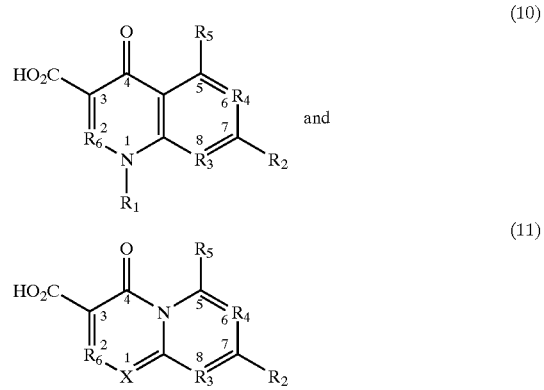

wherein X is N or a ring carbon substituted with substituent R1; wherein $R_1$, $R_2$, $R_3$, $R_4$, $R_5$, and $R_6$ are selected from conventional pyridone substituents.

In another embodiment, a pyridone useful in the compounds of this invention has one of the structures shown above, wherein:

X is N or a ring carbon substituted with substituent $R_1$;

$R_1$ is selected from the group consisting of an optionally substituted alkyl (optionally substituted lower alkyl, such as ethyl and fluoro-ethyl), alkenyl, alkynyl, cycloalkyl (e.g., cyclopropyl), and aryl (e.g., phenyl, halophenyl, and 4-fluorophenyl or 2,4-difluorophenyl); and $R_2$ is selected from the group consisting of optionally substituted alkyl, alkenyl, alkynyl, cycloalkyl, alkylcycloalkyl, halo, hydroxyl, and saturated or unsaturated 4–10 membered mono or bicylic heterocyclyl containing 1, 2 or 3 heteroatoms selected from S, N and O (e.g., one or two N) that may be optionally substituted with one or more alkyl, alkenyl, alkynyl, amino, alkylamino, aminoalkyl, alkylaminoalkyl, or naturally occurring amino acid residues;

$R_3$ is N or a ring carbon substituted with substituent $R_8$, wherein $R_8$ is selected from the group consisting of H, optionally substituted, aryl, unsubstituted or substituted with halo (e.g., F)), alkyl (unsubstituted or substituted with halo), alkenyl, alkynyl, alkoxy, amino, alkylamino, cyano, nitro or halo (F), or wherein $R_1$ and $R_8$ are joined to form an optionally substituted, fused 4–8 membered heterocyclic or carbocyclic ring (which may be saturated or unsaturated, or aromatic), wherein the heterocyclic ring comprises 1–3 heteroatoms selected from the group consisting of S, N and O;

$R_4$ is N or a ring carbon substituted with substituent $R_9$; wherein $R_9$ is selected from the group consisting of H, optionally substituted aryl (e.g., unsubstituted or substituted with halo, e.g., F) alky (e.g., unsubstituted or substituted with halo), alkenyl, alkynyl, alkoxy, amino, alkylamino, cyano, nitro or halo (e.g., F), or wherein $R_2$ and $R_9$ are joined to form an optionally substituted, fused 4–8 membered heterocyclic or carbocyclic ring (which may be saturated, unsaturated, or aromatic), wherein the heterocyclic ring comprises 1–3 heteroatoms selected from the group consisting of S, N and O;

$R_5$ is selected from the group consisting of H, halo, amino (e.g., $NH_2$) alkylamino and lower alkyl (e.g., methyl); and $R_6$ is N or a ring carbon substituted with substituent $R_7$, wherein $R_7$ is selected from the group consisting of H, halo and lower alkyl; or $R_1$ and $R_7$ may be joined to form an optionally substituted 4–8 membered heterocycle comprising 1–3 heteroatoms selected from the group consisting of S, N and O.

A pyridone in a compound described herein may be one in which $R_2$ is selected from the group consisting of optionally substituted piperidinyl, pyrrolidinyl and piperazinyl heterocycles optionally fused with a 3–6 membered carbocycle or heterocycle and $R_2$ is selected from the group consisting of:

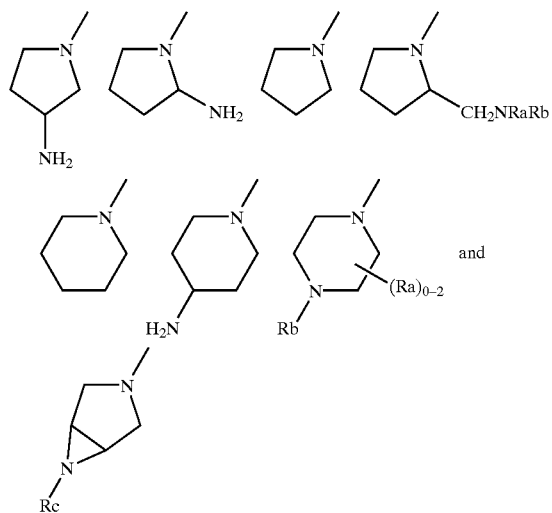

optionally fused with a 3–6 membered carbocycle or heterocycle, and wherein each Ra and Rb is independently selected from the group consisting of H and lower alkyl (e.g., H), and Rc is selected from the group consisting of H, lower alkyl and a chain of 1–6 amino acid residues (e.g., 2–4 amino acid residues, such as, L-alanine, D-alanine, phenylalanine, glycine, lysine, valine, glutamine, and 2–4 L-ala residues).

A pyridone in a compound described herein may be one in which $R_2$ is selected from the group consisting of the following non-limiting examples:

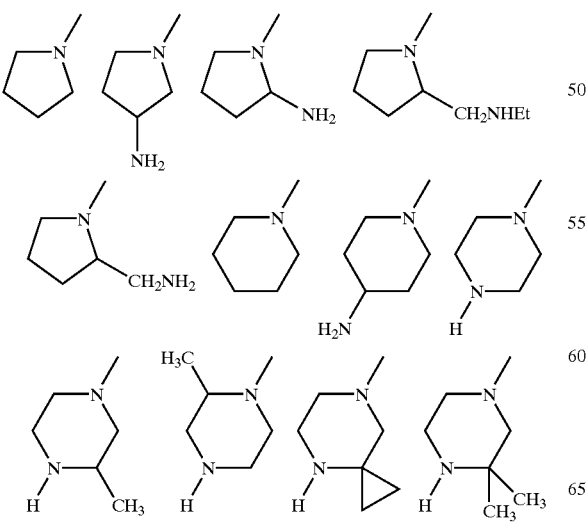

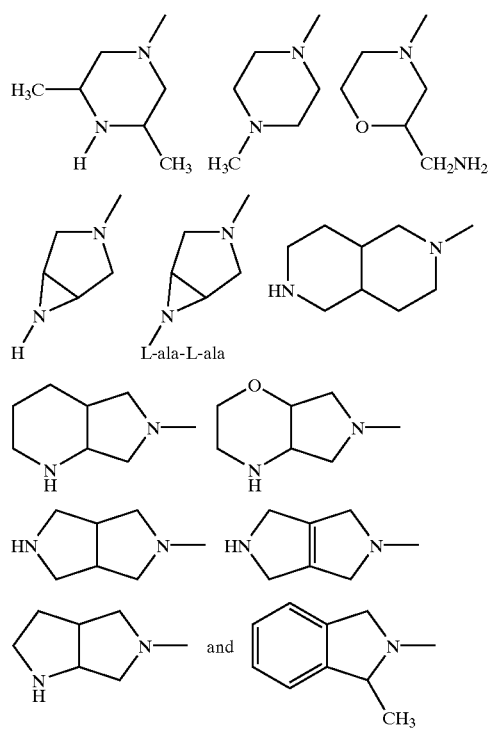

wherein Et is an ethyl radical and L-ala is an L-alanine amino acid residue.

A pyridone segment may be attached to the remainder of a compound of the invention at any position that results in antibacterial activity. In the case where $R_2$ is piperazinyl or a diazabicyclyl ring, the piperazinyl or diazabicyclyl radical may be attached to the remainder of the compound through an endocyclic nitrogen. In the case of piperidinyl and pyrrolidinyl, the remainder of the compound should be linked through an endocyclic carbon atom or via a substituent (such as an amino, alkyl or alkylamino substituent) attached to an endocyclic carbon. Some non-limiting examples of points of attachment for linking examples of $R_2$ to a pyridone moiety and to the remainder of a compound described herein are shown below:

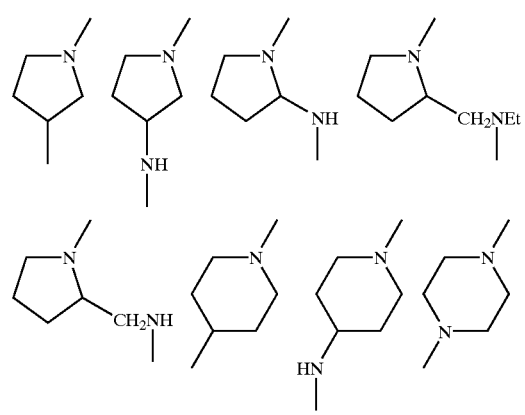

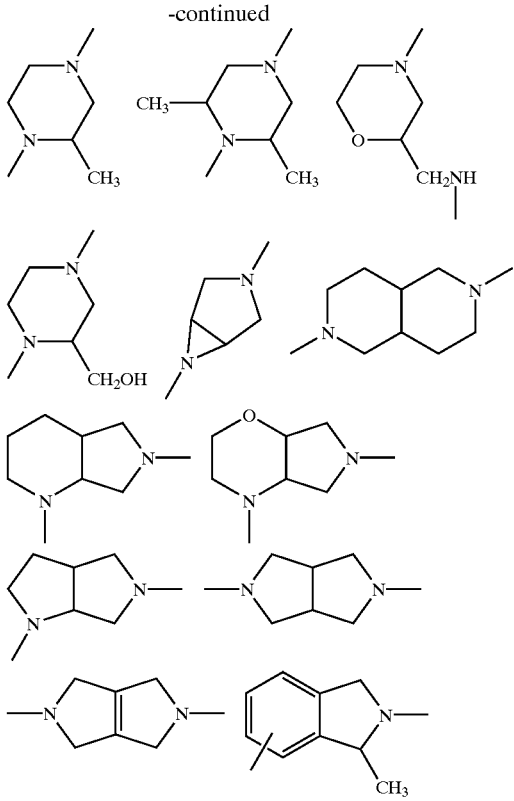

The term "segment" means a portion of a parent compound that, when referred to apart from the parent compound, is capped with H, instead of being linked to the remainder of the parent compound. When referred to as a part of the parent compound, a segment shall be viewed as a radical of that segment. In addition, a "segment" of a compound described herein may also refer to a linked combination or grouping of two or more smaller contiguous segments of the compound. For example, a compound having linked segments A–B–C–D–E, also contains "segments" A–B, A–B–C, and B–C.

"Selectively bind" means the ability of a segment to demonstrate selective affinity for a particular target bacterial protein, as compared to a close human analog thereof. In the case of segments of a particular compound of this invention, the segment will be said to selectively bind to a particular bacterial target protein if, when taken as an individual compound (e.g., having the covalent linkage between the segment and the remaining portion of the compound replaced with H), such segment selectively binds to the target. Such selectivity may be at least a 10-fold, at least a 50-fold difference, or even, at least a 100-fold difference, between the binding constant of that segment for the bacterial protein versus a human analog thereof. Examples of analogous bacterial and human proteins include bacterial DNA polymerase III versus human DNA polymerases (such as α, δ, and ε) and bacterial DNA topoisomerase versus human DNA topoisomerase.

"Substituted", unless otherwise specified herein, means replacing one or more hydrogen radicals in a given structure or segment thereof with substituents (also called "ligands") conventionally used for structures or segments of the same general type. Conventional substituents for the structures and segments described herein may be found in the published literature and will be generally known to those of ordinary skill in the art of chemical synthesis.

"Type II topoisomerase", "Topo II", or an equivalent term means a bacterial enzyme having the activity of a type II bacterial topoisomerase (including both the alpha and beta isoenzymes). These enzymes are characterized by the ability to cleave both strands of a bacterial double-stranded DNA molecule at the same time, passing a portion of the DNA duplex through the cut strands, and resealing the strands. Examples of type II topoisomerases include, without limitation, bacterial DNA gyrase and bacterial topoisomerase IV.

Unless otherwise specified, the terms defined above shall have the meanings ascribed above even when such terms are used as a part (e.g., as a prefix or a suffix) of a different term (e.g., the definition of alkyl given above shall apply to the alkyl portion of an alkylamino group). Specific examples of chemical groups falling within the general categories shown above are for the sake of convenience. It will be understood that these examples are not exhaustive and should not be viewed as limiting the scope of the invention in any way. Any radical defined above as being optionally substituted may be linked directly or indirectly through any of its substituents. Combinations and choices of substituents shall be selected so as to produce stable chemical compounds having the desired antibacterial activity and which are available by conventional synthetic techniques. For any given substituent, stated examples may apply even if that substituent is used in a different combination of variables. In all cases, functional oxygen, nitrogen, sulfur, or other chemically active segments may be protected as necessary or desired using conventional protecting groups. For compounds of this invention having one or more chiral centers, such compounds may be stereochemically pure, for example individual enantiomers or diastereomers, or may be present as a mixture of stereoisomers, such as a racemic or other ratio mixture of individual enantiomers or diastereomers. This choice will be made on a case-by-case basis, taking into account the observed activity of the mixture and of individual stereoisomers.

A compound of the invention includes the corresponding "pharmaceutically acceptable salts of the compound". By the term "pharmaceutically acceptable salts of the compound" as understood and used herein, is meant those salts of any compound of the invention derived from an inorganic or organic acid or base recognized in the art as compatible for pharmaceutical compositions. For convenience, the terms "pharmaceutical" and "pharmaceutically acceptable" also are understood to encompass compounds acceptable for the practice of veterinary medicine as well. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids such as oxalic, while not themselves pharmaceutically acceptable, may be useful as intermediates in obtaining the compounds of the invention and their pharmaceutically acceptable acid addition salts. Salts derived from appropriate bases include alkali metal (e.g., sodium, potassium), alkaline earth metal (e.g., magnesium), ammonium and $NR_4+$ (where R is a $C_{1-4}$ alkyl) salts, and the like. Reference, hereinafter, to a compound according to the invention (or an equivalent term) is understood to include any and all corresponding pharmaceutically acceptable salts thereof.

"Therapy" and "therapeutic" as understood and used herein refer to treatment of a patient for a bacterial infection or disease. For convenience, the terms are also understood to encompass prophylactic or precautionary use or administration of a compound of the invention. Such precautionary or prophylactic use is exemplified by administration of an antibiotic to an immunocompromised or immunodeficient patient; to a patient suspected, but not proven, of having a bacterial infection; or to a patient that is susceptible to contracting a pathogenic bacterial infection or disease (e.g., bacterial meningitis, pneumonia, tuberculosis, septicemia, plague), for example, due to open wounds; contact with water, food, body fluids, corpses, or carcasses containing pathogenic bacteria; or contact with infected individuals or body fluids thereof containing pathogenic bacteria.

The invention provides a new family of molecules, which are heterocyclic compounds that have antibacterial activity against pathogenic bacterial strains and/or that provide a structural foundation (i.e., are parent molecules) for developing additional new antibacterial agents.

In one embodiment, the invention provides a compound having the formula:

P-L-T, wherein P is a segment that selectively binds and inhibits bacterial DNA polymerase IIIC in the presence of a DNA template and that is linked, directly or indirectly, to segment T; L is absent or is a linker segment comprising 1 to 10 atoms in contiguous linear connectivity that links segments P and T; and T is a segment that is linked, directly or indirectly, to P and that selectively inhibits a type II bacterial topoisomerase ("Topo II"); and wherein the compound inhibits both polymerase IIIC and type II bacterial topoisomerase; and pharmaceutically acceptable salts, esters, and hydrates thereof.

In another embodiment, the invention provides a compound having the formula P-L-T, as described above, wherein the compound has antibacterial activity.

Compounds of the invention include compounds having the formula P-L-T, as described above, wherein segment P comprises a nucleoside base or analog or derivative thereof. Segment P may comprise a nitrogenous, heterocyclic base selected from the group consisting of uracil linked through the 3-position; isocytosine linked through the 3-position; guanine linked through the 7-, 8- or 9-position; adenine linked through the 7-, 8- or 9-position; 3-deazaguanine linked through the 7-, 8- or 9-position; 2-pyridone linked through the 3- or 4-position and 2-aminopyridine linked through the 3- or 4-position.

In another embodiment, the invention provides a compound having the formula P-L-T, as described above, wherein P comprises a nitrogenous, heterocyclic base selected from the group consisting of uracil substituted with optionally substituted phenylamino or benzylamino at the 6-position; isocytosine substituted with optionally substituted phenylamino or benzylamino in the 6-position; guanine substituted with optionally substituted phenyl or benzyl on the $N^2$-position; adenine substituted with optionally substituted phenylamino or benzylamino in the 2-position; and 2-aminopyridine linked through the 3 or 4 position. The optionally substituted phenylamino, phenyl, benzylamino, or benzyl may be substituted in the 3-position by lower alkyl, lower alkenyl, lower alkynyl or halo and/or substituted in the 4-position by lower alkyl, lower alkenyl, lower alkynyl or halo, or positions 3 and 4 are linked to form a fused 5 or 6 membered carbocyclic ring which may be saturated, unsaturated or aromatic.

In another embodiment, the invention provides a compound having formula (1) or (2):

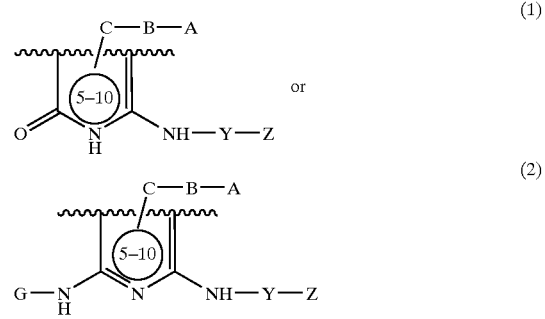

wherein the notation

signifies an optionally substituted 5–10 membered mono or bicyclic heterocycle in which the ring members are, independently, selected from the group consisting of carbon, nitrogen, sulfur, and oxygen, and wherein any carbon may be optionally substituted with a lower alkyl, amino, carbonyl and thiocarbonyl; and wherein:

A–B is a segment characterized by an ability to selectively bind bacterial type II topoisomerase;

C is absent or a linker segment comprising 1–10 atoms in contiguous linear connectivity;

G is selected from the group consisting of H, aryl, arylalkyl, alkyl, acyl, and an amino protecting group;

Y is absent or selected from the group consisting of lower alkylidene, NH, and CO;

Z is aryl, which may be optionally substituted with alkyl, halo, amino, nitro, acyl, alkylamino, alkylaminoalkyl, alkoxy, alkoxyalkyl, alkylthio, alkylthioalkyl, oxo, nitro, hydroxyl, cyano, carbocyclyl, carbocyclylalkyl, carbocyclyloxy, carbocyclyloxyalkyl, carbocyclylamino, carbocyclylaminoalkyl, heterocyclyl, heterocyclylalkyl, heterocyclyloxy, heterocycloyloxyalkyl, heterocyclylamino, and heterocyclylaminoalkyl; and wherein the segment A–B–C- may be attached at any position of the 5–10 membered mono or bicyclic heterocycle; and pharmaceutically acceptable salts, esters and hydrates thereof.

In another embodiment, the invention provides a compound having a formula selected from the group consisting of formulas (3), (4), (5), (6), (7), and (8), as indicated below:

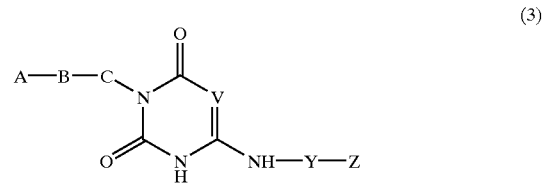

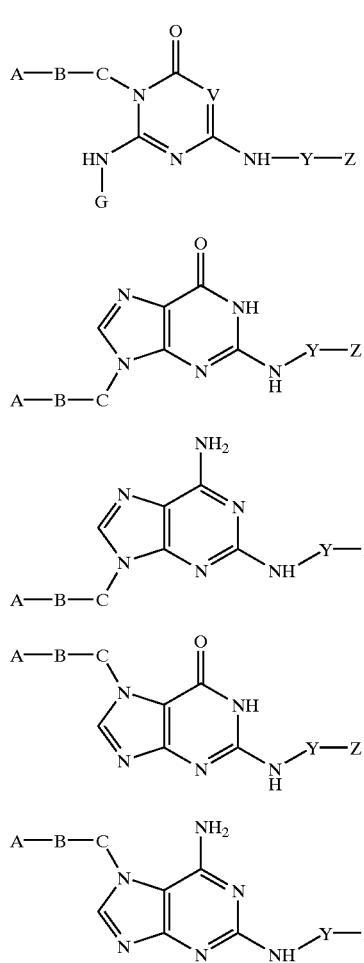

wherein:
the segment A–B is a pyridone;
C is absent or is a linker segment comprising 1–10 atoms in contiguous linear connectivity;
G is selected from the group consisting of alkyl, acyl, and an amino protecting group;
V is N or a ring carbon substituted with substituent W, wherein W is selected from the group consisting of H, lower alkyl, and halo;
Y is absent or selected from the group consisting of lower alkylidene, NH, or CO;
Z is aryl, which may be optionally substituted with alkyl, halo, amino, nitro, acyl, alkylamino, alkylaminoalkyl, alkoxy, alkoxyalkyl, alkylthio, alkylthioalkyl, oxo, nitro, hydroxyl, cyano, carbocyclyl, carbocyclylalkyl, carbocyclyloxy, carbocyclyloxyalkyl, carbocyclylamino, carbocyclylaminoalkyl, heterocyclyl, heterocyclylalkyl, heterocyclyloxy, heterocycloyloxyalkyl, heterocyclylamino, and heterocyclylaminoalkyl; and
wherein the segment defined by A–B–C– may be attached at any position of the 5–10 membered mono or bicyclic heterocycle;
and pharmaceutically acceptable salts, esters and hydrates thereof.

The invention also provides a compound of any one of formulas (1)–(8), as described above, wherein:
Y is absent or CH$_2$; and Z is phenyl optionally substituted with 1–3 substituents independently selected from aryl, lower alkyl, lower alkenyl, lower alkynyl, lower alkoxy, lower alkyloxyalkyl, lower arylalkyl, halo, hydroxy, nitro and amino, or two adjacent positions may be linked to form a fused 4, 5 or 6 membered carbocyclic ring, which may be saturated, unsaturated or aromatic. In another embodiment, Z is phenyl substituted with 1 or 2 substituents independently selected from the group consisting of lower alkyl, lower alkenyl, lower alknyl, halo, hydroxy, and amino; or two adjacent positions may be linked to form a fused 4, 5, or 6 membered carbocyclic ring, which may be saturated, unsaturated, or aromatic. Z may also be a phenyl substituted in the 3- and 4-position with substituents independently selected from the group consisting of aryl, lower alkyl, lower alkenyl, lower alkynyl, lower alkoxy, lower alkyloxyalkyl, lower arylalkyl, halo, hydroxy, and amino. In yet another embodiment, compounds are provideed in which Z is phenyl substituted in the 3- and 4-position with independently selected lower alkyl substituents, such as wherein Z is 3-ethyl, 4-methyl phenyl.

In another embodiment, a compound of the invention has formula (3) or (4), above, wherein Y is CH$_2$ and Z is phenyl substituted with 1 or 2 substituents independently selected from lower alkyl, lower alkenyl, lower alknyl, halo, hydroxy and amino, or wherein two adjacent positions may be linked to form a fused 4, 5, or 6 membered carbocyclic ring which may be saturated, unsaturated, or aromatic. For example, this group includes compounds of formulas (3) and (4), wherein Z is 3-methyl, 4-ethyl phenyl.

Compounds of the invention also include compounds having formulas (1)–(8), wherein A–B comprises a pyridone, e.g., wherein the pyridone is a quinolone. Examples of pyridones useful in the compounds described herein include the group consisting of 4-quinolone-3-carboxylic acid; 4-pyridone-3-carboxylic acid; 8-aza-4-quinolone-3-carboxylic acid; 6-aza-4-quinolone-3-carboxylic acid; 6,8-diaza-4-quinolone-3-carboxylic acid; 4-quinazolinone-3-carboxylic acid; halo substituted forms of any of the preceding pyridones; and esters of any of the preceding pyridones. In another embodiment, compounds of the invention are provided in which A–B is a quinolone that inhibits bacterial Topo II, such as a fluoroquinolone that inhibits bacterial Topo II.

Compounds useful in the compositions and methods of the invention are provided that have any one of formulas (1)–(8), comprise the segment A–B, which is a radical having any one of pyridone formulas (9), (10), or (11), as indicated below (numbers in rings indicate numbering convention):

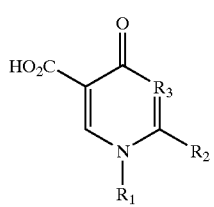

-continued

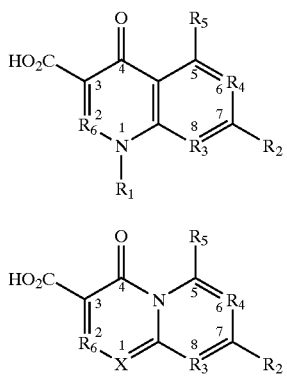

wherein:

X is N or a ring carbon substituted with substituent $R_1$;

$R_1$ is selected from the group consisting of optionally substituted alkyl, alkenyl, alkynyl, cycloalkyl, and aryl;

$R_2$ is selected from the group consisting of optionally substituted alkyl, alkenyl, alkynyl, cycloalkyl, alkylcycloalkyl, halo, hydroxyl, and saturated or unsaturated 4–10 membered mono or bicylic heterocyclyl containing 1, 2 or 3 heteroatoms selected from S, N and O, that may be optionally substituted with one or more alkyl, alkenyl, alkynyl, amino, alkylamino, aminoalkyl, alkylaminoalkyl, or naturally occurring amino acid residues;

$R_3$ is N or a ring carbon substituted with substituent $R_8$;

$R_4$ is N or a ring carbon substituted with substituent $R_9$;

$R_5$ is selected from the group consisting of H, halo, amino (e.g., $NH_2$), alkylamino, and lower alkyl (e.g., methyl);

$R_6$ is N or a ring carbon substituted with substituent $R_7$;

$R_7$ is selected from the group consisting of H, halo and lower alkyl; or $R_1$ and $R_7$ may be joined to form an optionally substituted 4–8 membered heterocycle comprising 1–3 heteroatoms selected from the group consisting of S, N and O;

$R_8$ is selected from the group consisting of H, optionally substituted aryl (e.g., unsubstituted or substituted with halo, e.g., F), optionally substituted alkyl (e.g., unsubstituted or substituted with halo), alkenyl, alkynyl, alkoxy, amino, alkylamino, cyano, nitro or halo (e.g., F); or $R_1$ and $R_8$ may be joined to form an optionally substituted, fused 4–8 membered heterocyclic or carbocyclic ring (which may be saturated or unsaturated, or aromatic), wherein the heterocyclic ring comprises 1–3 heteroatoms selected from the group consisting of S, N and O; and $R_9$ is selected from the group consisting of H, optionally substituted aryl (e.g., unsubstituted or substituted with halo, e.g., F), optionally substituted alkyl (e.g., unsubstituted or substituted with halo), alkenyl, alkynyl, alkoxy, amino, alkylamino, cyano, nitro or halo (e.g., F); or $R_2$ and $R_9$ may be joined to form an optionally substituted, fused 4–8 membered heterocyclic or carbocyclic ring (which may be saturated or unsaturated, or aromatic), wherein the heterocyclic ring comprises 1–3 heteroatoms selected from the group consisting of S, N and O.

Compounds of the invention include those having any one of formulas (1)–(8), comprising the segment A–B, which is a radical having any one of pyridone formulas (9), (10), or (11), as described above, wherein:

X is N;

$R_1$ is selected from the group consisting of optionally substituted lower alkyl, lower cycloalkyl and phenyl;

$R_2$ is selected from the group consisting of optionally substituted piperidinyl, pyrrolidinyl and piperazinyl heterocycles optionally fused with a 3–6 membered carbocycle or heterocycle;

$R_3$ is N or a ring carbon substituted with substituent $R_8$;

$R_4$ is N or a ring carbon substituted with substituent $R_9$;

$R_5$ is selected from the group consisting of H, halo, $NH_2$, and lower alkyl (e.g., methyl);

$R_6$ is N or a ring carbon substituted with substituent $R_7$;

$R_7$ is selected from the group consisting of H, halo and lower alkyl; or $R_1$ and $R_7$ may be joined to form an optionally substituted 5–6 membered heterocycle comprising 1–3 heteroatoms selected from the group consisting of S, N and O;

$R_8$ is selected from the group consisting of H, amino, halo, unsubstituted aryl, aryl substituted with halo, unsubstituted alkyl, alkyl substituted with halo; or $R_1$ and $R_8$ may be joined to form an optionally substituted, fused 4–6 membered heterocyclic or carbocyclic ring (which may be saturated or unsaturated, or aromatic), wherein the heterocyclic ring comprises 1–3 heteroatoms selected from the group consisting of S, N and O; and $R_9$ is selected from the group consisting of H, amino, halo, unsubstituted aryl, aryl substituted with halo, unsubstituted alkyl, alkyl substituted with halo; or $R_1$ and $R_8$ may be joined to form an optionally substituted, fused 4–6 membered heterocyclic or carbocyclic ring (which may be saturated or unsaturated, aromatic), wherein the heterocyclic ring comprises 1–3 heteroatoms selected from the group consisting of S, N and O.

Additional examples of the compounds of the invention are compounds of formulas (1)–(8), comprising the segment A–B which is a radical having any one of pyridone formulas (9), (10), or (11), as described above, wherein:

X is N;

$R_1$ is selected from the group consisting of ethyl, fluoroethyl, cyclopropyl, 4-fluorophenyl or 2,4-difluorophenyl;

$R_2$ is selected from the group consisting of:

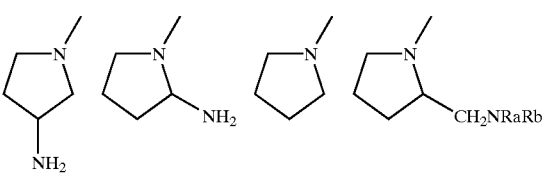

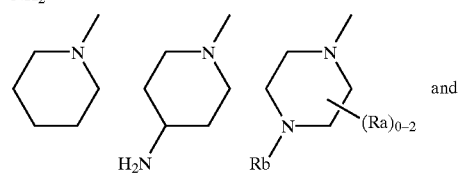

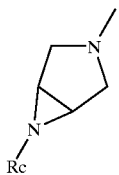

optionally fused with a 3–6 membered carbocycle or heterocycle, and wherein each Ra and Rb is independently selected from the group consisting of H and lower alkyl (e.g., H), and Rc is selected from the group consisting of H, lower alkyl and a chain of 1–6 amino acid residues;

$R_3$ is N or a ring carbon substituted with substituent $R_8$;

$R_4$ is N or a ring carbon substituted with substituent $R_9$;

$R_5$ is selected from the group consisting of H, halo, $NH_2$, and methyl;

$R_6$ is N or a ring carbon substituted with substituent $R_7$;

$R_7$ is selected from the group consisting of H, halo and lower alkyl; or $R_1$ and $R_7$ may be joined to form an optionally substituted 6 membered heterocycle comprising 1–3 heteroatoms selected from the group consisting of S, N and O;

$R_8$ is selected from the group consisting of H, halo, unsubstituted alkyl, aryl substituted with halo, unsubstituted alkyl, alkyl substituted with halo; and $R_9$ is selected from the group consisting of H, halo, unsubstituted alkyl, aryl substituted with halo, unsubstituted alkyl, alkyl substituted with halo.

Some non-limiting examples of $R_2$ used in compounds described herein are selected from the group consisting of:

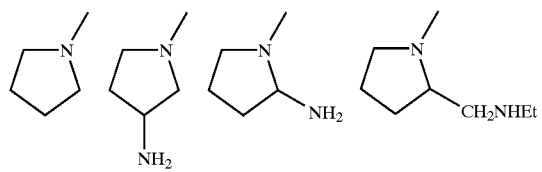

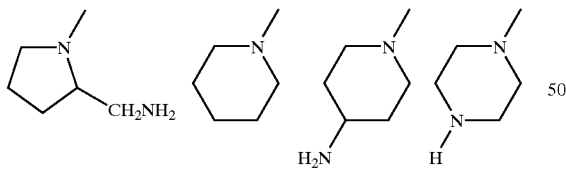

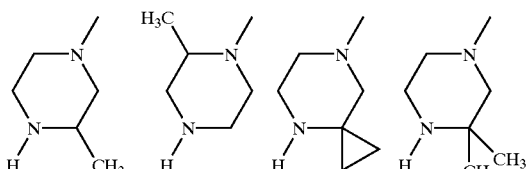

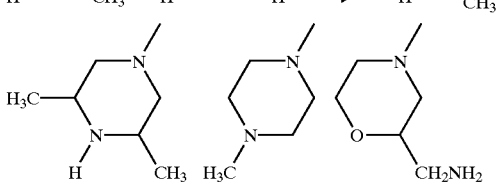

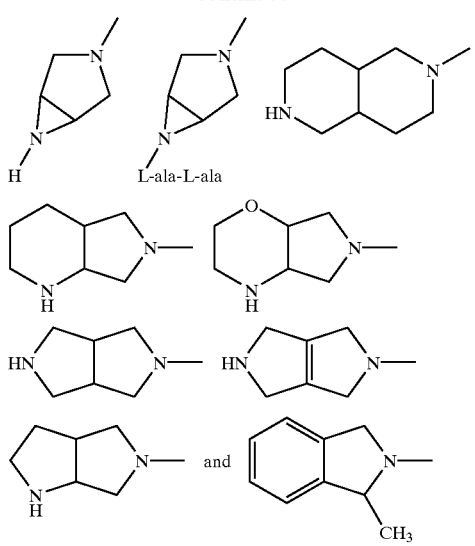

wherein Et is an ethyl radical and L-ala is an L-alanine amino acid residue. Some non-limiting examples of points of attachment for linking examples of $R_2$ to a pyridone moiety and to the remainder of a compound described herein are shown below.

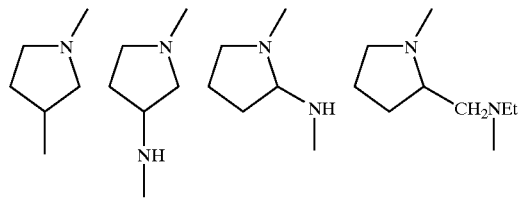

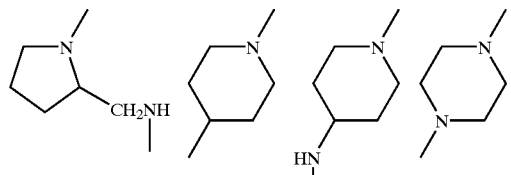

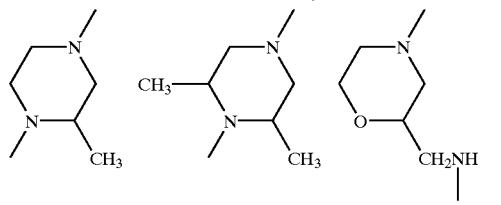

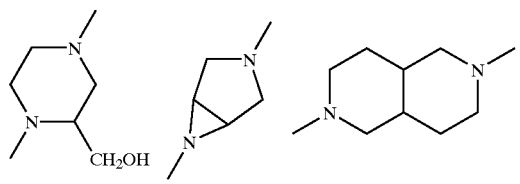

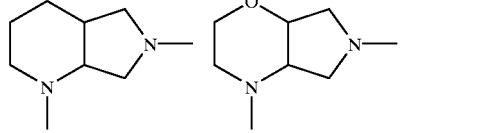

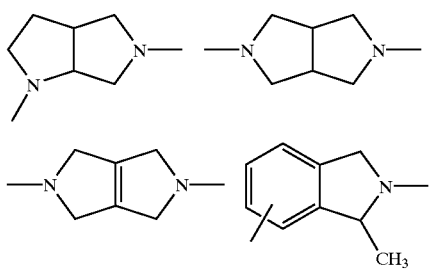

Examples of compounds of the invention include, but are not limited to, the following:

| Compound | Name |
|---|---|
| 1 | 3-{4-[1-(1-ethyl-3-carboxy-4-oxo-6-fluoro-7-quinolyl)-4-piperazinyl]butyl}-6-(3-ethyl-4-methylanilino)uracil |
| 2 | 3-{4-[1-(1-cyclopropyl-3-carboxy-4-oxo-6-fluoro-7-quinolyl)-4-piperazinyl]butyl}-6-(3-ethyl-4-methylanilino)uracil |
| 3 | 3-{4-[1-(1-ethyl-3-carboxy-4-oxo-6-fluoro-7-quinolyl)-4-piperazinyl]butyl}-6-(3-ethyl-4-methylanilino)uracil hydrochloride |
| 4 | 3-{4-[1-(1-ethyl-3-carboxy-4-oxo-6-fluoro-7-quinolyl)-4-piperazinyl]butyl}-6-(3-ethyl-4-methylanilino)uracil methanesulfonate |
| 5 | 3-{4-[1-(1-ethyl-3-carboxy-4-oxo-6-fluoro-8-chloro-7-quinolyl)-4-piperazinyl]butyl}-6-(3-ethyl-4-methylanilino)uracil |
| 6 | 3-{4-[1-(1-ethyl-3-carboxy-4-oxo-6-fluoro-8-aza-7-quinolyl)-4-piperazinyl]butyl}-6-(3-ethyl-4-methylanilino)uracil |
| 7 | 3-{4-[1-(1-ethyl-3-carboxy-4-oxo-6,8-difluoro-7-quinolyl)-4-piperazinyl]butyl}-6-(3-ethyl-4-methylanilino)uracil |
| 8 | 3-{7-[1-(1-cyclopropyl-3-carboxy-4-oxo-6-fluoro-7-quinolyl)-4-piperazinyl]heptyl}-6-(3-ethyl-4-methylanilino)uracil |
| 9 | 3-{4-[1-(1-cyclopropyl-3-carboxy-4-oxo-6-fluoro-7-quinolyl)-4-amino]butyl}-6-(3-ethyl-4-methylanilino)uracil |
| 10 | 3-{4-[1-(1-cyclopropyl-3-carboxy-4-oxo-6-fluoro-7-quinolyl)-4-piperazinyl]butyl}-6-(3-ethyl-4-methylanilino)uracil methanesulfonate |
| 11 | 3-{2-[1-(1-cyclopropyl-3-carboxy-4-oxo-6-fluoro-7-quinolyl)-4-piperazinyl]ethoxyethyl}-6-(3-ethyl-4-methylanilino)uracil |
| 12 | 3-{4-[1-(1-{2,4-difluorophenyl}-3-carboxy-4-oxo-6-fluoro-7-quinolyl)-4-piperazinyl]butyl}-6-(3-ethyl-4-methylanilino)uracil |
| 13 | 3-{4-[1-(1-{2-hydroxyethyl}-3-carboxy-4-oxo-6-fluoro-7-quinolyl)-4-piperazinyl]butyl}-6-(3-ethyl-4-methylanilino)uracil |
| 14 | 3-{4-[1-(1-{4-fluorophenyl}-3-carboxy-4-oxo-6-fluoro-7-quinolyl)-4-piperazinyl]butyl}-6-(3-ethyl-4-methylanilino)uracil |
| 15 | 3-{5-[1-(1-cyclopropyl-3-carboxy-4-oxo-6-fluoro-7-quinolyl)-4-piperazinyl]pentyl}-6-(3-ethyl-4-methylanilino)uracil |
| 16 | 3-{5-[1-(1-ethyl-3-carboxy-4-oxo-6-fluoro-8-aza-7-quinolyl)-4-piperazinyl]pentyl}-6-(3-ethyl-4-methylanilino)uracil |
| 17 | 3-{4-[1-(1-tert-butyl-3-carboxy-4-oxo-6-fluoro-7-quinolyl)-4-piperazinyl]butyl}-6-(3-ethyl-4-methylanilino)uracil |
| 18 | 3-{4-[1-(1-{2,4-difluorophenyl}-3-carboxyl-4-oxo-6-fluoro-8-methoxy-7-quinolyl)-4-piperazinyl]butyl}-6-(3-ethyl-4-methylanilino)uracil |
| 19 | 3-{4-[1-(1-cyclopropyl-3-carboxy-4-oxo-6-fluoro-7-quinolyl)-4-piperazinyl]butyl}-6-(3-ethyl-4-methylanilino)isocytosine |
| 20 | 9-{4-[1-(1-cyclopropyl-3-carboxy-4-oxo-6-fluoro-7-quinolyl)-4-piperazinyl]butyl}-N$^2$-(3-ethyl-4-methylphenyl)guanine |
| 21 | 3-{4-[1-(1-cyclopropyl-3-carboxy-4-oxo-6-fluoro-7-quinolyl)-4-piperazinyl]butyl}-6-(3-ethyl-4-methylanilino)uracil hydrochloride |
| 22 | 3-{4-[1-(1-ethyl-3-carboxy-4-oxo-6-fluoro-8-methoxy-7-quinolyl)-4-piperazinyl]butyl}-6-(3-ethyl-4-methylanilino)uracil |
| 23 | 3-{4-[1-(1-cyclopropyl-3-carboxy-4-oxo-6-fluoro-8-methoxy-7-quinolyl)-4-piperazinyl]butyl}-6-(3-ethyl-4-methylanilino)uracil |
| 24 | 3-{4-[3-(1-ethyl-3-carboxy-4-oxo-6-fluoro-7-quinolyl)aminomethyl-1-pyrrolidinyl]butyl}-6-(3-ethyl-4-methylanilino)uracil |
| 25 | 3-{4-[3-(1-cyclopropyl-3-carboxy-4-oxo-6-fluoro-7-quinolyl)aminomethyl-1-pyrrolidinyl]butyl}-6-(3-ethyl-4-methylanilino)uracil |
| 26 | 3-{4-[3-(1-(2,4-difluorophenyl)-3-carboxy-4-oxo-6-fluoro-7-quinolyl)aminomethyl-1-pyrrolidinyl]butyl}-6-(3-ethyl-4-methylanilino)uracil |
| 27 | 3-{4-[1-(1-ethyl-3-carboxy-4-oxo-6-pyridyl)-4-piperazinyl]butyl}-6-(3-ethyl-4-methylanilino)uracil |
| 28 | 3-{4-[1-(1-cyclopropyl-3-carboxy-4-oxo-6-pyridyl)-4-piperazinyl]butyl}-6-(3-ethyl-4-methylanilino)uracil |
| 29 | 3-{4-[1-(1-{2,4-difluorophenyl}-3-carboxy-4-oxo-6-pyridyl)-4-piperazinyl]butyl}-6-(3-ethyl-4-methylanilino)uracil |
| 30 | 3-{4-[3-(1-ethyl-3-carboxy-4-oxo-6-fluoro-7-quinolyl)aminomethyl-1-pyrrolidinyl]butyl}-6-(3-ethyl-4-methylanilino)isocytosine |
| 31 | 3-{4-[1-(1-cyclopropyl-3-carboxy-4-oxo-6-fluoro-7-quinolyl)aminomethyl-1-pyrrolidinyl]butyl}-6-(3-ethyl-4-methylanilino)isocytosine |
| 32 | 3-{4-[1-(1-{2,4-difluorophenyl}-3-carboxy-4-oxo-6-fluoro-7-quinolyl)aminomethyl-1-pyrrolidinyl]butyl}-6-(3-ethyl-4-methylanilino)isocytosine |
| 33 | 3-{4-[1-(1-ethyl-3-carboxy-4-oxo-6-pyridyl)-4-piperazinyl]butyl}-6-(3-ethyl-4-methylanilino)isocytosine |
| 34 | 3-{4-[1-(1-cyclopropyl-3-carboxy-4-oxo-6-pyridyl)-4-piperazinyl]butyl}-6-(3-ethyl-4-methylanilino)isocytosine |
| 35 | 3-{4-[1-(1-{2,4-difluorophenyl}-3-carboxy-4-oxo-6-pyridyl)-4-piperazinyl]butyl}-6-(3-ethyl-4-methylanilino)isocytosine |
| 36 | 9-{4-[1-(1-ethyl-3-carboxy-4-oxo-6-fluoro-7-quinolyl)-4-piperazinyl]butyl}-N$^2$l-(3-ethyl-4-methylphenyl)guanine |
| 37 | 9-{5-[1-(1-[2,4-difluorophenyl]-3-carboxy-4-oxo-6-fluoro-7-quinolyl)-4-piperazinyl]pentyl}-N$^2$-(3-ethyl-4-methylphenyl)guanine |
| 38 | 9-{5-[1-(1-cyclopropyl-3-carboxy-4-oxo-6-fluoro-8-aza-7-quinolyl)-4-piperazinyl]pentyl}-N$^2$-(3-ethyl-4-methylphenyl)guanine |
| 39 | 9-{5-[1-(1-ethyl-3-carboxy-4-oxo-6-fluoro-7-quinolyl)-4-piperazinyl]pentyl}-2-(3-ethyl-4-methylanilino)adenine |
| 40 | 9-{5-[1-(1-[2,4-difluorophenyl]-3-carboxy-4-oxo-6-fluoro-7-quinolyl)-4-piperazinyl]pentyl}-2-(3-ethyl-4-methylanilino)adenine |
| 41 | 9-{5-[1-(1-cyclopropyl-3-carboxy-4-oxo-6-fluoro-8-aza-7-quinolyl)-4-piperazinyl]pentyl}-2-(3-ethyl-4-methylanilino)adenine |
| 42 | 3-{5-[1-(1-ethyl-3-carboxy-4-oxo-6-fluoro-8-methoxy-7-quinolyl)-4-piperazinyl]pentyl}-6-(3-ethyl-4-methylanilino)uracil |
| 43 | 3-{5-[1-(1-{cyclopropyl}-3-carboxy-4-oxo-6-fluoro-8-methoxy-7-quinolyl)-4-piperazinyl]pentyl}-6-(3-ethyl-4-methylanilino)uracil |
| 44 | 3-{5-[3-(1-ethyl-3-carboxy-4-oxo-6-fluoro-7-quinolyl)aminomethyl-1-pyrrolidinyl]pentyl}-6-(3-ethyl-4-methylanilino)uracil |
| 45 | 3-{5-[3-(1-cyclopropyl-3-carboxy-4-oxo-6-fluoro-7-quinolyl)aminomethyl-1-pyrrolidinyl]pentyl}-6-(3-ethyl-4-methylanilino)uracil |
| 46 | 3-{5-[3-(1-(2,4-difluorophenyl)-3-carboxy-4-oxo-6-fluoro-7-quinolyl)aminomethyl-1-pyrrolidinyl]pentyl}-6-(3-ethyl-4-methylanilino)uracil |

| Compound | Name |
|---|---|
| 47 | 3-{5-[1-(1-ethyl-3-carboxy-4-oxo-6-pyridyl)-4-piperazinyl]pentyl}-6-(3-ethyl-4-methylanilino)uracil |
| 48 | 3-{5-[1-(1-cyclopropyl-3-carboxy-4-oxo-6-pyridyl)-4-piperazinyl]pentyl}-6-(3-ethyl-4-methylanilino)uracil |
| 49 | 3-{5-[1-(1-{2,4-difluorophenyl}-3-carboxy-4-oxo-6-pyridyl)-4-piperazinyl]pentyl}-6-(3-ethyl-4-methylanilino)uracil |
| 50 | 3-{5-[3-(1-ethyl-3-carboxy-4-oxo-6-fluoro-7-quinolyl)aminomethyl-1-pyrrolidinyl]pentyl}-6-(3-ethyl-4-methylanilino)isocytosine |
| 51 | 3-{5-[1-(1-cyclopropyl-3-carboxy-4-oxo-6-fluoro-7-quinolyl)aminomethyl-1-pyrrolidinyl]pentyl}-6-(3-ethyl-4-methylanilino)isocytosine |
| 52 | 3-{5-[1-(1-{2,4-difluorophenyl}-3-carboxy-4-oxo-6-fluoro-7-quinolyl)aminomethyl-1-pyrrolidinyl]pentyl}-6-(3-ethyl-4-methylanilino)isocytosine |
| 53 | 3-{5-[1-(1-ethyl-3-carboxy-4-oxo-6-pyridyl)-4-piperazinyl]pentyl}-6-(3-ethyl-4-methylanilino)isocytosine |
| 54 | 3-{5-[1-(1-cyclopropyl-3-carboxy-4-oxo-6-pyridyl)-4-piperazinyl]pentyl}-6-(3-ethyl-4-methylanilino)isocytosine |
| 55 | 3-{5-[1-(1-{2,4-difluorophenyl}-3-carboxy-4-oxo-6-pyridyl)-4-piperazinyl]pentyl}-6-(3-ethyl-4-methylanilino)isocytosine |
| 64 | 3-{4-[1-(1-cyclopropyl-3-carboxy-4-oxo-6-fluoro-7-quinolyl)-4-piperazinyl]butyl}-6-(3-chloro-4-methylanilino)uracil |
| 65 | 3-{4-[1-(1-cyclopropyl-3-carboxy-4-oxo-6-fluoro-7-quinolyl)-4-piperazinyl]butyl}-6-(3,4-dimethylanilino)uracil |
| 66 | 3-{4-[1-(1-cyclopropyl-3-carboxy-4-oxo-6-fluoro-7-quinolyl)-4-piperazinyl]butyl}-6-(3-ethylanilino)uracil |
| 67 | 3-{4-[1-(1-cyclopropyl-3-carboxy-4-oxo-6-fluoro-7-quinolyl)-4-piperazinyl]butyl}-6-(5-indanylamino)uracil |
| 68 | 3-{4-[1-(1-cyclopropyl-3-carboxy-4-oxo-6-fluoro-7-quinolyl)-4-piperazinyl]butyl}-6-(3,4-dichlorobenzylamino)uracil |
| 69 | 3-{4-[1-(1-cyclopropyl-3-carboxy-4-oxo-6-fluoro-7-quinolyl)-(2-methylpiperazinyl)]butyl}-6-(3-ethyl-4-methylanilino)uracil |
| 70 | 3-{4-[1-(1-cyclopropyl-3-carboxy-4-oxo-6,8-difluoro-7-quinolyl)-4-(3-methylpiperazinyl)]butyl}-6-(3-ethyl-4-methylanilino)uracil |
| 71 | (S)-3-{4-[1-(1-cyclopropyl-3-carboxy-4-oxo-6,8-difluoro-7-quinolyl)-4-(3-methylpiperazinyl)]butyl}-6-(3-ethyl-4-methylanilino)uracil |
| 72 | (R)-3-{4-[1-(1-cyclopropyl-3-carboxy-4-oxo-6,8-difluoro-7-quinolyl)-4-(3-methylpiperazinyl)]butyl}-6-(3-ethyl-4-methylanilino)uracil |
| 73 | 3-{4-[1-(1-cyclopropyl-3-carboxy-4-oxo-6-fluoro-8-methoxy-7-quinolyl)-4-(3-methylpiperazinyl)]butyl}-6-(3-ethyl-4-methylanilino)uracil |
| 74 | 3-{4-[1-(1-{2,4-difluorophenyl}-3-carboxy-4-oxo-6-fluoro-7-quinolyl)-4-(3-methylpiperazinyl]butyl}-6-(3-ethyl-4-methylanilino)uracil |
| 75 | 7-{4-[1-(1-cyclopropyl-3-carboxy-4-oxo-6-fluoro-7-quinolyl)-4-piperazinyl]butyl}-N²-(3-ethyl-4-methylphenyl)guanine |
| 76 | 7-{4-[1-(1-cyclopropyl-3-carboxy-4-oxo-6-fluoro-7-quinolyl)-4-piperazinyl]butyl}-2-(3-ethyl-4-methylanilino)adenine |
| 77 | 3-{[1-(1-ethyl-3-carboxy-4-oxo-6-fluoro-7-quinolyl)-4-piperazinyl]carboxamido}-6-(3-ethyl-4-methylanilino)-2-pyridone |
| 78 | 3-{4-[1-(1-ethyl-3-carboxy-4-oxo-6-fluoro-7-quinolyl)-4-piperazinyl]butyl}-6-(3-ethyl-4-methylanilino)-2-pyridone |
| 79 | 3-{4-[1-(1-ethyl-3-carboxy-4-oxo-6,8-diaza-7-quinolyl)-4-piperazinyl]butyl}-6-(3-ethyl-4-methylanilino)uracil |
| 80 | 3-{5-[1-(1-ethyl-3-carboxy-4-oxo-6-fluoro-7-quinolyl)-3-(1,3-diazabicyclononyl)]pentyl}-6-(3-ethyl-4-methylanilino)uracil |
| 81 | 3-{5-[1-(1-cyclopropyl-3-carboxy-4-oxo-6-fluoro-7-quinolyl)-3-(1,3-diazabicyclooctyl)]pentyl}-6-(3-ethyl-4-methylanilino)uracil |
| 82 | 3-{5-[1-(1-cyclopropyl-3-carboxy-4-oxo-6-fluoro-7-quinolyl)-3-(1,3-diazabicyclononyl)]pentyl}-6-(3-ethyl-4-methylanilino)uracil |
| 83 | 3-{5-[1-(1-cyclopropyl-3-carboxy-4-oxo-6-fluoro-7-quinolyl)-3-(pyrrolidinylamino)]pentyl}-6-(3-ethyl-4-methylanilino)uracil |
| 84 | 3-{5-[1-(1-cyclopropyl-3-carboxy-4-oxo-6-fluoro-7-quinolyl)-3-(5-oxa-1,3-diazabicyclononyl)]pentyl}-6-(3-ethyl-4-methylanilino)uracil |
| 85 | 3-{5-[1-(1-ethyl-3-carboxy-4-oxo-6,8-difluoro-7-quinolyl)-3-(5-oxa-1,3-diazabicyclononyl)]pentyl}-6-(3-ethyl-4-methylanilino)uracil |
| 86 | 3-{5-[1-(1-cyclopropyl-3-carboxy-4-oxo-6-fluoro-7-quinolyl)-4-(1,4-diazabicyclooctyl)]pentyl}-6-(3-ethyl-4-methylanilino)uracil |
| 87 | 3-{4-[1-(1-cyclopropyl-3-carboxy-4-oxo-6-fluoro-7-quinolyl)-3-(5-oxa-1,3-diazabicyclononyl)]butyl}-6-(3-ethyl-4-methylanilino)uracil |
| 88 | 3-{5-[1-(1-ethyl-3-carboxy-4-oxo-6,8-difluoro-7-quinolyl)-3-(1,3-diazabicyclononyl)]pentyl}-6-(3-ethyl-4-methylanilino)uracil |
| 89 | 3-{4-[1-(1-{2,4-difluorophenyl}-3-carboxy-4-oxo-6-fluoro-7-quinolyl)-4-(3-methylpiperazinyl)]butyl}-6-(3-ethyl-4-methylanilino)uracil |
| 90 | (R)-3-{4-[1-(1-{2,4-difluorophenyl}-3-carboxy-4-oxo-6-fluoro-7-quinolyl)-4-(3-methylpiperazinyl)]butyl}-6-(3-ethyl-4-methylanilino)uracil |
| 91 | 3-{4-[1-(1-cyclopropyl-3-carboxy-4-oxo-6,8-difluoro-7-quinolyl)-4-(3-hydroxymethylpiperazinyl)]butyl}-6-(3-ethyl-4-methylanilino)uracil |
| 92 | 3-{4-[1-(1-cyclopropyl-3-carboxy-4-oxo-6,8-difluoro-7-quinolyl)-4-(3-methylpiperazinyl)]butyl}-6-(5-indanylamino)uracil |
| 93 | 3-{4-[1-(1-cyclopropyl-3-carboxy-4-oxo-6,8-difluoro-7-quinolyl)-4-(3-methylpiperazinyl)]butyl}-6-(3-chloro-4-methylanilino)uracil |
| 94 | 3-{4-[1-(1-cyclopropyl-3-carboxy-4-oxo-6,8-difluoro-7-quinolyl)-4-(3-methylpiperazinyl)]butyl}-6-(3,4-dimethylanilino)uracil |
| 95 | (R)-3-{4-[1-(1-cyclopropyl-3-carboxy-4-oxo-6-fluoro-7-quinolyl)-4-(3-methylpiperazinyl)]butyl}-6-(3-ethyl-4-methylanilino)uracil |
| 96 | (R)-3-{4-[1-(1-cyclopropyl-3-carboxy-4-oxo-6-fluoro-7-quinolyl)-4-(3-methylpiperazinyl)]butyl}-6-(3,4-dimethylanilino)uracil |
| 97 | (S)-3-{4-[1-(1-cyclopropyl-3-carboxy-4-oxo-6-fluoro-7-quinolyl)-4-(3-methylpiperazinyl)]butyl}-6-(3,4-dimethylanilino)uracil |
| 98 | (R)-3-{4-[1-(1-cyclopropyl-3-carboxy-4-oxo-6,8-difluoro-7-quinolyl)-4-(3-methylpiperazinyl)]butyl}-6-(3,4-dimethylanilino)uracil |
| 99 | (S)-3-{4-[1-(1-cyclopropyl-3-carboxy-4-oxo-6,8-difluoro-7-quinolyl)-4-(3-methylpiperazinyl)]butyl}-6-(3,4-dimethylanilino)uracil |
| 100 | (S)-3-{4-[1-(1-cyclopropyl-3-carboxy-4-oxo-6-fluoro-7-quinolyl)-4-(3-methylpiperazinyl)]butyl}-6-(3-ethyl-4-methylanilino)uracil |
| 101 | 3-{4-[1-(1-cyclopropyl-3-carboxy-4-oxo-6,8-difluoro-7-quinolyl)-4-(piperazinyl)]butyl}-6-(3,4-dimethylanilino)uracil |
| 102 | 3-{4-[1-(1-cyclopropyl-3-carboxy-4-oxo-6-fluoro-8-methoxy-7-quinolyl)-4-(3-methylpiperazinyl)]butyl}-6-(3-ethyl-4-methylanilino)uracil |
| 103 | 3-{4-[1-(1-cyclopropyl-3-carboxy-4-oxo-6-fluoro-8-methoxy-7-quinolyl)-4-(3-methylpiperazinyl)]butyl}-6-(3,4-dimethylanilino)uracil |
| 104 | 3-{4-[1-(1-cyclopropyl-3-carboxy-4-oxo-6,8-difluoro-7-quinolyl)-4-(3-carboxypiperazinyl)]butyl}-6-(3-ethyl-4-methylanilino)uracil |
| 105 | 3-{4-[1-(1-cyclopropyl-3-carboxy-4-oxo-7-quinolyl)-4-piperazinyl]butyl}-6-(3-ethyl-4-methylanilino)uracil |
| 106 | 3-{4-[1-(1-allyl-3-carboxy-4-oxo-7-quinolyl)-4-piperazinyl]butyl}-6-(3-ethyl-4-methylanilino)uracil |

-continued

| Compound | Name |
|---|---|
| 107 | (R)-3-{4-[1-(1-cyclopropyl-3-carboxy-4-oxo-7-quinolyl)-8-difluoromethoxy)-4-(3-methylpiperazinyl)]butyl}-6-(3-ethyl-4-methylanilino)uracil |
| 108 | (R)-3-{4-[2-(1-cyclopropyl-3-carboxy-4-oxo-7-quinolyl-8-difluoromethoxy)-2,3-dihydro-1-methyl-isoindol-5-yl)]butyl}-6-(3-ethyl-4-methylanilino)uracil |
| 109 | 3-{4-[1-(1-ethyl-3-carboxy-4-oxo-6,8-diaza-7-quinolyl)-4-(3-methylpiperazinyl)]butyl}-6-(3-ethyl-4-methylanilino)uracil |

Intermediates useful in synthesizing other compounds include, but are not limited to the following:

| Compound | Name |
|---|---|
| 56 | 3-{4-[1-(1-cyclopropyl-3-ethoxycarbonyl-4-oxo-6-fluoro-7-quinolyl)-4-piperazinyl]butyl}-6-(3-ethyl-4-methylanilino)uracil |
| 57 | 3-(4-methoxybutyl)-6-anilinouracil |
| 58 | 3-{2-[1-(1-cyclopropyl-3-benzyloxycarbonyl-4-oxo-6-fluoro-7-quinolyl)-4-piperazinyl]ethoxyethyl}-6-(3-ethyl-4-methylanilino)uracil |

-continued

| Compound | Name |
|---|---|
| 59 | 3-{4-[1-(1-cyclopropyl-3-ethoxycarbonyl-4-oxo-6-fluoro-7-quinolyl)-4-piperazinyl]butyl}-6-anilinouracil |
| 60 | 3-{4-[1-(1-{2,4-difluorophenyl}-3-ethoxycarbonyl-4-oxo-6-fluoro-7-quinolyl)-4-piperazinyl]butyl}-6-(3-ethyl-4-methylanilino)uracil |
| 61 | 3-{4-[1-(1-{2-hydroxyethyl}-3-ethoxycarbonyl-4-oxo-6,8-difluoro-7-quinolyl)-4-piperazinyl]butyl}-6-(3-ethyl-4-methylanilino)uracil |
| 62 | 3-{4-[1-(1-{4-fluorophenyl}-3-ethoxycarbonyl-4-oxo-6-fluoro-7-quinolyl)-4-piperazinyl]butyl}-6-(3-ethyl-4-methylanilino)uracil (an intermediate compound useful in synthesizing other compounds) |
| 63 | 9-{4-[1-(1-cyclopropyl-3-ethoxycarbonyl-4-oxo-6-fluoro-7-quinolyl)-4-piperazinyl]butyl}-2-(3-ethyl-4-methylanilino)-6-iodopurine (an intermediate compound useful in synthesizing other compounds) |

Some compounds of the invention have one or more chiral centers. Such compounds may be provided as individual, pure species, such as individual enantiomers (see, e.g., Compounds 71 and 72) or diastereomers, or as mixtures of one or more species, including racemic mixtures of enantiomers. Accordingly, chiral compounds and mixtures of chiral compounds may or may not be optically active as determined by standard methods known in the art for detecting optical activity of compounds having one or more chiral centers.

Methods of Synthesis and Characterization of Compounds

The compounds of the invention may be synthesized according to standard organic chemistry synthesis protocols, including combinatorial chemistry protocols. The structures of the compounds described herein may be viewed as essentially discrete segments. Accordingly, each compound may be synthesized from segments in an optimal sequence of steps based on availability of starting materials and stocks. This segment synthetic approach for making compounds of the invention is illustrated below in four non-limiting, exemplary synthetic schemes.

A representative compound of the invention consisting of segments A, B, C, D, and E is indicated below. Each segment of the compound is approximately indicated by the dividing lines between the bond linking each segment to its neighboring segment or segments.

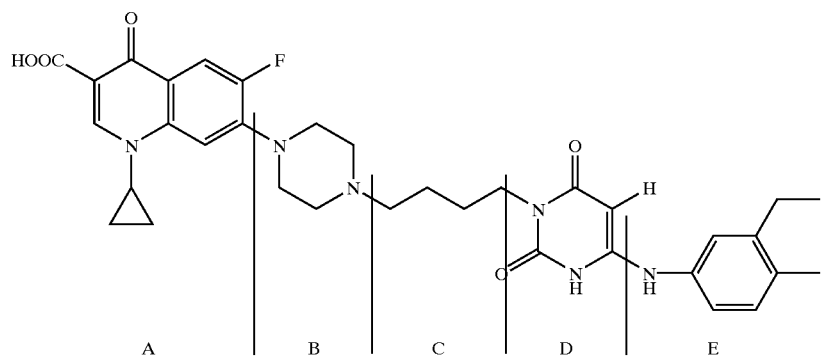

The above compound may be synthesized by several different schemes. Depending on the availability of starting materials and intermediate compounds, such synthetic schemes may differ by sequence in which selected segments are linked, such as those indicated below:

Method I A+B–C–D–E

Method II A–B+C–D–E

Method III A–B–C+D–E

Method IV A–B–C–D+E

Method V A+B+C–D–E

Examples of each of the above alternative synthetic approaches are outlined below, showing how each step may be carried out using protocols and equipment available to persons skilled in organic molecule synthesis.

Method I
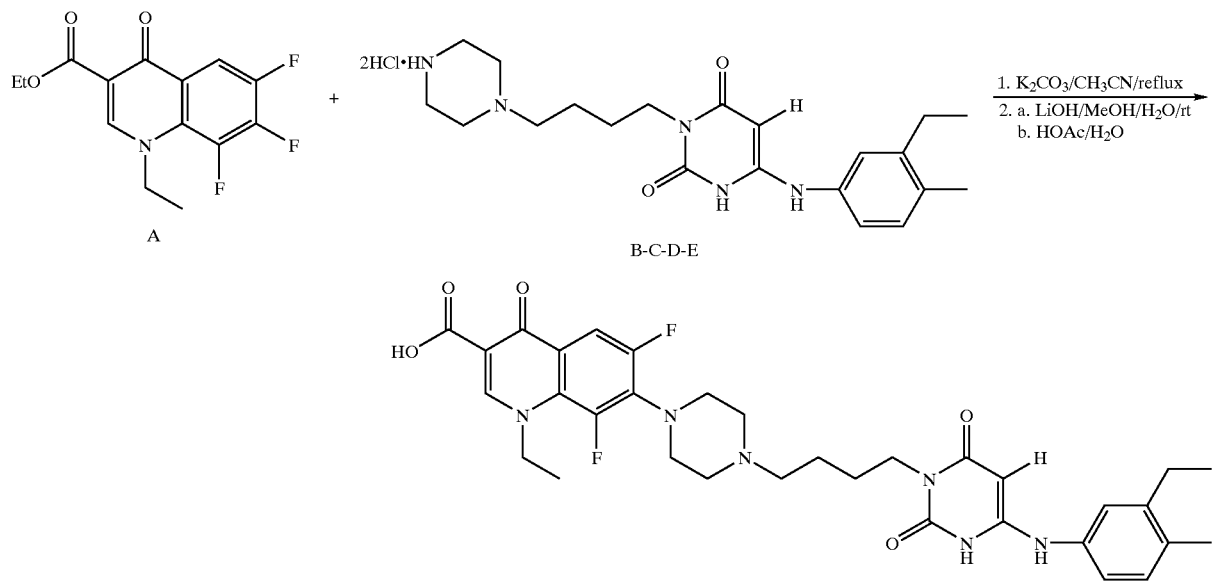
Method II
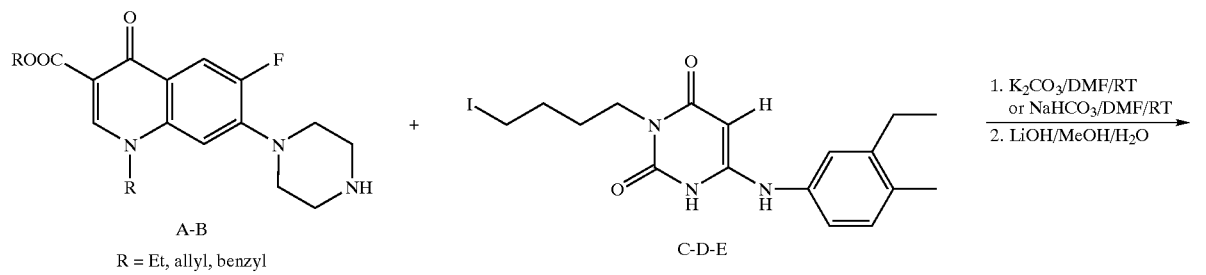
Method III
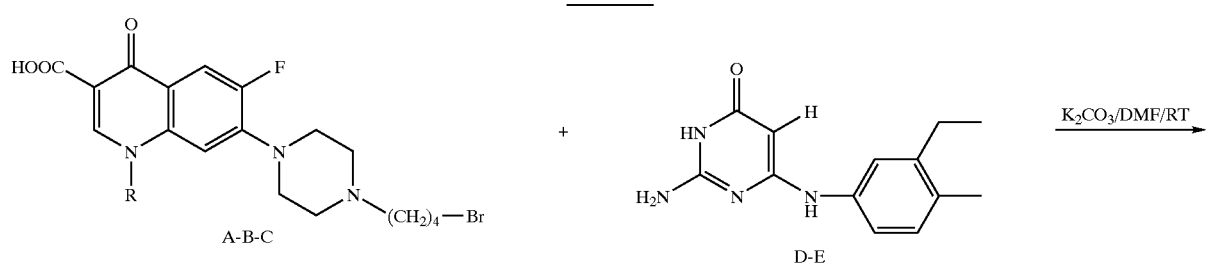

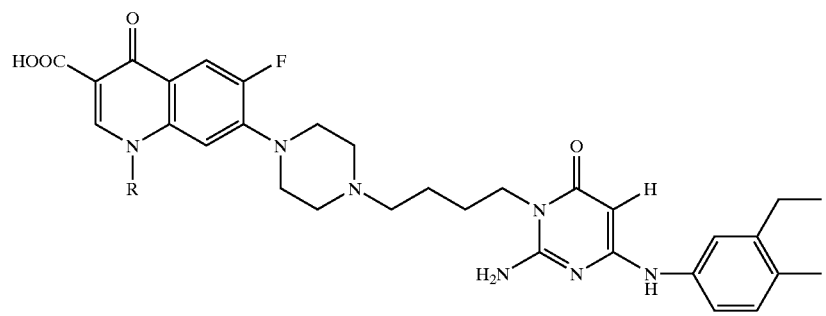
Method IV
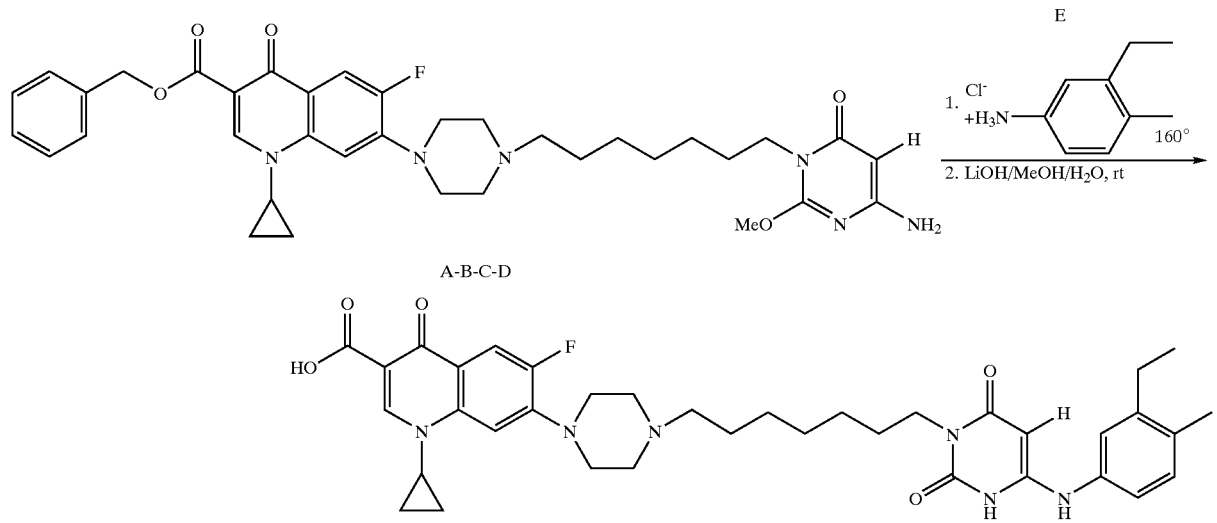
Method V (2 schemes)
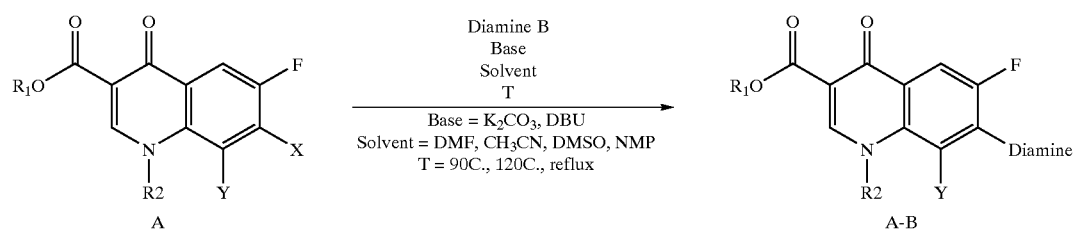
R1 = H, Et
X = F, Y = F, R2 = Et
X = Cl, Y = H, R2 = Et, cyclopropyl
X = F, Y = H, R2 = cyclopropyl
Method II
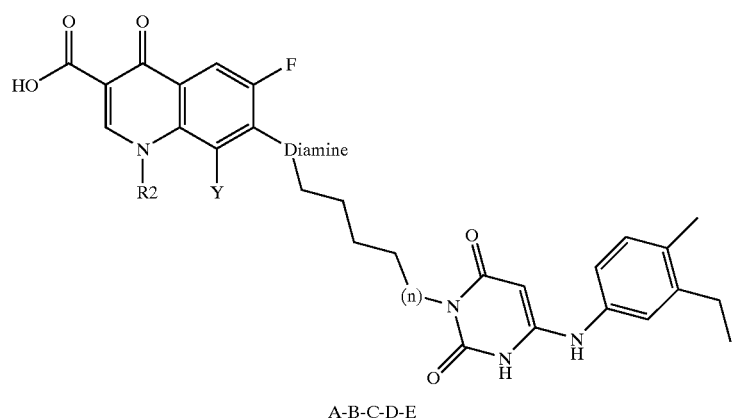
A-B-C-D-E Diamines
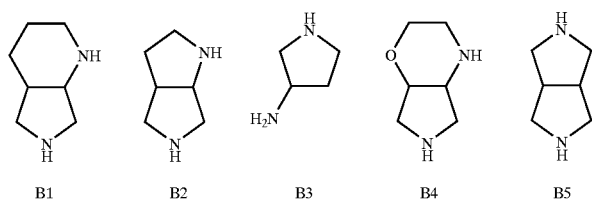
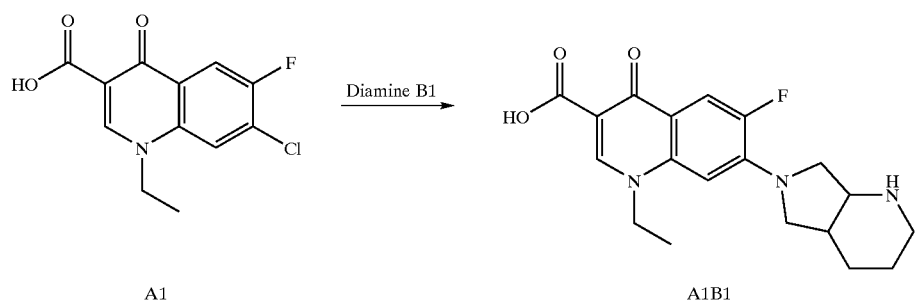
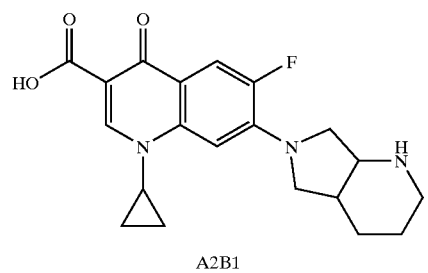
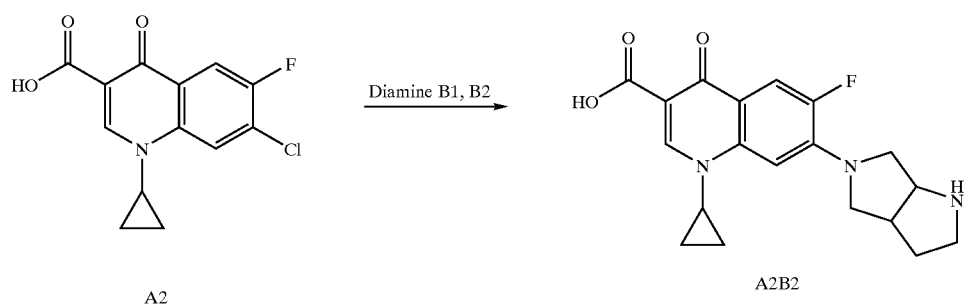
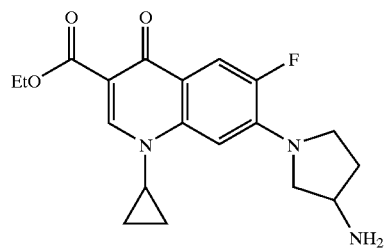

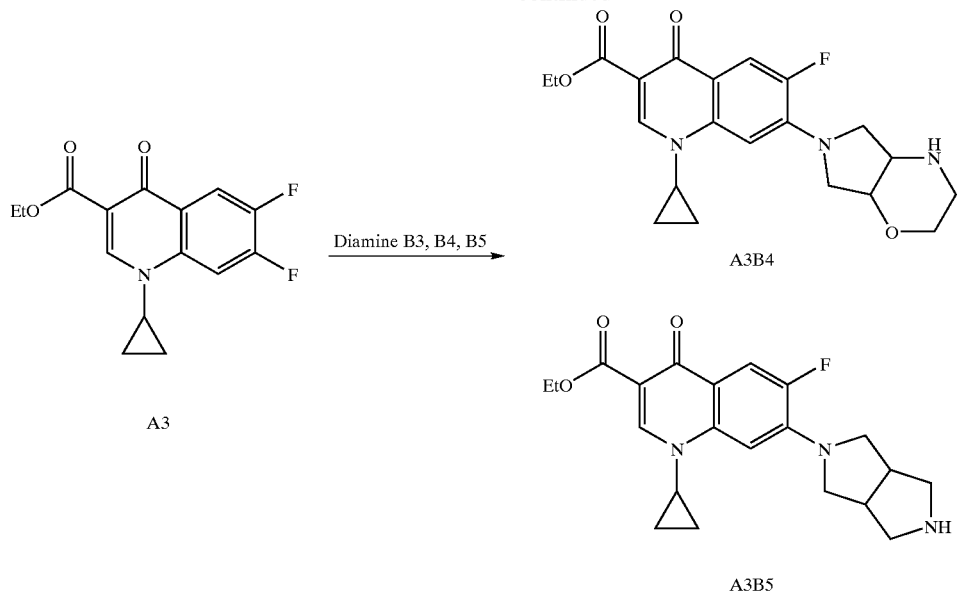

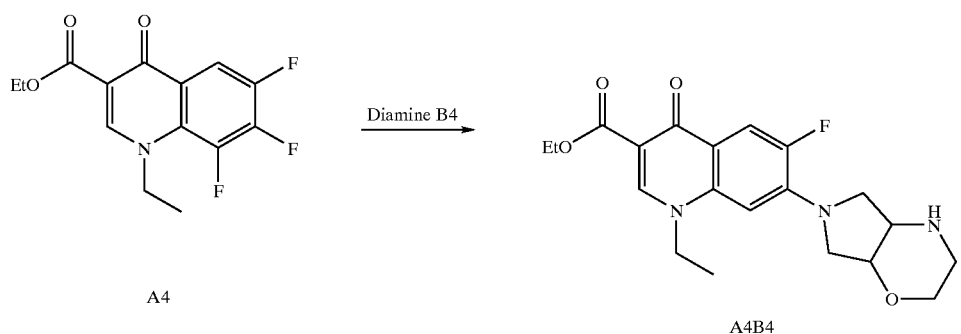

Quinolone A3 may be prepared by standard methods known in the art (see, e.g., *J. Heterocycl. Chem.*, 24(1): 181–185 (1987)). Quinolone A4 maybe prepared by standard methods known in the art starting from commercially available 1-ethyl-6,7,8-trifluoro-1,4-dihydro-4-oxo-3-quinoline carboxylic acid. Quinolones A1 and A2 may be obtained commercially.

In addition to the general synthetic schemes described above, a new synthetic method has been developed which is useful for synthesizing 3-substituted-6-(arylamino)uracils and 3-substituted-6-(arylalkyl)aminouracils compounds described herein. General methods for the preparation of certain $N^3$-substituted-6-anilinouracils have been published (P. Tarantino, C. Zhi, J. Gambino, G. E. Wright and N. C. Brown, "6-Anilinouracil-based Inhibitors of *Bacillus subtilis* DNA Polymerase III: Antipolymerase and Antimicrobial Structure-Activity Relationships Based on Substitution at Uracil N3," *J. Med. Chem.*, 42, 2035–2040 (1999)). An example of such methods is illustrated below for synthesis of 3-(4-methoxybutyl)-6-(3-ethyl-4-methylanilino)uracil, a precursor of intermediates such as 3-(4-iodobutyl)-6-(3-ethyl-4-methylanilino)uracil and related compounds used as starting materials for the compounds:

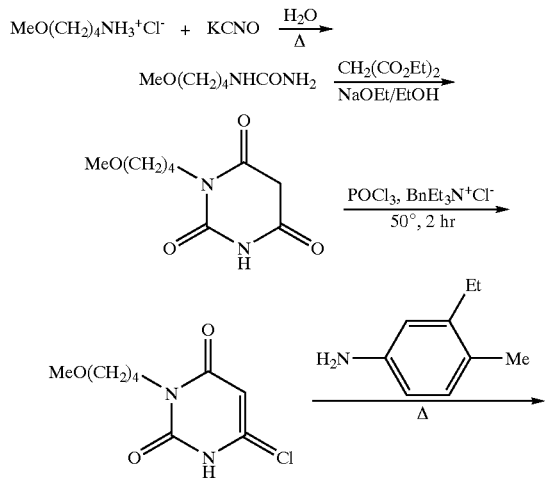

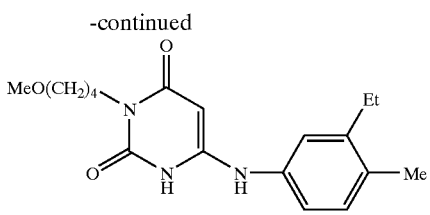

However, the above synthetic sequence is not suitable for preparing useful amounts of derivatives containing a reactive group in the 3-substituent because such compounds would decompose under the strongly basic or acidic conditions of one of the steps above. A new method has, therefore, been developed and is the subject of a concurrently filed, copending U.S. application. This new method is a two-step procedure, illustrated in the following scheme:

Step 1

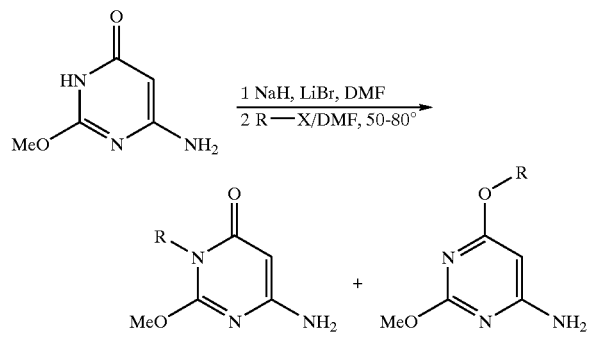

Step 2

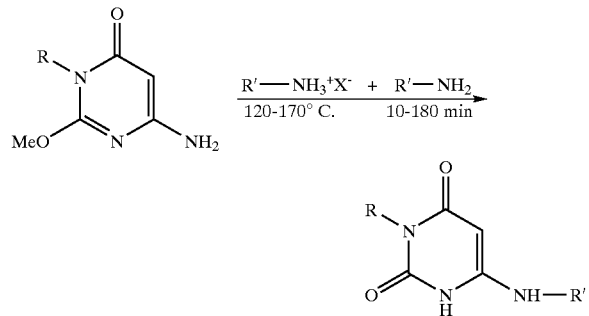

where R-X is a substituted alkyl halide (chloride, bromide, or iodide), R' is substituted alkyl, arylalkyl, aryl or heteroaryl.

In Step 1 of the above synthetic method, sodium hydride (1.2 eq) is added to a mixture of 6-amino-2-methoxy-4-pyrimidone (1 eq) in N,N-dimethylformamide (DMF) at 0° C. Then lithium bromide (1.2–2.0 eq) is added, and the mixture is stirred for 1 hour at room temperature. The mixture is added dropwise to a solution of the alkylating agent (1.5 eq) in DMF at 50–80° C., and the reaction mixture is stirred at 50–80° C. for 3–10 hours. After cooling to room temperature, the solvent is removed. The residue is purified by chromatography on silica gel with chloroform:methanol as eluent, to give first the 04-alkyl compound and then the 6-amino-2-methoxy-3-substituted-4-pyrimidone.

In Step 2 of the above synthetic method, a mixture of 6-amino-2-methoxy-3-substituted-4-pyrimidone (1.0 eq), substituted-amine salt (1.2–2.5 eq), and a few drops or crystals of the substituted amine (ca. 0.1–1 eq) is heated at 120–170° C. for between 10 minutes to 3 hours. After cooling to room temperature, water is added, and the mixture is extracted with chloroform. The combined organic layers are dried over anhydrous magnesium sulfate. The solvent is removed under reduced pressure, and the residue is purified by chromatography on silica gel with chloroform::methanol as eluent to give the target compounds, 3-alkyl-6-(substituted-amino) uracils in high yields. This step results in simultaneous displacement of the 6-amino group and demethylation of the 2-methoxy group to afford the uracil, i.e., 2,4-dioxo compound, directly. Using this new synthetic method, base-labile and acid-labile groups in the 3-R substituent are stable under these conditions.

The structure of a compound described herein can be determined by standard methods, such as nuclear magnetic resonance (NMR) and other assays to confirm structural features of organic molecules.

Each compound of the invention may also be tested for desired biochemical and antibacterial (antibiotic) activities using standard methods for determining inhibition of particular enzyme activities (i.e., bacterial polymerase IIIC and type II bacterial topoisomerase activites) and the ability to kill or inhibit bacterial growth. Compounds of the invention inhibit bacterial polymerase IIIC. Compounds of the invention include those that have a level of polymerase IIIC inhibitory activity that is greater than that found in previously known inhibitors of polymerase IIIC. Another bacterial enzyme target that may be inhibited by compounds described herein is type II bacterial topoisomerase. Useful compounds of the invention may inhibit both bacterial polymerase IIIC and type II bacterial topoisomerase. Although such biochemical activities of a compound are readily determined by standard methods, without being bound by any particular theory of mode of action, the invention provides compounds that find particular use as antibacterial agents, i.e., as antibiotics.

For example, each compound may be tested for antibiotic activity, including the range of bacterial species susceptible to killing by the compound and minimal inhibitory concentration (IIIC), by detecting growth, or lack thereof, of one or more bacterial species on agar or liquid growth media supplemented with various concentrations of the compound (see, e.g., Daly et al., *Antimicrob. Agents Chemother.*, 44: 2217–2221 (2000)). For example, a test of a compound described herein may be assayed against one or more strains of Gram positive bacteria (e.g., species of Bacillus, Enterococcus, or Staphylococcus), mycoplasma bacteria, or Gram negative bacteria (e.g., *Escherichia coli, Salmonella typhimurium, Salmonella typhi*), which can be grown on an agar medium supplemented with different concentrations of the compound. Typically, such a solid test medium is prepared using a stock solution of the test compound in dimethylsulfoxide (DMSO), water, or aqueous buffer, depending on the solubility of the test compound, which is added in an appropriate amount to a batch of sterile, molten agar medium at a temperature of 60° C. After addition of the compound, the medium may be mixed and then poured into Petri plates and allowed to solidify. Test media may be prepared to make agar plates containing a test compound in a series of two-fold serial dilutions, e.g., from about 80 to 0.625 mg/ml. One-tenth ml of diluted bacteria containing 500–1000 colony-forming units (CFU) are plated and spread, and the plates incubated at 37° C. for 24 hours. MIC is equivalent to the lowest concentration at which growth, i.e., colony formation, is not observed.

Assays for testing protection from lethal bacterial infection in vivo are also well known (see, e.g., Tarantino et al., *Antimicrob. Agents Chemother.*, 43: 1982–1987 (1999)).

Inhibition of polymerase IIIC may be determined by detecting inhibition of polymerase IIIC activity, for example using polymerase IIIC assay (see, e.g., Barnes et al., *Nucleic Acids Res.*, 6: 1203–1219 (1979); Tarantino et al., *Antimicrob. Agents Chemother.*, 43: 1982–1987 (1999)). Likewise, inhibition of a type II topoisomerase may be determined using a method of assaying topoisomerase isomerase (see, e.g., Domagala et al., *J. Med. Chem.*, 29: 394–404 (1986)).

Pharmaceutical Compositions Routes of Administration

It will be appreciated that the amount of a compound of the invention required for use in therapeutic or prophylactic treatment of an individual against a bacterial infection will vary not only with the particular compound selected, but also with such factors as the route of administration, the nature of the condition or disease for which treatment is required, and the age and condition of the patient. Such factors are ultimately at the discretion of the attendant physician or veterinarian. In general, however, dosages are those that produce a sustained concentration at a level higher than the $MIC_{90}$ value (i.e., the concentration of a compound that inhibits the growth of 90% of the strains of bacteria evaluated). The desired dose may conveniently be presented in a single dose or as divided dose administered at appropriate intervals, for example, as two, three, four, or more doses per day.

Administration of a compound of the invention to a patient may be achieved by intravenous injection of a solution of the compound, optionally in saline, or by another appropriate route (see below). Desirable blood levels may be maintained by a continuous infusion or by intermittent infusions.

While it is possible that, for use in therapy, a compound of the invention may be administered as the raw chemical, the compound may be presented as an active ingredient in a pharmaceutical composition. The invention thus further provides a pharmaceutical composition comprising a compound or a pharmaceutically acceptable salt thereof together with one or more pharmaceutically acceptable carriers therefor and, optionally, other therapeutic or beneficial agents, such as, another antibiotic, antiviral compound, anti-cancer compound, vitamin, trace metal supplement, or ions to restore or maintain proper ionic balance in blood or other tissues. Other examples of suitable therapeutic agents that may be used in combination with the compounds of this invention include, without limitation, penicillins and other beta lactamase inhibitors, carbapenems, cephalosporins, macrolides (including erythromycin and ketolides), sulfonamides, aminoglycosides, quinolones (such as fluoroquinolones), oxazolidinones, lipopeptides (such as daptomycin), tetracyclines, vancomycin, erythromycin, streptomycin, efflux pump inhibitors, lactoferrins, and cationic peptides. Such agents may be administered together with or separately from the compounds of this invention. In addition, certain patients may suffer from or may be susceptible to simultaneous infections from bacteria and one or more viruses. Those patients may benefit from simultaneous or separate co-administration of a compound or formulation according to this invention and an anti-viral agent, for example, without limitation, an anti-influenza medication such as Relenza (zanamivir) and Tamiflu (oseltamivir) or an anti-enteric virus drug such as pleconaril. Additional combination therapies may also include a compound of this invention and an anti-fungal agent, such as Cancidas (caspofungin acetate), Diflucan (fluconazole), and Mycostatin (nystatin). Clearly, the combination therapies described herein are merely exemplary and are not meant to limit possibilities for other combination treatments or co-administration regimens.

The pharmaceutically acceptable carrier(s) used in the pharmaceutical compositions of the invention must be "acceptable" in the sense of being compatible with the other agents and ingredients of the formulation and not prohibitively deleterious to the patient, to whom the pharmaceutical composition is administered.

Pharmaceutical compositions include those suitable for oral, rectal, nasal, auricular (ear), ocular, topical (including buccal and sub-lingual), transdermal, vaginal, or parenteral (including intramuscular, sub-cutaneous, and intravenous) administration or in a form suitable for administration by inhalation or insufflation. The pharamaceutical compositions may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired composition.

Pharmaceutical compositions suitable for oral administration may conveniently be presented as discrete units such as capsules, cachets, or tablets each containing a predetermined amount of a compound of the invention in a powder or granule form, in a solution, in a suspension, or as an emulsion. A compound of the invention may also be presented as a bolus, electuary, or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection as a bolus or by continuous infusion) and may be presented in unit dose form in ampoules, pre-filled syringes, small volume infusion, or in multi-dose containers with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form, obtained by aseptic isolation of sterile solid or by lyophilization from solution, for constitution with a suitable vehicle, e.g., sterile, pyrogen-free water, prior to use.

For topical administration to the epidermis, the compounds according to the invention may be formulated as ointments, creams, gels, jellies, or lotions. A compound of the invention may also be incorporated into a transdermal patch. Such transdermal patches may contain penetration enhancers such as linalool, carvacrol, thymol, citral, menthol, t-anethole, and the like. Ointments and creams may, for example, be formulated with an aqueous or oily base comprising one or more suitable thickening and/or gelling agents. Lotions may be formulated with an aqueous or oily base and will in general also contain one or more emulsifying agents, stabilizing agents, dispersing agents, suspending agents, thickening agents, or coloring agents.

Compositions suitable for topical administration of compound of the invention in the mouth include lozenges comprising the compound, optionally, in a flavored base, usually sucrose and acacia or tragacanth; pastilles comprising the compound in an inert base such as gelatin and glycerin or sucrose and acacia; and mouthwashes comprising the active ingredient in a suitable liquid carrier.

Pharmaceutical compositions suitable for rectal administration wherein the carrier is a solid are presented as unit dose suppositories. Suitable carriers include cocoa butter and other materials commonly used in the art, and the suppositories may be conveniently formed by admixture of a compound of the invention with the softened or melted carrier(s) followed by chilling and shaping in molds.

Pharmaceutical compositions suitable for vaginal administration may be presented as pessaries, tampons, creams, gels, pastes, foams, or sprays containing in addition to a compound of the invention such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents, or suspending agents. Liquid sprays may conveniently be delivered from pressurized packs.

For administration by inhalation, the compounds according to the invention may conveniently be delivered from an insufflator, nebulizer, a pressurized pack, or other convenient means of delivering an aerosol spray. Pressurized packs may comprise a suitable propellant, such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example, a powder mix of a compound of the invention and a suitable powder base such as lactose or starch. The powder composition may be presented in unit dosage form in, for example, capsules or cartridges, or, for example, gelatin or blister packs from which the powder may be administered with the aid of an inhalator or insufflator.

A compound of the invention may also be formulated into a pharmaceutical composition treating an eye or ear infection. Diseases of the eye that may be treated by administering a compound of the invention to a patient include, but are not limited to, bacterial keratitis, infectious keratoconjunctivitis, bacterial conjunctivitis, ocular tuberculosis, and suppurative uveitis. Diseases of ear that may be treated by administering a compound of the invention include, but are not limited to, otitis externa and otitis media. Eye and ear diseases may be treated by administering a compound to a patient by any of the various routes described above or by direct administration to the infected eye or ear. Pharmaceutical compositions comprising a compound of the invention for treating an eye or ear disease may be a liquid or lotion, which may be administered directly into or on the infected eye or ear. Such compositions may be formulated in a manner similar to any of those known and used to administer an antibiotic to an eye or ear, such as compositions comprising fluoroquinolones (see, e.g., *Am. Fam. Physician,* 62: 1870–1876 (2000), and references cited therein).

When desired, the above described compositions may be adapted to give a sustained or time-delayed release of compound of the invention using any of the sustained or time-delayed formats available in art.

The compounds of the invention may also be used in combination with other antimicrobial compounds, antiviral compounds, anticancer compounds, vitamins, trace metal supplements, or ionic buffers designed to maintain or correct proper ionic balance in blood or other tissues.

The compositions referred to above may conveniently be presented for use in the form of a pharmaceutical composition, and thus, pharmaceutical compositions comprising a combination as defined above together with a pharmaceutically acceptable carrier therefor comprise a further aspect of the invention.

In addition, the individual components of such combinations may be administered either sequentially or simultaneously in separate or combined pharmaceutical compositions. When a compound of the invention or a pharmaceutically acceptable salt thereof is used in combination with a second therapeutic compound, the dose of each compound may be either the same as or differ from that when the compound is used alone. Appropriate doses will be readily appreciated by those skilled in the art.

The ratio between a compound of the present invention and a second therapeutic compound for co-administration to a patient will be readily appreciated by those skilled in the art. For example, one may use a ratio in the range from about 1:1 to about 1:50 (by weight) of compound of the invention:second therapeutic compound or, vice versa, i.e., of the second compound:compound of the invention. In additional embodiments, the ranges of ratios that may be used in preparing a composition for co-administration of a compound of the invention with a second therapeutic compound include, without limitation: about 1:1 to about 1:30 (by weight), about 1:1 to about 1:20 (by weight), about 1:1 to about 1:15 (by weight), about 1:1 to about 1:10 (by weight), about 1:1 to about 1:5 (by weight), and about 1:1 to about 1:3 (by weight) of a compound of the invention:second therapeutic compound, or vice versa. If yet a further therapeutic compound(s) is added, ratios are adjusted accordingly.

A compound of the invention may be provided and packaged in any of a variety of forms as described above, including in a powder or lyophilized state for reconstitution with sterile water or buffer, in unit doses for convenient administration, with one or more pharmaceutically acceptable buffers or salts, and/or with instructions for using the packaged compound as an antibiotic to treat an infection or as a enzyme inhibitor in polymerase IIIC and/or type II topoisomerase assays.

The following examples are provided to illustrate various embodiments of the present invention and shall not be considered as limiting in scope.

EXAMPLES

Example 1

Representative Compounds

Unless noted otherwise, the following compounds were synthesized using methods described herein and/or standard organic synthesis methods known in the art. The compounds were then characterized for structure and/or various activities.

| Compound | Name |
|---|---|
| 1 | 3-{4-[1-(1-ethyl-3-carboxy-4-oxo-6-fluoro-7-quinolyl)-4-piperazinyl]butyl}-6-(3-ethyl-4-methylanilino)uracil |
| 2 | 3-{4-[1-(1-cyclopropyl-3-carboxy-4-oxo-6-fluoro-7-quinolyl)-4-piperazinyl]butyl}-6-(3-ethyl-4-methylanilino)uracil |
| 3 | 3-{4-[1-(1-ethyl-3-carboxy-4-oxo-6-fluoro-7-quinolyl)-4-piperazinyl]butyl}-6-(3-ethyl-4-methylanilino)uracil hydrochloride |
| 4 | 3-{4-[1-(1-ethyl-3-carboxy-4-oxo-6-fluoro-7-quinolyl)-4-piperazinyl]butyl}-6-(3-ethyl-4-methylanilino)uracil methanesulfonate |

-continued

| Compound | Name |
|---|---|
| 5 | 3-{4-[1-(1-ethyl-3-carboxy-4-oxo-6-fluoro-8-chloro-7-quinolyl)-4-piperazinyl]butyl}-6-(3-ethyl-4-methylanilino)uracil |
| 6 | 3-{4-[1-(1-ethyl-3-carboxy-4-oxo-6-fluoro-8-aza-7-quinoly)-4-piperazinyl]butyl}-6-(3-ethyl-4-methylanilino)uracil |
| 7 | 3-{4-[1-(1-ethyl-3-carboxy-4-oxo-6,8-difluoro-7-quinolyl)-4-piperazinyl]butyl}-6-(3-ethyl-4-methylanilino)uracil |
| 8 | 3-{7-[1-(1-cyclopropyl-3-carboxy-4-oxo-6-fluoro-7-quinolyl)-4-piperazinyl]heptyl}-6-(3-ethyl-4-methylanilino)uracil |
| 56 | 3-{4-[1-(1-cyclopropyl-3-ethoxycarbonyl-4-oxo-6-fluoro-7-quinolyl)-4-piperazinyl]butyl}-6-(3-ethyl-4-methylanilino)uracil |
| 9 | 3-{4-[1-(1-cyclopropyl-3-carboxy-4-oxo-6-fluoro-7-quinolyl)-4-amino]butyl}-6-(3-ethyl-4-methylanilino)uracil |
| 57 | 3-(4-methoxybutyl)-6-anilinouracil |
| 58 | 3-{2-[1-(1-cyclopropyl-3-benzyloxycarbonyl-4-oxo-6-fluoro-7-quinolyl)-4-piperazinyl]ethoxyethyl}-6-(3-ethyl-4-methylanilino)uracil |
| 59 | 3-{4-[1-(1-cyclopropyl-3-ethoxycarbonyl-4-oxo-6-fluoro-7-quinoly)-4-piperazinyl]butyl}-6-anilinouracil |
| 10 | 3-{4-[1-(1-cyclopropyl-3-carboxy-4-oxo-6-fluoro-7-quinolyl)-4-piperazinyl]butyl}-6-(3-ethyl-4-methylanilino)uracil methanesulfonate |
| 11 | 3-{2-[1-(1-cyclopropyl-3-carboxy-4-oxo-6-fluoro-7-quinolyl)-4-piperazinyl]ethoxyethyl}-6-(3-ethyl-4-methylanilino)uracil |
| 60 | 3-{4-[1-(1-{2,4-difluorophenyl}-3-ethoxycarbonyl-4-oxo-6-fluoro-7-quinolyl)-4-piperazinyl]butyl}-6-(3-ethyl-4-methylanilino)uracil |
| 12 | 3-{4-[1-(1-{2,4-difluorophenyl}-3-carboxy-4-oxo-6-fluoro-7-quinolyl)-4-piperazinyl]butyl}-6-(3-ethyl-4-methylanilino)uracil |
| 61 | 3-{4-[1-(1-{2-hydroxyethyl}-3-ethoxycarbonyl-4-oxo-6,8-difluoro-7-quinolyl)-4-piperazinyl]butyl}-6-(3-ethyl-4-methylanilino)uracil |
| 13 | 3-{4-[1-(1-{2-hydroxyethyl}-3-carboxy-4-oxo-6-fluoro-7-quinolyl)-4-piperazinyl]butyl}-6-(3-ethyl-4-methylanilino)uracil |
| 62 | 3-{4-[1-(1-{4-fluorophenyl}-3-ethoxycarbonyl-4-oxo-6-fluoro-7-quinolyl)-4-piperazinyl]butyl}-6-(3-ethyl-4-methylanilino)uracil |
| 14 | 3-{4-[1-(1-{4-fluorophenyl}-3-carboxy-4-oxo-6-fluoro-7-quinolyl)-4-piperazinyl]butyl}-6-(3-ethyl-4-methylanilino)uracil |
| 15 | 3-{5-[1-(1-cyclopropyl-3-carboxy-4-oxo-6-fluoro-7-quinolyl)-4-piperazinyl]pentyl}-6-(3-ethyl-4-methylanilino)uracil |
| 16 | 3-{5-[1-(1-ethyl-3-carboxy-4-oxo-6-fluoro-8-aza-7-quinolyl)-4-piperazinyl]pentyl}-6-(3-ethyl-4-methylanilino)uracil |
| 17 | 3-{4-[1-(1-tert-butyl-3-carboxy-4-oxo-6-fluoro-7-quinolyl)-4-piperazinyl]butyl}-6-(3-ethyl-4-methylanilino)uracil |
| 18 | 3-{4-[1-(1-{2,4-difluorophenyl}-3-carboxyl-4-oxo-6-fluoro-8-methoxy-7-quinolyl)-4-piperazinyl]butyl}-6-(3-ethyl-4-methylanilino)uracil |
| 19 | 3-{4-[1-(1-cyclopropyl-3-carboxy-4-oxo-6-fluoro-7-quinolyl)-4-piperazinyl]butyl}-6-(3-ethyl-4-methylanilino)isocytosine |
| 63 | 9-{4-[1-(1-cyclopropyl-3-ethoxycarbonyl-4-oxo-6-fluoro-7-quinolyl)-4-piperazinyl]butyl}-2-(3-ethyl-4-methylanilino)-6-iodopurine |
| 20 | 9-{4-[1-(1-cyclopropyl-3-carboxy-4-oxo-6-fluoro-7-quinolyl)-4-piperazinyl]butyl}-$N^2$-(3-ethyl-4-methylphenyl)guanine |
| 21 | 3-{4-[1-(1-cyclopropyl-3-carboxy-4-oxo-6-fluoro-7-quinolyl)-4-piperazinyl]butyl}-6-(3-ethyl-4-methylanilino)uracil hydrochloride |
| 64 | 3-{4-[1-(1-cyclopropyl-3-carboxy-4-oxo-6-fluoro-7-quinolyl)-4-piperazinyl]butyl}-6-(3-chloro-4-methylanilino)uracil |
| 65 | 3-{4-[1-(1-cyclopropyl-3-carboxy-4-oxo-6-fluoro-7-quinolyl)-4-piperazinyl]butyl}-6-(3,4-dimethylanilino)uracil |
| 66 | 3-{4-[1-(1-cyclopropyl-3-carboxy-4-oxo-6-fluoro-7-quinolyl)-4-piperazinyl]butyl}-6-(3-ethylanilino)uracil |
| 67 | 3-{4-[1-(1-cyclopropyl-3-carboxy-4-oxo-6-fluoro-7-quinolyl)-4-piperazinyl]butyl}-6-(5-indanylamino)uracil |
| 68 | 3-{4-[1-(1-cyclopropyl-3-carboxy-4-oxo-6-fluoro-7-quinolyl)-4-piperazinyl]butyl}-6-(3,4-dichlorobenzylamino)uracil |
| 69 | 3-{4-[1-(1-cyclopropyl-3-carboxy-4-oxo-6-fluoro-7-quinolyl)-4-(2-methylpiperazinyl)]butyl}-6-(3-ethyl-4-methylanilino)uracil |
| 70 | 3-{4-[1-(1-cyclopropyl-3-carboxy-4-oxo-6,8-difluoro-7-quinolyl)-4-(3-methylpiperazinyl)]butyl}-6-(3-ethyl-4-methylanilino)uracil |
| 71 | (S)-3-{4-[1-(1-cyclopropyl-3-carboxy-4-oxo-6,8-difluoro-7-quinolyl)-4-(3-methylpiperazinyl)]butyl}-6-(3-ethyl-4-methylanhlino)uracil |
| 72 | (R)-3-{4-[1-(1-cyclopropyl-3-carboxy-4-oxo-6,8-difluoro-7-quinolyl)-4-(3-methylpiperazinyl)]butyl}-6-(3-ethyl-4-methylanilino)uracil |
| 73 | 3-{4-[1-(1-cyclopropyl-3-carboxy-4-oxo-6-fluoro-8-methoxy-7-quinolyl)-4-(3-methylpiperazinyl)]butyl}-6-(3-ethyl-4-methylanilino)uracil |
| 74 | 3-{4-[1-(1-{2,4-difluorophenyl}-3-carboxy-4-oxo-6-fluoro-7-quinolyl)-4-(3-methylpiperazinyl)]butyl}-6-(3-ethyl-4-methylanilino)uracil |
| 75 | 7-{4-[1-(1-cyclopropyl-3-carboxy-4-oxo-6-fluoro-7-quinolyl)-4-piperazinyl]butyl}-$N^2$-(3-ethyl-4-methylphenyl)guanine |
| 76 | 7-{4-[1-(1-cyclopropyl-3-carboxy-4-oxo-6-fluoro-7-quinoly)-4-piperazinyl]butyl}-2-(3-ethyl-4-methylanilino)adenine |
| 77 | 3-{[1-(1-ethyl-3-carboxy-4-oxo-6-fluoro-7-quinolyl)-4-piperazinyl]carboxamido}-6-(3-ethyl-4-methylanilino)-2-pyridone |
| 78 | 3-{4-[1-(1-ethyl-3-carboxy-4-oxo-6-fluoro-7-quinolyl)-4-piperazinyl]butyl}-6-(3-ethyl-4-methylanilino)-2-pyridone |
| 79 | 3-{4-[1-(1-ethyl-3-carboxy-4-oxo-6,8-diaza-7-quinolyl)-4-piperazinyl]butyl}-6-(3-ethyl-4-methylanilino)uracil |
| 80 | 3-{5-[1-(1-ethyl-3-carboxy-4-oxo-6-fluoro-7-quinolyl)-3-(1,3-diazabicyclononyl)]pentyl}-6-(3-ethyl-4-methylanilino)uracil |
| 81 | 3-{5-[1-(1-cyclopropyl-3-carboxy-4-oxo-6-fluoro-7-quinolyl)-3-(1,3-diazabicyclooctyl)]pentyl}-6-(3-ethyl-4-methylanilino)uracil |
| 82 | 3-{5-[1-(1-cyclopropyl-3-carboxy-4-oxo-6-fluoro-7-quinolyl)-3-(1,3-diazabicyclononyl)]pentyl}-6-(3-ethyl-4-methylanilino)uracil |
| 83 | 3-{5-[1-(1-cyclopropyl-3-carboxy-4-oxo-6-fluoro-7-quinolyl)-3-(pyrrolidinylamino)]pentyl}-6-(3-ethyl-4-methylanilino)uracil |
| 84 | 3-{5-[1-(1-cyclopropyl-3-carboxy-4-oxo-6-fluoro-7-quinolyl)-3-(5-oxa-1,3-diazabicyclononyl)]pentyl}-6-(3-ethyl-4-methylanilino)uracil |
| 85 | 3-{5-[1-(1-ethyl-3-carboxy-4-oxo-6,8-difluoro-7-quinolyl)-3-(5-oxa-1,3-diazabicyclononyl)]pentyl}-6-(3-ethyl-4-methylanilino)uracil |
| 86 | 3-{5-[1-(1-cyclopropyl-3-carboxy-4-oxo-6-fluoro-7-quinolyl)-4-(1,4-diazabicyclooctyl)]pentyl}-6-(3-ethyl-4-methylanilino)uracil |
| 87 | 3-{4-[1-(1-cyclopropyl-3-carboxy-4-oxo-6-fluoro-7-quinolyl)-3-(5-oxa-1,3-diazabicyclononyl)]butyl}-6-(3-ethyl-4-methylanilino)uracil |
| 88 | 3-{5-[1-(1-ethyl-3-carboxy-4-oxo-6,8-difluoro-7-quinolyl)-3-(1,3-diazabicyclononyl)]pentyl}-6-(3-ethyl-4-methylanilino)uracil |
| 89 | 3-{4-[1-(1-{2,4-difluorophenyl}-3-carboxy-4-oxo-6-fluoro-7-quinolyl)-4-(3-methylpiperazinyl)]butyl}-6-(3-ethyl-4-methylanilino)uracil |
| 90 | (R)-3-{4-[1-(1-{2,4-difluorophenyl}-3-carboxy-4-oxo-6-fluoro-7-quinolyl)-4-(3-methylpiperazinyl)]butyl}-6-(3-ethyl-4-methylanilino)uracil |
| 91 | 3-{4-[1-(1-cyclopropyl-3-carboxy-4-oxo-6,8-difluoro-7-quinolyl)-4-(3-hydroxymethylpiperazinyl)]butyl}-6-(3-ethyl-4-methylanilino)uracil |
| 92 | 3-{4-[1-(1-cyclopropyl-3-carboxy-4-oxo-6,8-difluoro-7-quinolyl)-4-(3-methylpiperazinyl)]butyl}-6-(5-indanylamino)uracil |
| 93 | 3-{4-[1-(1-cyclopropyl-3-carboxy-4-oxo-6,8-difluoro-7-quinolyl)-4-(3-methylpiperazinyl)]butyl}-6-(3-chloro-4-methylanilino)uracil |
| 94 | 3-{4-[1-(1-cyclopropyl-3-carboxy-4-oxo-6,8-difluoro-7-quinolyl)-4-(3-methylpiperazinyl)]butyl}-6-(3,4-dimethylanilino)uracil |
| 95 | (R)-3-{4-[1-(1-cyclopropyl-3-carboxy-4-oxo-6-fluoro-7-quinolyl)-4-(3-methylpiperazinyl)]butyl}-6-(3-ethyl-4-methylanilino)uracil |
| 96 | (R)-3-{4-[1-(1-cyclopropyl-3-carboxy-4-oxo-6-fluoro-7-quinolyl)-4-(3-methylpiperazinyl)]butyl}-6-(3,4-dimethylanilino)uracil |
| 97 | (S)-3-{4-[1-(1-cyclopropyl-3-carboxy-4-oxo-6-fluoro-7-quinolyl)-4-(3-methylpiperazinyl)]butyl}-6-(3,4-dimethylanilino)uracil |
| 98 | (R)-3-{4-[1-(1-cyclopropyl-3-carboxy-4-oxo-6,8-difluoro-7-quinolyl)-4-(3-methylpiperazinyl)]butyl}-6-(3,4-dimethylanilino)uracil |
| 99 | (S)-3-{4-[1-(1-cyclopropyl-3-carboxy-4-oxo-6,8-difluoro-7-quinolyl)-4-(3-methylpiperazinyl)]butyl}-6-(3,4-dimethylanilino)uracil |

| Compound | Name |
|---|---|
| 100 | (S)-3-{4-[1-(1-cyclopropyl-3-carboxy-4-oxo-6-fluoro-7-quinolyl)-4-(3-methylpiperazinyl)]butyl}-6-(3-ethyl-4-methylanilino)uracil |
| 101 | 3-{4-[1-(1-cyclopropyl-3-carboxy-4-oxo-6,8-difluoro-7-quinolyl)-4-(piperazinyl)]butyl}-6-(3,4-dimethylanilino)uracil |
| 102 | 3-{4-[1-(1-cyclopropyl-3-carboxy-4-oxo-6-fluoro-8-methoxy)-7-quinolyl)-4-(3-methylpiperazinyl)]butyl}-6-(3-ethyl-4-methylanilino)uracil |
| 103 | 3-{4-[1-(1-cyclopropyl-3-carboxy-4-oxo-6-fluoro-8-methoxy)-7-quinolyl)-4-(3-methylpiperazinyl)]butyl}-6-(3,4-dimethylanilino)uracil |
| 104 | 3-{4-[1-(1-cyclopropyl-3-carboxy-4-oxo-6,8-difluoro-7-quinolyl)-4-(3-carboxypiperazinyl)]butyl}-6-(3-ethyl-4-methylanilino)uracil |
| 105 | 3-{4-[1-(1-cyclopropyl-3-carboxy-4-oxo-7-quinolyl)-4-piperazinyl]butyl}-6-(3-ethyl-4-methylanilino)uracil |
| 106 | 3-{4-[1-(1-allyl-3-carboxy-4-oxo-7-quinolyl)-4-piperazinyl]butyl}-6-(3-ethyl-4-methylanilino)uracil |
| 107 | (R)-3-{4-[1-(1-cyclopropyl-3-carboxy-4-oxo-7-quinolyl-8-difluoromethoxy)-4-(3-methylpiperazinyl)]butyl}-6-(3-ethyl-4-methylanilino)uracil |
| 108 | (R)-3-{4-[2-(1-cyclopropyl-3-carboxy-4-oxo-7-quinolyl-8-difluoromethoxy)-2,3-dihydro-1-methyl-isoindol-5-yl)]butyl}-6-(3-ethyl-4-methylanilino)uracil |
| 109 | 3-{4-[1-(1-ethyl-3-carboxy-4-oxo-6,8-diaza-7-quinolyl)-4-(3-methylpiperazinyl)]butyl}-6-(3-ethyl-4-methylanilino)uracil |
| EMAU | 6-(3-ethyl-4-methylanilino)uracil |
| HB-EMAU | 3-hydroxybutyl-6-(3-ethyl-4-methylanilino)uracil |

Norfloxacin and ciprofloxacin hydrochloride were obtained from Sigma Chemical Co. (St. Louis, Mo.) and Mediatech Inc., respectively. Ethyl, allyl and benzyl esters of these and related quinolone carboxylic acids were prepared by acid-catalyzed esterification with the corresponding alcohols. Esters for preparation of Compounds 6 and 7 were prepared by methods known in the art (see, e.g., *J. Med. Chem,* 31: 991–1001 (1988) and EP 0 1328 545 A2, respectively).

Synthesis of IB-EMAU

A schematic diagram of the synthesis of 3-(4-iodobutyl)-6-(3-ethyl-4-methylanilino)uracil (IB-EMAU) used in the synthesis of various compounds of the invention is given below.

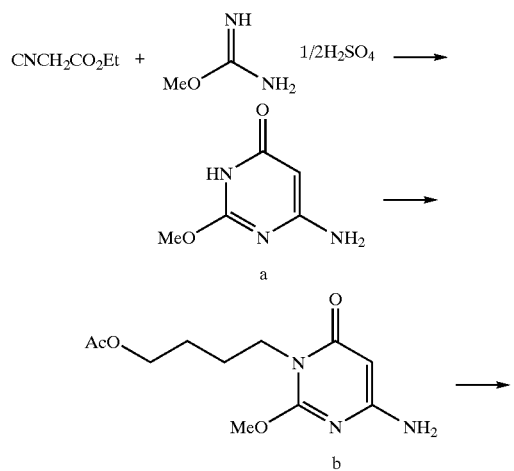

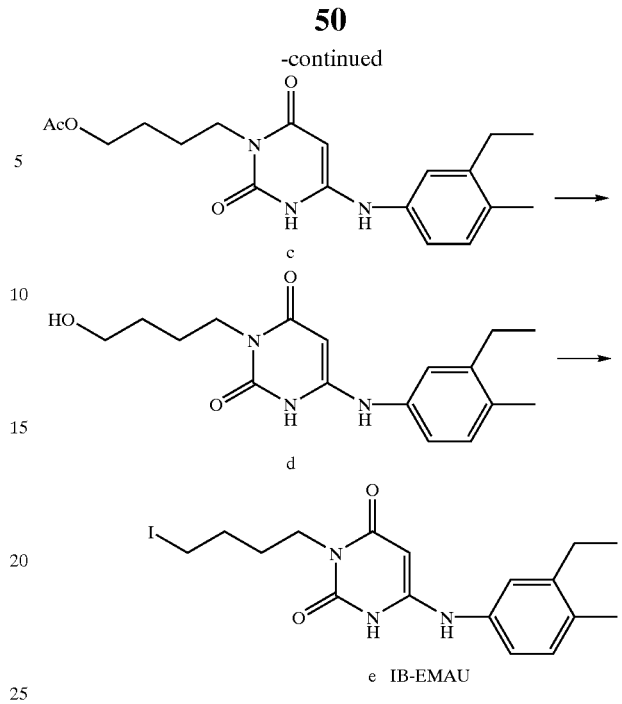

Synthesis of 6-amino-2-methoxy-4-pyrimidone, Compound a

The protocol for synthesizing compound a in the above schematic diagram was that basically as described by W. Pfleiderer (*Chem. Ber.,* 90: 2272 (1957)). Sodium (15 g, 652 mmol) was dissolved, in small portions, in 200 ml methanol. O-Methylisourea hemisulfate (30.6 g, 248 mmol) and ethyl cyanoacetate (30 g, 265 mmol) were added to the solution. The mixture was stirred at reflux for 4.5 hours (h). The mixture was filtered, and the solid was washed carefully with methanol. The combined filtrates were evaporated to dryness, and the white solid residue was dissolved in 300 ml of hot water. After neutralization with acetic acid to pH 7, the solid was filtered, washed with water, and dried to give 28 g (80%) of product as a white solid.

Synthesis of 6-amino-2-methoxy-3-(4-acetoxybutyl)-4-pyrimidone, Compound b (Two Alternative Methods were Used)

Method A. Sodium hydride (60% dispersion in mineral oil, 8.2 g, 205 mmol) was added to a mixture of 6-amino-2-methoxy-4-pyrimidone (24.0 g, 170 mmol) in DMF at 0° C. After 0.5 hours, lithium bromide (19.2 g, 221 mmol) was added to the mixture and stirred for 0.5 hours at room temperature. The temperature was slowly increased to 70° C., and a solution of 4-bromobutyl acetate (50 g, 256 mmol) in DMF was added dropwise to the reaction mixture. The mixture was stirred at 70° C. for 3 hours. After cooling to room temperature, the solvent was removed in vacuo. The residue was purified by chromatography on silica gel using CHCl$_3$/MeOH (1–5%) as eluent to give first 6.5 g (15%) of 6-amino-2-methoxy-4-(4-acetoxybutyl)pyrimidine as a white solid followed by 23.4 g (yield 54%) of 6-amino-2-methoxy-3-(4-acetoxybutyl)-4-pyrimidone as a white solid.

300 MHz $^1$H NMR (DMSO-d$_6$): δ1.52 (m, 4H, 2×CH$_2$), 2.0 (s, 3H, CH$_3$CO) 3.76 (t, 2H, CH$_2$O), 3.88 (s, 3H, CH$_3$N),), 4.0 (t, 2H, CH$_2$O), 4.82 (s, 1H, C$_5$—H), 6.41 (s, 2H, NH$_2$).

Alternative Method B. A mixture of 6-amino-2-methoxy-4-pyrimidone (30 g, 212.6 mmol), K$_2$CO$_3$ (44 g, 318 mmol), benzyltriethylammionium chloride (20 g, 88 mmol) and 4-bromobutyl acetate (60 g, 308 mmol) in acetone (800 ml) was heated at reflux overnight. After cooling to room temperature, the insoluble salts were filtered off and the solvent was removed. The residue was purified by chromatography on silica gel with CHCl₃/MeOH (100:2–100:5) as eluent. After separation of 6-amino-2-methoxy-4-(4-acetoxybutyl)pyrimidine (22.8, yield 42%), 18.7 g (yield 34.5%) of 6-amino-2-methoxy-3-(4-acetoxybutyl)-4-pyrimidone was isolated as a white solid.

Synthesis of 3-(4-acetoxybutyl)-6-(3-ethyl-4-methylanilino) uracil Compound c

A stirred mixture of 3-(4-acetoxybutyl)-6-amino-2-methoxy-4-pyrimidone (15 g. 59 mmol), 3-ethyl-4-methylaniline hydrochloride [Wright and Gambino, J. Med. Chem. 27, 181–185, 1984] (12.1 g, 75 mmol) and 3-ethyl-4-methylaniline (4.0 g, 29 mmol) was heated in an oil bath at 160° C. for 15 minutes. After cooling to room temperature, the residue was dissolved in chloroform:methanol (1:1), and the solution was evaporated with silica gel. The material was placed atop a silica gel column and eluted with chloroform:methanol (100% to 96% chloroform) to give crude product. Trituration with acetone:diethyl ether (1:1) gave colorless crystals of product (17.8 g, 84%).

300 MHz $^1$H NMR (DMSO-$d_6$): δ1.14 (t, 3H, $CH_3CH_2Ar$), 1.53 (m, 4H, 2×$CH_2$), 2.0 (s, 3H, $CH_3CO$), 2.24 (s, 3H, $CH_3Ar$), 2.57 (q, 2H, $CH_2Ar$), 3.71 (t, 2H, $CH_2O$), 3.99 (t, 2H, $CH_2N$), 4.73 (s, 1H, $C_5$—H), 6.92–7.15 (m, 3H, Ar—H), 8.12 (s, 1H, NH), 10.43 (s, 1H, NH).

Synthesis of 3-(4-hydroxybutyl)-6-(3-ethyl-4-methylanilino)uracil, Compound d

Aqueous concentrated ammonia (150 ml) was added to a stirred suspension of 3-(4-acetoxybutyl)-6-(3-ethyl-4-methylanilino)uracil (10.5 g, 24 mmol) in 150 ml of methanol at room temperature. After 30 minutes, all solid was dissolved, and the solution was stirred for 72 hours. The solvent was removed, and the solid was co-evaporated three times with methanol, and filtered from methanol to give the product as a white solid (9.0 g, 97%).

$^1$H NMR (DMSO-$d_6$): δ1.14 (t, 3H, $CH_3CH_2Ar$), 1.38 (m, 2H, $CH_2$), 1.50 (m, 2H, $CH_2$), 2.24 (s, 3H, $CH_3Ar$), 2.57 (q, 2H, $CH_2Ar$), 3.34 (t, 2H, $CH_2O$), 3.67 (t, 2H, $CH_2N$), 4.38 (t, 1H, OH), 4.72 (s, 1H, $C_5$—H), 6.92–7.17 (m, 3H, Ar—H), 8.08 (s, 1H, NH), 10.38 (s, 1H, NH).

Synthesis of 3-(4-iodobutyl)-6-(3-ethyl-4-methylanilino) uracil, Compound e (IB-EMAU)

Trimethylsilyl iodide (19.4 g, 47 mmol) was added to a stirred solution of 3-(4-hydroxybutyl)-6-(3-ethyl-4-methylanilino)uracil (7.7 g, 24.3 mmol) in dry chloroform (300 ml). The reaction mixture was stirred at reflux for 12 h, until disappearance of starting material (TLC). A saturated solution of aqueous sodium sulfite was added to decolorize the brown-purple solution. After separation of layers, the aqueous solution was extracted with chloroform, and the combined organic extracts were reduced to about one fourth volume. The solid was filtered and washed with water and acetone to give 9.9 g (95%) of IB-EMAU.

300 MHz $^1$H NMR (DMSO-$d_6$): δ1.14 (t, 3H, $CH_3CH_2Ar$), 1.54–1.78 (m, 4H, 2×$CH_2$), 2.24 (s, 3H, $CH_3Ar$), 2.57 (q, 2H, $CH_2Ar$), 3.29 (t, 2H, $CH_{21}$), 3.72 (t, 2H, $CH_2N$), 4.73 (s, 1H, $C_5$—H), 6.92–7.15 (m, 3H, Ar—H), 8.15 (s, 1H, NH), 10.45 (s, 1H, NH).

3-(4-Iodobutyl)-6-(3,4-dimethylanilino)uracil (IB-DMAU) was prepared by the same sequence. Yield: 92%.

300 MHz $^1$H NMR (DMSO-$d_6$): 10.45 (s, 1H), 8.12 (s, 1H), 7.16 (d, 1H), 7.0 (s, 1H), 6.93 (d, 1H), 4.72 (s, 1H), 3.72 (t, 2H), 3.31 (t, 2H), 2.21 (s, 3H), 2.2 (s, 3H), 1.73 (m, 2H), 1.58 (m, 2H) ppm.

3-(5-Iodopentyl)-6-(3-ethyl-4-methylanilino)uracil (IP-EMAU) was prepared by the same sequence. Yield: 90%.

300 MHz $^1$H NMR (DMSO-$d_6$): 10.38 (s, 1H), 8.08 (s, 1H), 7.15 (d, 1H), 6.98 (s, 1H), 6.93 (d, 1H), 4.72 (s, 1H), 3.67 (t, 2H), 3.25 (t, 2H), 2.57 (q, 2H), 2.22 (s, 3H), 1.77 (m, 2H), 1.48 (m, 2H) 1.30 (m, 2H), 1.12 (t, 3H) ppm.

Synthesis of Ethyl 1-cyclopropyl-14-dihydro-6,8-difluoro-4-oxo-7-(3-methylpiperazinyl)-quinoline-3-carboxylate for use in the Synthesis of Compounds (e.g. Compounds 70, Below)

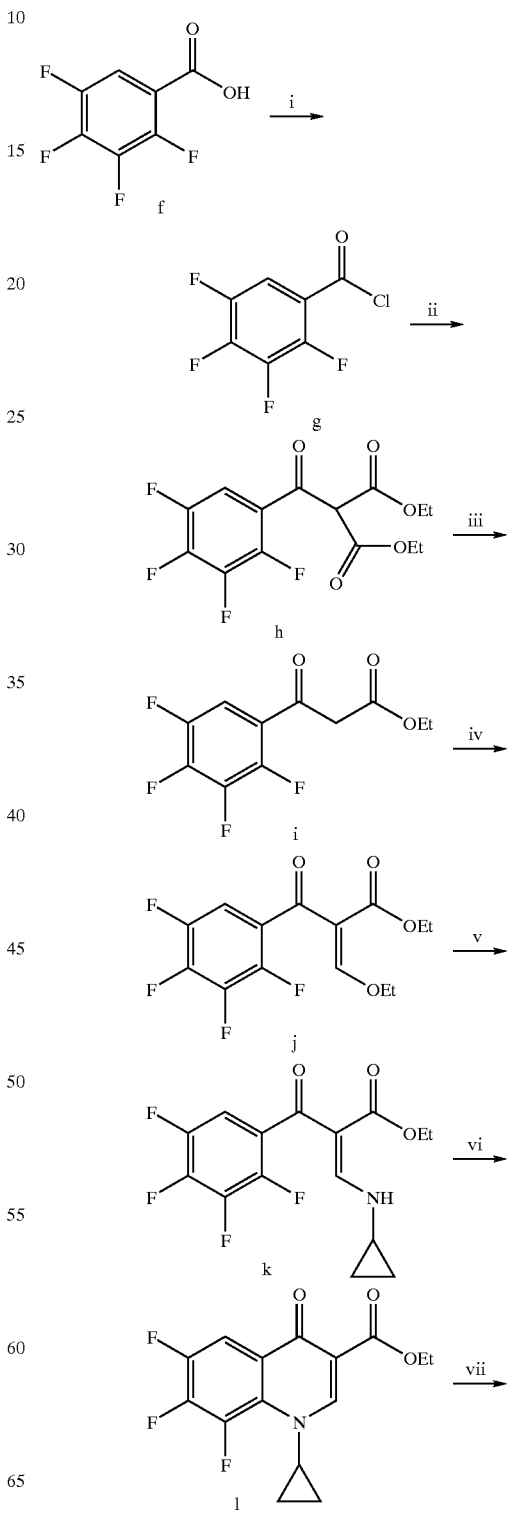

-continued

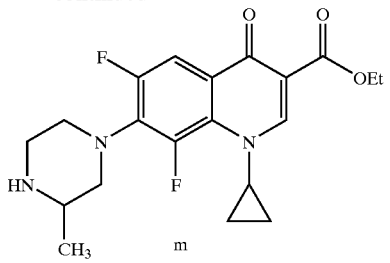

Synthesis of 2,3,4,5-tetrafluorobenzoyl Chloride, Compound g

To the solution of 2,3,4,5-tetrafluorobenzoic acid (compound f, 29.5 g, 150 mmol) in 200 ml THF, was added $SOCl_2$ 20 ml dropwise at 0° C., then the mixture was stirred at room temperature for 6 hours. After removal of the solvent and excessive $SOCl_2$, the residue was used for the next step directly.

Synthesis of diethyl 2,3,4,5-tetrafluorobenzoyl-malonate, Compound h

To magnesium ethoxide (13.5 g, 118 mmol) in 15 ml of absolute ethanol, was added diethyl malonate (18.9 g, 118 mmol) in 40 ml of anhydrous toluene dropwise at 50–60° C. The mixture was stirred for one more hour at this temperature, cooled to −10 to −5° C., and a solution of compound g (25 g, 118 mmol) in 10 ml absolute toluene was then slowly added. The mixture was stirred for one hour at 0 to −5° C. and allowed to reach room temperature overnight and into this mixture was poured a solution of 40 ml ice water and 3.5 ml 96% sulfuric acid while cooling with ice. The oil phase was separated and then extracted with toluene (100 ml×2). The combined toluene solution was washed with saturated NaCl solution, dried with $Na_2SO_4$, and the solvent was removed by rotavapor to obtain 35 g of crude product (yield 88%).

Synthesis of ethyl 2,3,4,5-tetrafluorobenzoylacetate, Compound i.

p-Toluenesulfonic acid (0.1 g) was added to 33.7 g of crude h in 50 ml of water. The mixture was refluxed for 5 hours with stirring. After cooling to room temperature, the reaction was extracted with methylene chloride (100 ml×3), the combined organic layer was washed with saturated NaCl solution and dried with $Na_2SO_4$. The solvent was then removed by rotavapor. The residue was further purified using chromatography ($CH_2Cl_2$:petroleum ether, 40:60 as eluent) to give 24 g of the product as a solid, yield 91%.

300 MHz $^1$H NMR ($CDCl_3$): 7.64 (m, 1H), 4.26 (q, 2H), 3.90 (s, 2H), 1.35 (t, 3H) ppm.

Synthesis of ethyl 2-(2,3,4,5-tertrafluorobenzoyl)-3-ethoxyacrylate, Compound j.

A mixture of compound i (22 g, 83 mmol), triethyl orthoformate (17 g, 115 mmol), and 20 g of acetic anhydride was heated at 150° C. with stirring for 2 hours. Removal of the solvent in vacuo gave the crude product for next step, yield 79%.

Synthesis of ethyl 2-(2,3,4,5-tertrafluorobenzoyl)-3-cyclopropylamine-acrylate, Compound k.

Cyclopropylamine (3.5 g, 67 mmol) was added dropwise to a solution of compound j (21 g, 66 mmol) in 30 ml of ethanol while cooling with ice-water and stirring, then stirring at room temperature for another two hours. The solvent was removed, and the residue was crystallized from cyclohexane-petroleum ether, 19.7 g of solid product was obtained, yield 87%.

300 MHz $^1$H NMR ($CDCl_3$): 10.95 (d, 1H), 8.18 (d, 1H), 7.86 (m, 1H), 4.15 (q, 2H), 3.88 (m, 1H), 1.21 (t, 3H), 0.95–0.84 (m, 4H) ppm.

Synthesis of ethyl 1-cyclopropyl-6,7,8-trifluoro-1,4-dihydro-4-oxoquinoline-3-carboxylate, Compound l.

Sodium fluoride (3.5 g, 83 mmol) was added to a solution of compound k (19.7 g, 60 mmol) in 50 ml DMF, and the mixture was stirred at reflux for 2 hours. After removal of most of DMF in vacuo, poured the residue into ice-water. The precipitate was filtered and washed thoroughly with water, dried in vacuo to give the product 17.5 g, yield 95%.

300 MHz $^1$H NMR ($CDCl_3$): 8.62 (s, 1H), 8.18 (t, 1H), 4.36 (q, 2H), 3.90 (m, 1H), 1.42 (t, 3H), 1.26–1.12 (m, 4H) ppm.

Synthesis of ethyl 1-cyclopropyl-1,4-dihydro-6,8-fluoro-4-oxo-7-(3-methylpiperazinyl)-quinoline-3-carboxylate, Compound m.

Compound 1 (311 mg, 1 mmol) was added to a solution of 2-methylpiperazine (500 mg, 5 mmol) in 50 ml DMSO, and the mixture was heated at 80° C. with stirring for 5 hours. The solvent was removed in vacuo, the residue was purified by chromatography on silica gel using $CHCl_3$/MeOH=95/5 as eluent to give 320 mg (yield: 82%) of compound m.

300 MHz $^1$H NMR ($CDCl_3$): 8.62 (s, 1H), 7.86 (d, 1H), 4.34 (q, 2H), 3.85 (m, 1H), 3.25 (m, 3H), 3.13–2.88 (m, 4H), 1.60 (s, 1H), 1.39 (t, 3H), 1.22–1.06 (m, 7H) ppm.

Methods for the synthesis of compounds EMAU and HB-EMAU have been described (see, e.g., Brown et al., *J. Med. Chem.*, 20: 1186–1189 (1977); U.S. Pat. No. 5,516, 905). The following synthetic protocols exemplify how representative compounds of the invention may be produced.

Compound 1

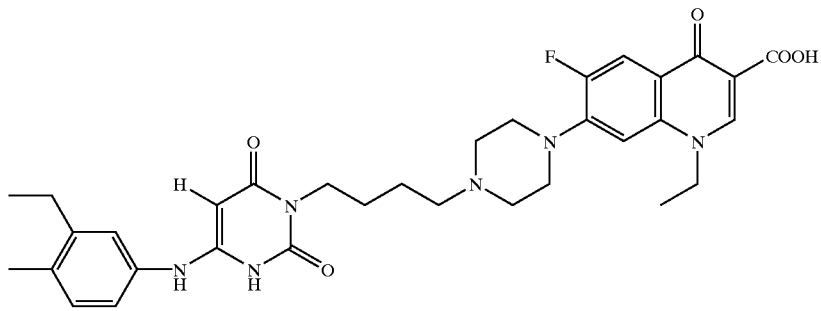

Method A:

A mixture of 3-(4-iodobutyl)-6-(3-ethyl-4-methylanilino) uracil (241 mg, 0.56 mmol), potassium carbonate (130 mg, 0.94 mmol) and norfloxacin (150 mg, 0.47 mmol) in N,N-dimethylformamide (20 ml) was stirred at room temperature overnight. The mixture was concentrated under reduced pressure, and the residue was purified by chromatography on silica gel using chloroform:methanol as eluent to give 180 mg of product (yield 62%) as a white solid.

300 MHz $^1$H NMR (DMSO-$d_6$): 15.31 (s, 1H, COOH), 10.37 (s, 1H, NH), 8.92 (s, 1H, FQ-$C_2$—H), 8.07 (s, 1H, NH), 7.91 (d, 1H, FQ-$C_5$—H), 6.90–7.23 (m, 4H, Ar—H and FQ-$C_8$—H), 4.71 (s, 1H, $C_5$—H), 4.57 (q, 2H, NCH$_2$), 3.72 (t, 2H, NCH$_2$), 3.30 (m, 4H, 2×CH$_2$N), 2.57 (m, 6H, 2×CH$_2$N and ArCH$_2$), 2.37 (m, 2H, CH$_2$N), 2.21 (s, 3H, ArCH$_3$), 1.37–1.58 (m, 7H, 2×CH$_2$ and CH$_3$), 1.12 (t, 3H, ArCH$_2$CH$_3$) ppm.

Method B: via 2-Propenyl Ester of Norfloxacin

1. A mixture of 2-propenyl 1-ethyl-1,4-dihydro-6-fluoro-4-oxo-7-piperazinylquinoline-3-carboxylate hydrochloride (0.85 g, 2.1 mmol), sodium bicarbonate (0.56 g, 6.7 mmol), and 3-(4-iodobutyl)-6-(3-ethyl-4-methylanilino) uracil (1.1 g, 2.6 mmol) in 60 ml of N,N-dimethylformamide was stirred at room temperature overnight. Water was added, and the mixture was extracted with chloroform, and the organic extracts dried over sodium sulfate. After removal of solvents, the residue was purified by chromatography on silica gel using chloroform:methanol (90:10–85:15) as eluent to give 877 mg of product (yield 62%) as a white solid. (The preparation of 2-propenyl 1-ethyl-1,4-dihydro-6-fluoro-4-oxo-7-piperazinylquinoline-3-carboxylate hydrochloride has been described (see, e.g., *J. Med. Chem.* 42: 3899–3909 (1999)).

2. The 2-propenyl ester (600 mg) was dissolved in 80 ml of a 4:1 mixture of methanol and water. Lithium hydroxide (53 mg) was added to the solution, and the mixture was stirred at room temperature overnight. The mixture was acidified with acetic acid to pH 5–6. The solvent was evaporated to dryness, and a small amount of water was added to the residue. The suspension was filtered and dried in vacuo to give 557 mg of 1 (yield 99%) as an off-white solid.

tography on silica gel using chloroform:methanol (7–15% methanol) as eluent to give 139 mg of product (yield 76%) as a white solid.

300 MHz $^1$H NMR (DMSO-$d_6$): 10.42 (s, 1H, NH), 8.30 (s, 1H, FQ-$C_2$—H), 8.12 (s, 1H, NH), 7.78 (d, 1H, FQ-$C_5$—H), 7.44 (d, 1H, FQ-$C_8$—H), 6.90–7.15 (m, 3H, Ar—H), 4.75 (s, 1H, $C_5$—H), 4.20 (q, 2H, CH$_2$O), 3.72 (m, 2H, NCH$_2$), 3.65 (m, 1H, CH), 3.22 (m, 4H, 2×CH$_2$N), 2.50–2.63 (m, 6H, 2×CH$_2$N and ArCH$_2$), 2.35 (m, 2H, NCH$_2$), 2.21 (s, 3H, ArCH$_3$), 1.38–1.60 (m, 4H, 2×CH$_2$), 1.20–1.30 (m, 5H, CH$_2$ and CH$_3$), 1.05–1.17 (m, 5H, CH$_2$ and ArCH$_2$CH$_3$) ppm.

2. The ethyl ester (100 mg) was dissolved in 50 ml of a 4:1 mixture of methanol and water. Lithium hydroxide (40 mg) was added to the solution, and the mixture was stirred at room temperature overnight. After acidification of the mixture with acetic acid to pH 5–6, the solvent was evaporated to dryness, and a small amount of water was added. The suspension was filtered and dried in vacuo to give 87 mg of product (yield 91%) as an off-white solid.

300 MHz $^1$H NMR (DMSO-$d_6$): 15.18 (s, 1H, COOH), 10.37 (s, 1H, NH), 8.65 (s, 1H, FQ-$C_2$—H), 8.05 (s, 1H, NH), 7.90 (d, 1H, FQ-$C_5$—H), 7.56 (s, 1H, FQ-$C_8$—H), 6.90–7.17 (m, 3H, Ar—H), 4.71 (s, 1H, $C_5$—H), 3.83 (m, 1H, CH), 3.72 (m, 2H, NCH$_2$), 3.30 (m, 4H, 2×CH$_2$N), 2.57 (m, 6H, 2×CH$_2$N and ArCH$_2$), 2.37 (m, 2H, CH$_2$N), 2.21 (s, 3H, ArCH$_3$), 1.40–1.61 (m, 4H, 2×CH$_2$), 1.32 (m, 2H, CH$_2$), 1.10–1.28 (m, 5H, CH$_2$ and CH$_3$) ppm.

Compound 10, the Methanesulfonate Salt of Compound 2

Methanesulfonic acid (0.2 ml) was added to a solution of 215 mg of Compound 2 in 40 ml of N,N-dimethylformamide. The mixture was stirred at room temperature overnight. The solvent was removed under reduced pressure, and the residue was triturated with tetrahydrofuran. The solid was filtered, washed with anhydrous diethyl ether, and dried to give 240 mg (97%) of mesylate salt of Compound 2 as a yellow solid.

300 MHz $^1$H NMR (DMSO-$d_6$): 10.48 (s, 1H, NH), 9.52 (s, 1H, COOH), 8.68 (s, 1H, FQ-$C_2$-H), 8.21 (s, 1H, NH), 7.94 (d, 1H, FQ-$C_5$—H), 7.60 (FQ-$C_8$—H), 6.90–7.15 (m, 3H, Ar—H), 5.90 (br, 1H, SO$_3$H), 4.72 (s, 1H, $C_5$—H), 3.87 (m, 2H, NCH$_2$), 3.75 (m, 1H, CH), 3.60 (m, 2H, CH$_2$N),

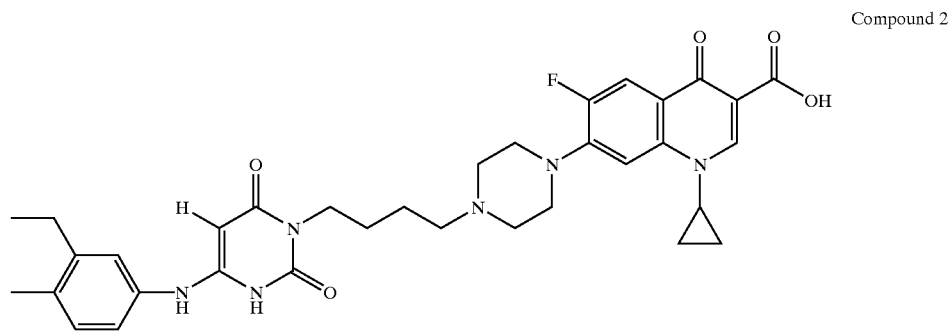

Compound 2

1. A mixture of ethyl 1-cyclopropyl-1,4-dihydro-6-fluoro-4-oxo-7-piperazinylquinoline-3-carboxylate (100 mg, 0.28 mmol), sodium bicarbonate (74 mg, 0.88 mmol), and 3-(4-iodobutyl)-6-(3-ethyl-4-methylanilino)uracil (184 mg, 0.43 mmol) in 30 ml of N,N-dimethylformamide was stirred at room temperature overnight. Water was added, and the mixture was extracted with chloroform. The organic extracts were dried over sodium sulfate, and, after removal of solvents, the residue was purified by chroma- 3.26 (m, 4H, 2×CH$_2$N), 2.57 (q, 2H, ArCH$_2$), 2.32 (m, 4H, 2×CH$_2$N), 2.21 (s, 3H, ArCH$_3$), 1.50–1.70 (m, 4H, 2×CH$_2$), 1.30 (m, 2H, CH$_2$), 1.20 (m, 2H, CH$_2$), 1.12 (t, 3H, ArCH$_2$CH$_3$) ppm.

Compound 21, the Hydrochloride Salt of Compound 2

A solution of 4.0 M hydrogen chloride in dioxane was added to a solution of Compound 2 in N,N-dimethylformamide. The mixture was stirred at room temperature for 1 h. The solvent was removed to give the hydrochloride of Compound 2 in quantitative yield as a yellow solid.

1,4-dihydro-6-fluoro-4-oxoquinolin-7-piperazinyl-heptyl)pyrimidin-4(3H)-one (yield 74%) as a white solid.

Compound 12

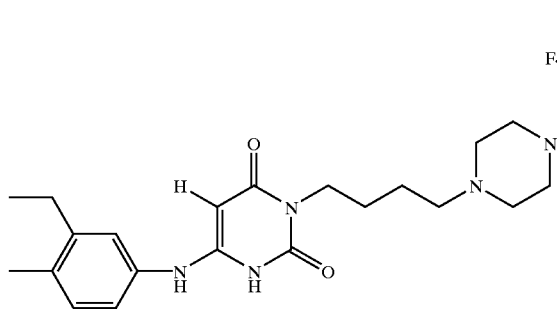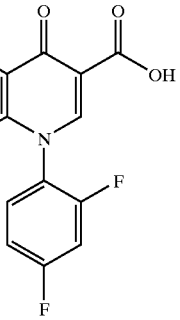

This compound was made by an essentially identical method for the preparation of Compound 2, starting with ethyl 1-(2,4-difluorophenyl)-1,4-dihydro-6-fluoro-4-oxo-7-piperazinylquinoline-3-carboxylate.

300 MHz $^1$H NMR (DMSO-$d_6$): 15.02 (s, 1H, COOH), 10.35 (s, 1H, NH), 8.86 (s, 1H, FQ-$C_2$—H), 8.10 (s, 1H, NH), 7.88 (m, 2H), 7.65 (t, 1H), 7.43 (t, 1H), 6.86–7.14 (m, 3H, Ar—H), 6.20 (d, 1H), 4.72 (s, 1H, $C_5$—H), 3.68 (t, 2H, CH$_2$N), 3.50 (m, 2H, NCH$_2$), 2.95 (m, 4H, 2×CH$_2$N), 2.55 (q, 2H, CH$_2$), 2.38 (m, 4H, 2×CH$_2$N), 2.16 (s, 3H, ArCH$_3$), 1.44 (m, 4H, 2×CH$_2$), 1.12 (t, 3H, CH$_3$) ppm.

2. A mixture of the above intermediate (120 mg, 0.2 mmol), 3-ethyl-4-methylaniline hydrochloride (52 mg, 0.3 mmol), and a few drops of 3-ethyl-4-methylaniline was heated at 160° C. for 30 minutes. After cooling to room temperature water (15 ml) was added to the residue, and the mixture was extracted with chloroform (3×40 ml). The combined organic layers were dried over anhydrous magnesium sulfate. The solvent was removed under reduced pressure, and the residue was purified by chromatography Compound 8

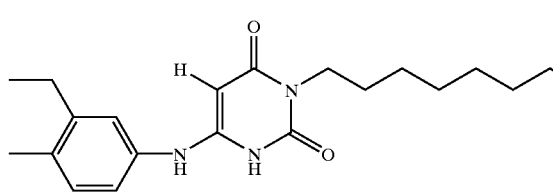

1. A mixture of ethyl 1-cyclopropyl-1,4-dihydro-6-fluoro-4-oxo-7-piperazinylquinoline-3-carboxylate (139 mg, 0.39 mmol), potassium carbonate (150 mg, 1.08 mmol), sodium iodide (200 mg) and 6-amino-2-methoxy-3-(7-bromoheptyl)-4-pyrimidone (161 mg, 0.51 mmol) in 60 ml of acetonitrile was heated at reflux until the completion of reaction (ca. 24 h). Water was added, and the mixture was extracted with chloroform. The organic extracts were dried over sodium sulfate, and after removal of solvents, the residue was purified by chromatography on silica gel using chloroform:methanol (90:10) as eluent to give 171 mg of 6-amino-2-methoxy-3-(3-carboxy-1-cyclopropylon silica gel with chloroform:methanol (90:10) as eluent, to give 62 mg (44% yield) of the ethyl ester of the product.

3. The ethyl ester of the product (45 mg) was dissolved in 40 ml of a 4:1 mixture of methanol and water. Lithium hydroxide (40 mg) was added to the solution, and the mixture was stirred at room temperature overnight. After acidification of the mixture with acetic acid to pH 5–6, the solvent was evaporated to dryness, and a small amount of water was added to the residue. The suspension was filtered and the solid was dried in vacuo to give 40 mg of Compound 8 (yield 92.6%) as an off-white solid.

Compound 7

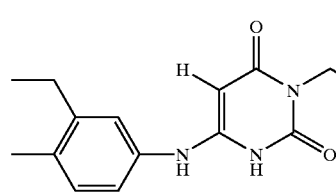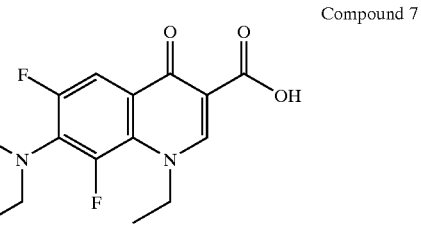

1. A solution of 3-[4-(1-piperazinyl)butyl]-6-(3-ethyl-4-methylanilino)uracil dihydrochloride (1.2 eq), ethyl 1-ethyl-6,7,8-trifluoro-4-quinolone-3-carboxylate (1 eq), and potassium carbonate (4.0 eq) in acetonitrile was heated at reflux overnight (ca. 16 hours). The solvent was evaporated, and the residue chromatographed on silica gel, with chloroform:methanol as eluent, giving ca. 40% of the ester intermediate. $^1$H NMR used to confirm structure.
2. The ester was stirred in a solution of sodium hydroxide in methanol:water at room temperature. After evaporation of methanol, the solution was acidified with acetic acid. The colorless precipitate was filtered and washed with water to give ca. 90% of product.

300 MHz $^1$H NMR (DMSO-$d_6$): 14.82 (s, 1H, COOH), 10.40 (s, 1H, NH), 8.90 (s, 1H, FQ-$C_2$—H), 8.02 (s, 1H, NH), 7.89 (d, 1H, FQ-$C_5$—H), 6.85–7.14 (m, 3H, Ar—H), 4.72 (s, 1H, $C_5$—H), 4.61 (m, 2H, $CH_2$), 3.83 (m, 2H, $NCH_2$), 3.42 (m, 6H, 3×$CH_2N$), 2.57 (q, 2H, $CH_2$), 2.33 (m, 4H, 2×$CH_2N$), 2.17 (s, 3H, $ArCH_3$), 1.54 (m, 7H, 2×$CH_2$ and $CH_3$), 1.10 (t, 3H, $CH_3$) ppm.

This compound was made by an essentially identical method as described for Compound 7, starting with ethyl 1-ethyl-6-fluoro-7-chloro-8-aza-4-quinolone-3-carboxylate.

300 MHz $^1$H NMR (DMSO-$d_6$): 15.20 (s, 1H, COOH), 10.38 (s, 1H, NH), 8.86 (s, 1H, FQ-$C_2$—H), 8.06 (s, 2H), 6.85–7.14 (m, 3H, Ar—H), 4.72 (s, 1H, $C_5$—H), 4.55 (m, 2H, $CH_2$), 3.88 (m, 4H, 2×$NCH_2$), 3.50 (m, 2H, $CH_2N$), 3.30 (m, 2H, $CH_2N$), 2.55 (q, 2H, $CH_2$), 2.34 (m, 4H, 2×$CH_2N$), 2.15 (s, 3H, $ArCH_3$), 1.56 (m, 7H, 2×$CH_2$ and $CH_3$), 1.10 (t, 3H, $CH_3$) ppm.

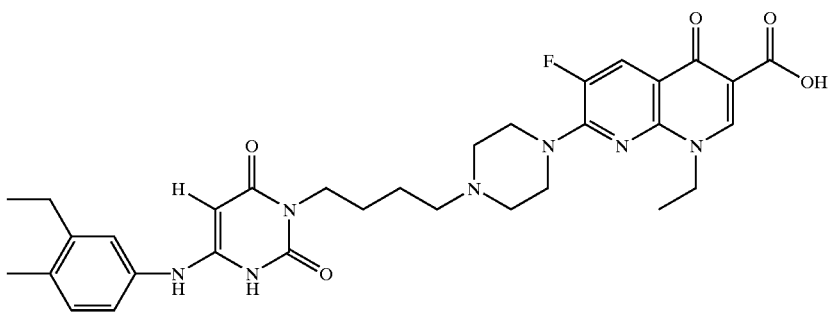

Compound 6

Compound 70

A schematic diagram of the synthesis of Compound 70 is shown below.

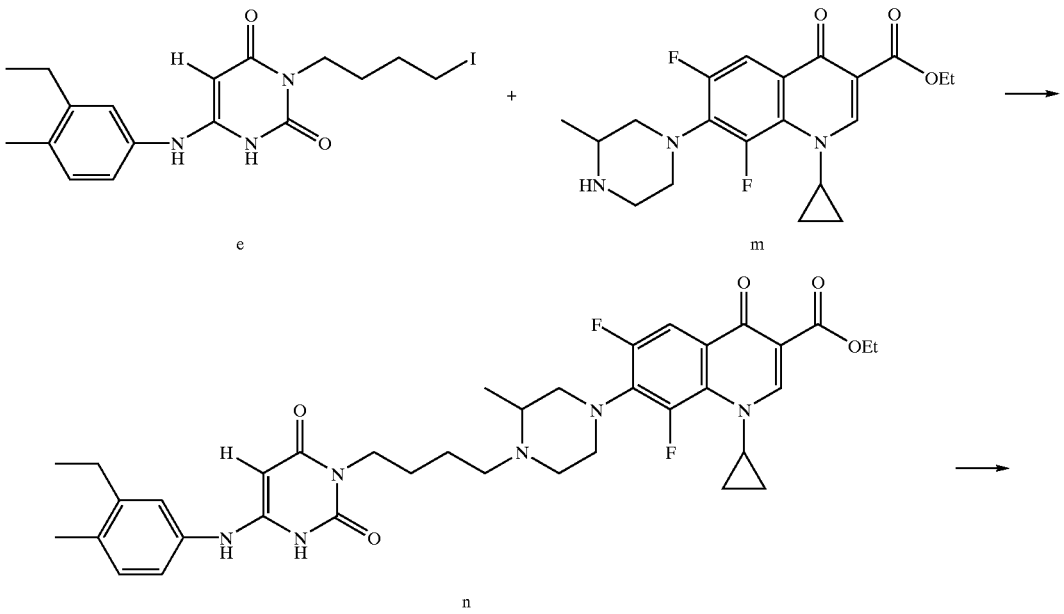

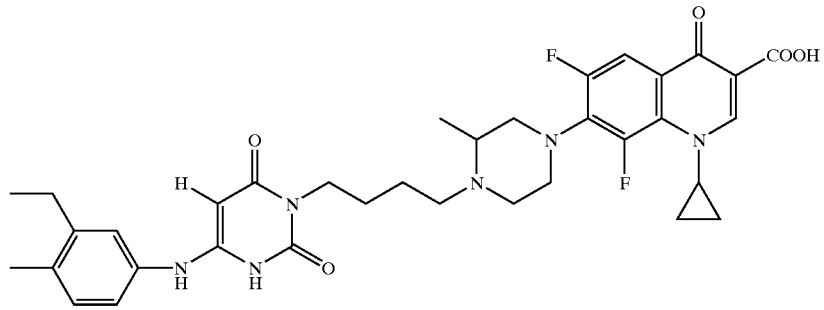

70

Synthesis of Compound n

A mixture of ethyl 1-cyclopropyl-1,4-dihydro-6,8-fluoro-4-oxo-7-(3-methylpiperazinyl)-quinoline-3-carboxylate (compound m, 320 mg, 0.82 mmol), sodium bicarbonate (414 mg, 3 mmol), and 3-(4-iodobutyl)-6-(3-ethyl-4-methylanilino)uracil (compound e, 580 mg, 1.36 mmol) in 50 ml DMF was stirred at room temperature overnight. Water was added, and the mixture extracted with chloroform, and then dried over $Na_2SO_4$. After removal of solvents, the residue was purified by chromatography on silica gel using $CHCl_3/MeOH$ (7–15% methanol in chloroform) as eluent to give 196 mg of compound n (Yield: 35%) as a white solid.

300 MHz $^1H$ NMR (DMSO-$d_6$): 10.48 (s, 1H), 8.52 (s, 1H), 8.05 (s, 1H), 7.78 (d, 1H), 6.86–7.15 (m, 3H), 4.78 (s, 1H), 4.17 (q, 2H), 3.90(m, 1H), 3.72 (m, 3H), 3.32 (m, 4H), 2.70–2.93 (m, 2H), 2.54 (q, 2H), 2.35 (m, 2H), 2.12 (s, 3H), 1.38–1.60 (m, 4H), 0.95–1.30 (m, 13H) ppm.

Synthesis of Compound 70

Compound n (85 mg, 0.12 mmol) was dissolved in a 30 ml 4:1 mixture of methanol and water. 40 mg (0.95 mmol) of lithium hydroxide was added to the solution and the mixture was stirred at room temperature overnight. The mixtures was then neutralized with acetic acid to pH 5–6. The solvent was evaporated to dryness and a small amount of water was added. The suspension was filtered and dried in vacuo to give 72 mg (89%) of Compound 70 as an off-white solid.

300 MHz $^1H$ NMR (DMSO-$d_6$): 15.20 (s, 1H), 10.36 (s, 1H), 8.72 (s, 1H), 8.50 (s, 1H), 7.82 (d, 1H), 6.86–7.15 (m, 3H), 4.78 (s, 1H), 4.12 (m, 1H), 3.74 (m, 2H), 3.33 (m, 4H), 2.90 (m, 2H), 2.12 (s, 3H), 1.40–1.61 (m, 4H), 0.95–1.22 (m, 10H, $CH_2$) ppm.

2,8-Diazabicyclo[4.3.0] nonane (diamine B1) was prepared using methods known in the art (see, e.g., PCT publication WO 94/15938). A mixture of 7-chloro-1-ethyl-6-fluoro-4-oxo-quinoline-3-carboxylic acid (A1) (270 mg, 1 mmol), B1 trifluoroacetate salt (360 mg, 1 mmol,) and 1,4-diazabicyclo[5.4.0]undec-7-ene (DBU) (0.45 ml, 3 mmol) in 1-methyl-2-pyrrolidinone (3 ml) was heated at 120° C. overnight. The solvent was removed and the residue was purified by preparative HPLC (25% to 50% acetonitrile: water) to obtain 91 mg (yield 26%) of A1B1.

A mixture of the above intermediate (50 mg, 0.14 mmol), 3-(4-iodopentyl)-6-(3-ethyl-4-methylanilino)uracil (60 mg, 0.14 mmol) and potassium carbonate (60 mg, 0.43 mmol) in N,N-dimethylformamide (2 ml) was heated at 90° C. for 2 hours. After removal of solvent, the residue was purified by preparative HPLC (25% to 50% acetonitrile:water) to obtain 17 mg (yield 10%) of Compound 80 as the trifluoroacetate.

400 MHz $^1H$ NMR (DMSO-$d_6$): 10.94 (s, 1H, NH), 10.34 (s, 1H, $NH^+CF3COO^-$), 9.59 (s, 1H, $NH^+CF_3COO^-$), 9.32 (s, 1H, NH), 8.66 (s, 1H, FQ-$C_2$—H), 8.32 (d, 1H, FQ-$C_5$—H), 7.56 (dd, 1H, Ar—H), 7.34–7.39 (m, 2H, FQ-C8-H and Ar—H), 7.16 (m, 1H, Ar—H), 5.15 (s, 1H, $C_5$—H), 4.97 (m, 4H, 2$CH_2$N), 3.29–4.65 (m, 9H, 4$CH_2$N and 1CHN), 3.0 (q, 2H, Ar—$CH_2CH_3$), 2.66 (s, 3H, Ar—$CH_3$), 1.84–2.22 (m, 3$CH_2$ and CH), 1.73 (m, 2H, $CH_2$), 1.56 (t, 3H, Ar—$CH_2CH_3$) ppm.

Compound 80

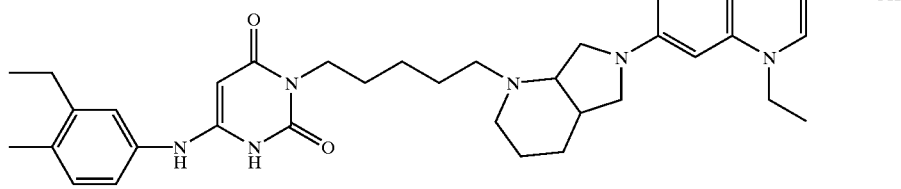

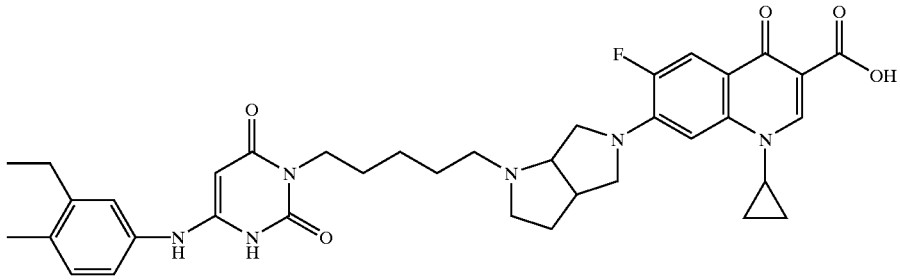

Compound 81

2,7-Diazabicyclo[3.3.0]octane (diamine B2) was prepared using methods known in the art (see, e.g., EP 0 393 424 B1). A mixture of 7-chloro-1-cyclopropyl-6-fluoro-4-oxo-quinoline-3-carboxylic acid (A2) (195 mg, 0.694 mmol), diamine B2 dihydrochloride (128 mg, 0.692 mmol), and DBU (0.31 ml, 2.073 mmol) in 1-methyl-2-pyrrolidinone (2 ml) was heated at 120° C. overnight. The solvent was removed, and the residue was purified by preparative HPLC (25% to 50% acetonitrile:water) to obtain 21.1 mg (yield 10%) of A2B2 trifluoroacetate.

A mixture of the above intermediate (15.2 mg, 0.032 mmol), 3-(4-iodopentyl)-6-(3-ethyl-4-methylanilino)uracil (14.2 mg, 0.032 mmol) and potassium carbonate (15 mg, 0.1 mmol) in N,N-dimethylformamide (2 ml) was heated at 90° C. for 4 hours. An additional equivalent of 3-(4-iodopentyl)-6-(3-ethyl-4-methylanilino)uracil (14 mg) was added and the mixture was heated at 110° C. for 2 hours. After removal of solvent, the residue was purified by preparative HPLC (30% to 60% acetonitrile:water) to obtain 2.7 mg (yield 9%) of Compound 81 as the trifluoroacetate salt.

400 MHz $^1$H NMR (DMSO-$d_6$): 10.43 (s, 1H, NH), 9.63 (s, 1H, NH), 8.57 (s, 1H, FQ-$C_2$-H), 8.01 (s, 1H, NH$^+$CF$_3$COO$^-$), 7.84 (d, 1H, FQ-$C_5$—H), 7.19 (d, 1H, FQ-$C_8$—H), 7.07 (d, 1H, Ar—H), 6.87 (m, 2H, Ar—H), 4.66 (s, 1H, $C_5$—H), 4.16 (m, 1H, NCH), 4.05 (d, 1H, NCH), 3.43–3.70 (m, 10H, 5*CH$_2$N), 2.38–2.51 (m, 4H, Ar—CH$_2$CH$_3$ and CH$_2$), 2.17 (s, 3H, Ar—CH$_3$), 1.79 (m, 1H, CH), 1.62 (m, 2H, CH$_2$), 1.48 (m, 2H, CH$_2$), 1.25 (m, 4H, 2CH$_2$), 1.06 (m, 5H, CH$_2$ and Ar—CH$_2$CH$_3$) ppm.

A mixture of A2 (360 mg, 1.28 mmol), diamine B1 trifluoroacetate (450 mg, 1.27 mmol) and DBU (0.6 ml, 3.84 mmol) in 1-methyl-2-pyrrolidinone (3 ml) was heated at 120° C. overnight. The solvent was removed and the residue was purified by preparative HPLC (25% to 50% acetonitrile:water) to obtain 161 mg (yield 34%) of A2B1 trifluoroacetate salt.

A mixture of the above intermediate (55.4 mg, 0.113 mmol), 3-(4-iodopentyl)-6-(3-ethyl-4-methylanilino)uracil (50 mg, 0.113 mmol) and potassium carbonate (50 mg, 0.36 mmol) in N,N-dimethylformamide (2 ml) was heated at 90° C. for 1 hour. After removal of solvent, the residue was purified by preparative HPLC (25% to 50% acetonitrile:water) to obtain 15.6 mg (yield 20%) of Compound 82 as the trifluoroacetate salt.

400 MHz $^1$H NMR (DMSO-$d_6$): 11.06 (s, 1H, NH), 10.46 (s, 1H, NH$^+$CF3COO$^-$), 9.72 (s, 1H, NH$^+$CF3COO$^-$), 9.16 (s, 1H, NH), 8.77 (s, 1H, FQ-$C_2$—H), 8.41 (d,1H, FQ-$C_5$—H), 7.71 (m, 2H, FQ-$C_8$—H and Ar—H), 7.49 (m, 2H, Ar—H), 5.27 (s, 1H, $C_5$—H), 3.44–4.79 (m, 12H, 5CH$_2$N and 2CHN), 3.13 (q, 2H, Ar—CH$_2$CH$_3$), 2.79 (s, 3H, Ar—CH$_3$), 2.35 (m, 6H, 3*CH$_2$), 2.09 (m, 2H, CH$_2$), 1.86 (m, 5H, 2*CH$_2$ and CH), 1.68 (m, 5H, CH$_2$ and Ar—CH$_2$CH$_3$) ppm.

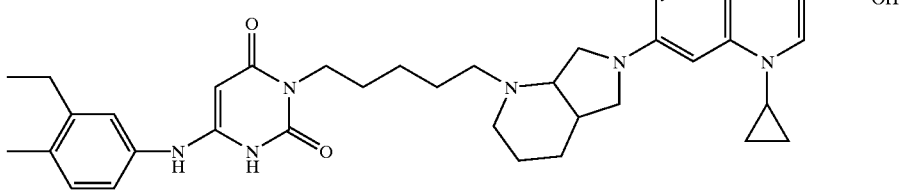

Compound 82

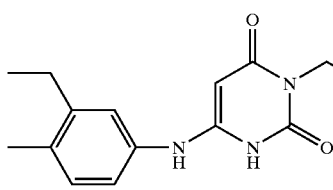
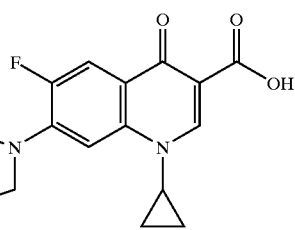

Compound 83

A mixture of ethyl 1-cyclopropyl-7,8-difluoro-4-quinolone-3-carboxylate (A3) (100 mg, 0.34 mmol) and 3-aminopyrrolidine (32 mg, 0.38 mmol) in dimethylsulfoxide (1 ml) was heated at 90° C. for 2 hours. The solvent was removed and the residue was purified by flash chromatography using dichloromethane:methanol (gradient from 99:1 to 80:20) as eluent to give 110 mg (yield 91%) of A3B3.

To a solution of the above intermediate (50 mg, 0.139 mmol) in N,N-dimethylformamide (1 ml) was added sodium hydride (4 mg, 0.167 mmol). After stirring for twenty minutes at room temperature, 3-(4-iodopentyl)-6-(3-ethyl-4-methylanilino)uracil (74 mg, 0.167 mmol) was added. The mixture was stirred at 100° C. for 3 hours. The solvent was removed and the residue was purified by flash chromatography using chloroform:methanol (gradient from 95:5 to 50:50) as eluent to give 33.6 mg of the ester intermediate (yield 36%).

The ester intermediate (33 mg, 0.049 mmol) was dissolved in methanol (1.6 ml). A solution of sodium hydroxide (20 mg) in water (0.4 ml) was added, and the mixture was stirred at room temperature overnight. The residue was separated by flash chromatography using ethanol:water::aqueous ammonia (gradient from 90:5:5 to 80:10:10), and the product fraction was purified by preparative HPLC (25% to 50% acetonitrile:$H_2O$) to obtain 3.6 mg (yield 11%) of Compound 83 trifluoroacetate as a yellow powder.

400 MHz $^1$H NMR (DMSO-$d_6$): 11.05 (s, 1H, NH), 9.23 (s, 2H, NH and $NH^+CF3COO^-$), 9.19 (s, 1H, FQ-$C_2$—H), 8.76 (s, 1H, NH), 8.47 (d, 1H, FQ-$C_5$—H), 7.72 (m, 2H, FQ-$C_8$—H and Ar—H), 7.68 (m, 2H, Ar—H), 5.29 (s, 1H, $C_5$—H), 4.53 (m, 2H, 2*NCH), 4.26–4.34 (m, 6H, 3*$CH_2$N), 3.60 (m, 2H, $CH_2$N), 2.89–3.01 (m, 4H, $CH_2$ and Ar—$CH_2CH_3$), 2.81 (s, 3H, Ar—$CH_3$), 2.21 (m, 2H, $CH_2$), 2.11 (m, 2H, $CH_2$), 1.88 (m, 4H, 2*$CH_2$), 1.7 (m, 5H, $CH_2$ and Ar—$CH_2CH_3$) ppm.

cis-2-Oxa-5,8-diazabicyclo[4,3-0]nonane (diamine 14) dihydrochloride was prepared using methods known in the art (see, e.g., U.S. Pat. No. 5,468,742). A mixture of A3 (0.25 g, 0.85 mmol), diamine B4 (0.18 g, 0.93 mmol) and DBU in N,N-dimethylformamide (5 ml) was heated at 95° C. for 5 hours. The solvent was removed and the residue was crystallized from methanol-ether to give 0.24 g (yield 70%) of A3B4 as a white solid.

A mixture of the above intermediate (0.1 g, 0.24 mmol), 3-(4-iodopentyl)-6-(3-ethyl-4-methylanilino)uracil (0.13 g, 0.29 mmol) and potassium carbonate (51.6 mg, 0.37 mmol) in N,N-dimethylformamide (2 ml) was heated at 90° C. for 3 hours. Water was added, the mixture was extracted with dichloromethane, and the organic extracts were dried over sodium sulfate. After removal of solvents, the residue was purified by chromatography on silica gel using dichloromethane:methanol (gradient 98:2–90:10) as eluent to give 15 mg (yield 10%) of the ester.

The ester intermediate (15 mg, 0.02 mmol) was dissolved in methanol (0.5 ml). Aqueous 2N sodium hydroxide (1 ml) was added to the solution, and the mixture was stirred at room temperature for 5 hours. After evaporation of methanol under reduced pressure, the mixture was acidified with acetic acid to pH 5–6. The suspension was filtered, the solid washed with water and dried in vacuo to give 12 mg of a yellow solid which was purified by preparative HPLC (30% to 50% acetonitrile:water) to give 8 mg (yield 55%) of Compound 84 as the trifluoroacetate.

400 MHz $^1$H NMR (DMSO-$d_6$): 10.39 (s, 1H, NH), 8.53 (s, 1H, FQ-$C_2$—H), 8.08 (s, 1H, NH), 7.80 (d, 1H, FQ-$C_5$—H), 7.07 (m, 2H, FQ-$C_8$—H and Ar—H), 6.87 (m, 2H, Ar—H), 4.64 (s, 1H, $C_5$—H), 4.1 (m, 1H, CHN), 3.0–4.0 (m, 12H, 4$CH_2$N, 1$CH_2$O and 2CHN), 2.53 (q, 2H, Ar—$CH_2CH_3$), 2.35 (m, 2H, $CH_2$N), 2.17 (s, 3H, Ar—$CH_3$), 1.17–2.1 (m, 10H, 5$CH_2$), 1.1 (t, 3H, Ar—$CH_2CH_3$)

Compound 84

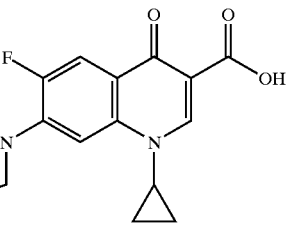
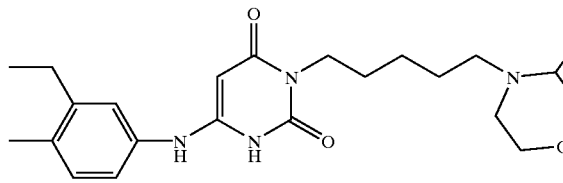

Compound 85

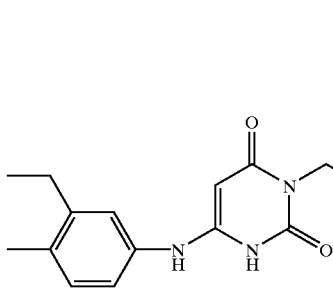 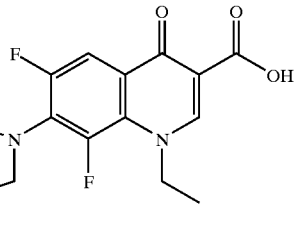

A mixture of A4 (0.15 g, 0.5 mmol), diamine B4 dihydrochloride (0.11 g, 0.55 mmol) and DBU (0.18 g, 1.6 mmol) in N,N-dimethylformamide (3 ml) was heated at 95° C. overnight. The solvent was removed in vacuo, and the residue was purified by flash chromatography on silica gel using dichloromethane:methanol (95:5–90:10–85:15) as eluent to give 0.13 g of product which was purified a second time by preparative TLC using dichloromethane:methanol (85:15) as eluent to give 60 mg (yield 30%) of A4B4.

A mixture of the above intermediate (60 mg, 0.14 mmol), 3-(4-iodopentyl)-6-(3-ethyl-4-methylanilino)uracil (78 mg, 0.17 mmol) and potassium carbonate (30.5 mg, 0.22 mmol) in N,N-dimethylformamide (2 ml) was heated at 90° C. overnight. The solvent was removed and the residue was purified by preparative TLC using dichloromethane: methanol (85:15) as eluent to give 15 mg (yield 25%) of the ester intermediate.

The ester (15 mg, 0.02 mmol) was dissolved in methanol (0.5 ml). Aqueous 2N sodium hydroxide (0.5 ml) was added to the solution, and the mixture was stirred at room temperature for 5 hours. After evaporation of methanol under reduced pressure, the mixture was acidified with acetic acid to pH 5–6. The suspension was filtered, the solid washed with water and dried in vacuo to give 10 mg (yield 70%) of Compound 85.

400 MHz $^1$H NMR (DMSO-$d_6$):10.35 (s, 1H, NH), 8.83 (s, 1H, FQ-$C_2$—H), 8.06 (s, 1H, NH), 7.74 (d, 1H, FQ-$C_5$—H), 7.11 (m, 2H, FQ-$C_8$—H and Ar—H), 6.91 (m, 2H, Ar—H), 4.69 (s, 1H, $C_5$—H), 4.52 (m, 2H, $CH_2N$), 4.02 (m, 5H, 2$CH_2N$ and 1CHN), 3.78 (m, 1H, 1CHO), 3.66 (m, 2H, $CH_2N$), 2.52 (q, 2H, Ar—$CH_2CH_3$), 2.21 (s, 3H, Ar—$CH_3$), 1.47 (m, 2H, $CH_2$), 1.40(t, 3H, $CH_3$), 1.11 (m, 5H, $CH_2$ and Ar—$CH_2CH_3$) ppm.

3,7-Diazabicyclo[3.3.0]octane (diamine B5) dihydrobromide was prepared from 3,7-diazabicyclo[4,3-0]oct-1(5)-ene dihydrobromide using methods known in the art (see, e.g., *Heterocycles*, 41(6): 1291–1298 (1995)). 3,7-diazabicyclo[4,3-0]oct-1(5)-ene dihydrobromide (0.2 g, 0.73 mmol) was hydrogenated in 50 ml of ethanol containing 75 mg of palladium (10% on activated carbon) at room temperature under 1 atmosphere of hydrogen for 2 hours. The catalyst was removed by filtration, and the filtrate was concentrated to give 0.18 g (yield 90%) of diamine B5 dihydrobromide as a beige solid.

A mixture of A3 (0.13 g, 0.45 mmol), B5 dihydrobromide (0.13 g, 0.47 mmol) and DBU (0.24 ml, 1.64 mmol) in acetonitrile (5 ml) was heated at reflux for 8 hours. The solvent was removed, and the residue was purified by flash chromatography on silica gel using dichloromethane:methanol:aqueous ammonia (98:1:1–95:4:1–90:9:1) as eluent to give 98 mg (yield 58%) of A3B5.

A mixture of A3B5 (95 mg, 0.24 mmol), 3-(4-iodopentyl)-6-(3-ethyl-4-methylanilino)uracil (0.12 g, 0.27 mmol) and potassium carbonate (68 mg, 0.49 mmol) in N,N-dimethylformamide (5 ml) was stirred at room temperature overnight. The solvent was removed and the residue was purified by flash chromatography on silica gel using dichloromethane: methanol: aqueous ammonia (98:1:1–95: 4:1–90: 9:1) to obtain 70 mg (yield 40%) of ester.

The above ester (21 mg, 0.03 mmol) was dissolved in methanol (1 ml). Aqueous 2N sodium hydroxide (2 ml) was added to the solution, and the mixture was stirred at room temperature for 5 hours. After evaporation of methanol under reduced pressure, the mixture was acidified with acetic acid to pH 5–6. The suspension was filtered, washed with water and acetonitrile, and purified by flash chromatography on silica gel using dichloromethane:methanol:aqueous ammonia (gradient from 90:9:1 to 85:14:1) as eluent to give 7 mg (yield 35%) of Compound 86.

400 MHz $^1$H NMR (DMSO-$d_6$): 8.57 (s, 1H, FQ-$C_2$—H), 8.27 (s, 1H, NH), 7.82 (d, 1H, FQ-$C_5$—H), 7.66 (m, 1H,

Compound 86

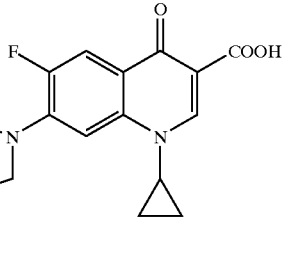

FQ-$C_8$—H), 7.09–7.17 (m, 2H, Ar—H), 6.89 (m, 1H, Ar—H), 4.68 (s, 1H, $C_5$H), 4.17 (t, 2H, $CH_2N$), 3.72 (m, 5H, 2*$CH_2N$ and CHN), 3.63 (t, 2H, $CH_2N$), 3.47 (m, 2H, $CH_2N$), 2.96 (m, 4H, 2*$CH_2N$), 2.54 (q, 2H, Ar—$CH_2CH_3$), 2.20(s, 3H, Ar—CH₃), 1.61(m, 2H, CH₂), 1.45(m, 4H, 2*CH₂), 1.20–1.31(m, 6H, 2*CH₂ and 2*CH), 1.11(t, 3H, Ar—CH₂CH₃) ppm.

A mixture of A3B4 (60 mg, 0.15 mmol), 3-(4-iodobutyl)-6-(3-ethyl-4-methyl anilino)uracil (70.2 mg, 0.16 mmol) and potassium carbonate (27 mg, 0.19 mmol) in N,N-dimethylformamide (2 ml) was heated at 80° C. for 2 hours. An additional equivalent of 3-(4-iodobutyl)-6-(3-ethyl-4-methylanilino)uracil was added and the mixture was heated at 80° C. for an additionnal 3 hours. After removal of solvent, the residue was purified by preparative TLC using dichloromethane:methanol (85:15) as eluent to give 12 mg (yield 12%) of ester.

The ester (12 mg, 0.017 mmol) was dissolved in methanol (0.5 ml). Aqueous 2N sodium hydroxide (1 ml) was added to the solution, and the mixture was stirred at room temperature for 5 hours. After evaporation of methanol under reduced pressure, the mixture was acidified with acetic acid to pH 5–6. The suspension was filtered, washed with water and acetonitrile and dried in vacuo to give 9 mg (yield 80%) of Compound 87.

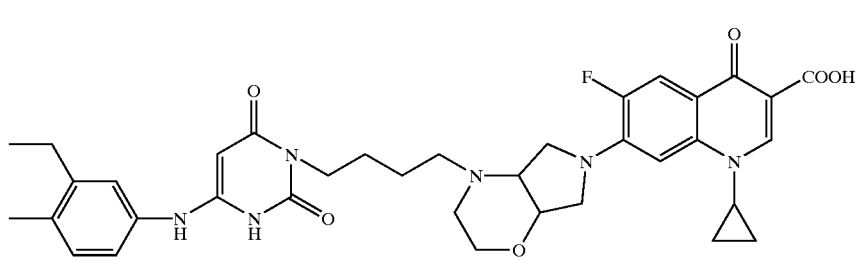

Compound 87

400 MHz ¹H NMR (DMSO-d₆): 10.32 (s, 1H, NH), 8.51 (s, 1H, FQ-C₂—H), 8.02 (s, 1H, NH), 7.74 (d, 1H, FQ-C₅—H), 7.04 (m, 2H, FQ-C₈—H and Ar—H), 6.86 (m, 2H, Ar—H), 4.66 (s, 1H, C₅—H), 4.03 (m, 1H, CHN), 3.6–3.9 (m, 5H, 2CH₂N and CHN), 3.40–3.50 (m, 5H, CH₂N, CH₂O and CH), 2.60 (q, 2H, Ar—CH₂CH₃), 2.16 (s,3H, Ar—CH₃), 1.39–1.46 (m, 4H, 2CH₂), 1.23 (m, 2H, CH₂), 1.06 (m, 5H, Ar—CH₂CH₃ and CH₂) ppm.

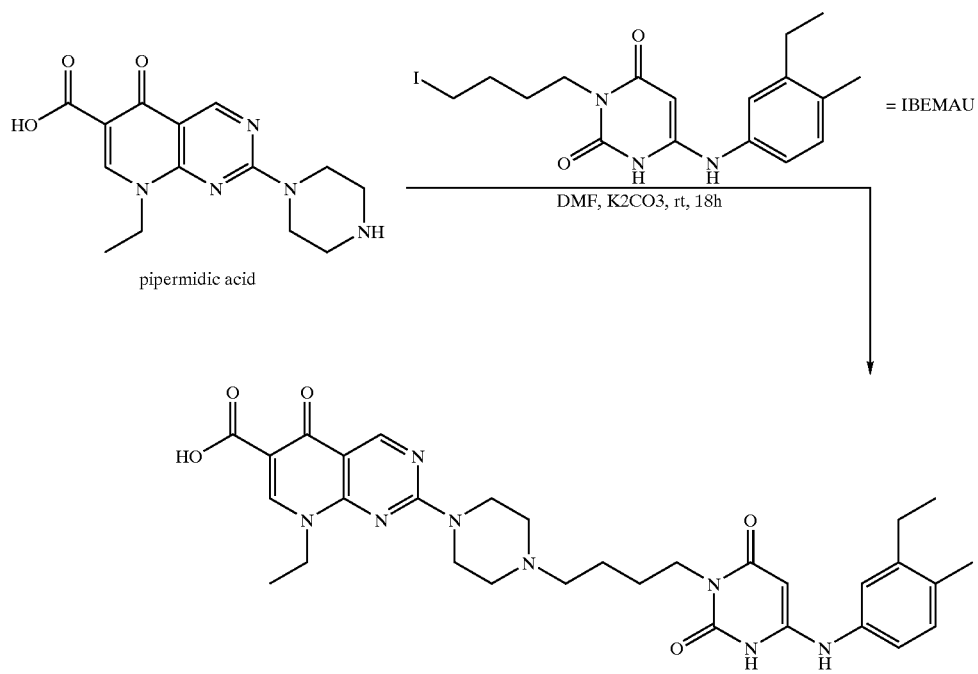

Compound 79

Pipemidic acid (429 mg, 1.2 mmol) and 3-(4-iodobutyl)-6-(3-ethyl-4-methylanilino)uracil (613 mg, 1.44 mmol) were dissolved in dry N,N-dimethylformamide (7 ml). Sodium carbonate (254 mg, 2.4 mmol) was added, and the mixture was stirred at room temperature overnight. The mixture was diluted with dichloromethane:methanol (10:1 v/v), and the solution was washed with saturated aqueous ammonium chloride. The aqueous fraction was extracted with dichloromethane:methanol (10:1 v/v), the organic fractions were dried over sodium sulfate and the solvent evaporated. The resulting white solid was triturated with hot acetonitrile, then the residue was recrystallized from hot methanol to obtain 689 mg (yield 95%) of Compound 79.

400 MHz $^1$H NMR (DMSO-d$_6$):10.37 (s, 1H, NH), 9.19 (s, 1H, FQ-H), 8.95 (s, 1H, FQ-H), 8.06 (s, 1H, NH), 7.11 (d, 1H, Ar—H), 6.93 (m, 2H, Ar—H), 4.70 (s, 1H, C$_5$—H), 4.36 (q, 2H, CH$_2$N(Et)), 3.93 and 3.86 (br.s, 2H, 2CH$_2$N), 3.68 (t, 2H, CH$_2$N), 2.54 (q, 2H, Ar—CH$_2$CH$_3$), 2.46 (br.m, 4H, 2CH$_2$N), 2.30 (m, 2H, CH$_2$N), 2.21 (s, 3H, ArCH$_3$), 1.41–1.50 (m, 4H, 2CH$_2$), 1.33 (t, 3H, Me), 1.11 (t, 3H, Ar—CH$_2$CH$_3$) ppm.

Compound 79a, the methanesulfonate salt of Compound 79. Methanesulfonic acid (0.6 ml of methanolic solution, 0.385 mmol/ml, 0.229 mmol) was added to a solution of Compound 79 (69 mg, 0.1145 mmol) in methanol. The mixture was stirred at room temperature for fifteen minutes, evaporated to dryness, triturated consecutively with diethyl ether, acetonitrile and methanol, and dried in vacuo to give 76 mg (84%) of Compound 79a.

Compound 79b, the hydrochloride salt of Compound 79. Compound 79 (35 mg, 0.06 mmol) was dissolved in methanolic hydrogen chloride (1N, 3 ml). The mixture was stirred at 0° C. for fifteen minutes, the solvent evaporated to dryness and the residue was triturated with diethyl ether to give hydrochloride 79b (30 mg, 77%).

Compound 79c, the acetate salt of Compound 79. Compound 79 (38 mg, 0.06 mmol) was dissolved in methanol. An excess of acetic acid (1 ml) was added to the solution, and the mixture was stirred at 0° C. for twenty minutes. Evaporation and trituration with diethyl ether afforded acetate 79c in quantitative yield.

Compound 79d, the ammonium salt of Compound 79. Compound 79 (50 mg, 0.08 mmol) was dissolved in saturated methanolic ammonia, then the mixture was concentrated, and the resulting residue was triturated with diethyl ether afford Compound 79d in quantitative yield.

Compound 79e, the trifluoroacetate of compound 79. Compound 79 (70 mg, 0.116 mmol) was treated with 1:1 (v/v) solution of trifluoroacetic acid in dichloromethane (5 ml). The solvent was evaporated under reduced pressure, and the residue was dried in vacuo to afford Compound 79e in quantitative yield.

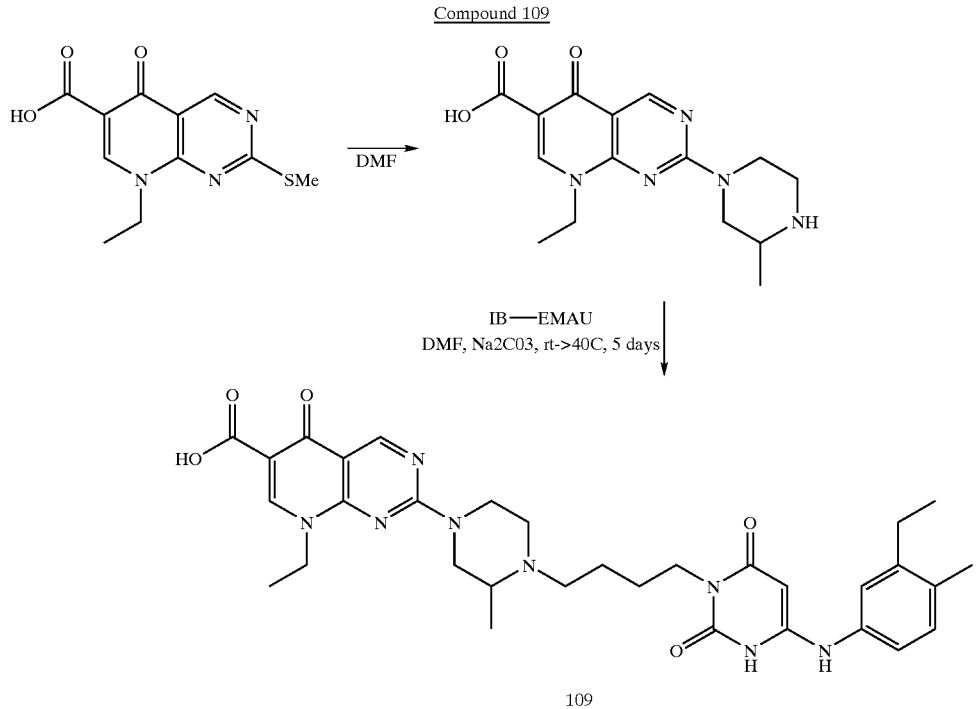

8-Ethyl-2-methylthio-5-oxo-5,8-dihydropyrido(2,3-d) pyrimidine-6-carboxylic acid (98 mg, 0.37 mmol) and 2-methylpiperazine (44 mg, 0.44 mmol) were dissolved in dry N,N-dimethylformamide (5 ml) and heated for 3 hours at 60° C. An additionnal 0.2 eq of amine was added, and heating was continued for 2 hours at 70° C. The solvent was evaporated to dryness, and the residue was dissolved in a mixture of dichloromethane:methanol and washed with brine. The aqueous fraction was back-extracted with dichloromethane:methanol, and the combined organic fractions were dried over sodium sulfate, concentrated and purified by column chromatography on silica gel using dichloromethane:methanol (gradient from 90:10 to 60:40) as eluent to obtain 75 mg (yield 63%) of piperazinoquinolone intermediate as a white solid.

The above intermediate (26 mg, 0.08 mmol) and IB-EMAU (42 mg, 0.1 mmol) were dissolved in dry N,N-dimethylformamide (2 ml). Sodium carbonate (17 mg, 0.16 mmol) was added, and the mixture was stirred for a week at room temperature. The solvent was evaporated to dryness, and the residue dissolved in a mixture of dichloromethane:methanol and purified by column chromatography using dichloromethane:methanol (gradient from 100% dichloromethane to 70:30) as eluent. The resulting white solid (63 mg) was triturated with acetonitrile:diethyl ether to give 12 mg (yield 24%) of Compound 109.

400 MHz $^1$H NMR (CD$_3$OD): 9.32 (s, 1H, FQ-H), 8.81 (s, 1H, FQ-H), 7.16 (m, 1H, Ar—H), 7.01 (m, 1H, Ar—H), 6.96 (m, 1H, Ar—H), 4.82 (s, 1H, C$_5$—H), 4.40 (m, 5H, CHN and 2CH$_2$N), 3.88 (m, 2H, 2CH$_2$N), 3.13–3.47 (m, 4H, 2CH$_2$N), 2.65 (m, 4H, Ar—CH$_2$CH$_3$ and CH$_2$N), 2.29 (s, 3H, ArCH$_3$), 1.19–1.65 (m, 11H, NCHCH$_3$+Ar—CH$_2$CH$_3$+NCH$_2$CH$_3$+2CH$_2$) ppm.

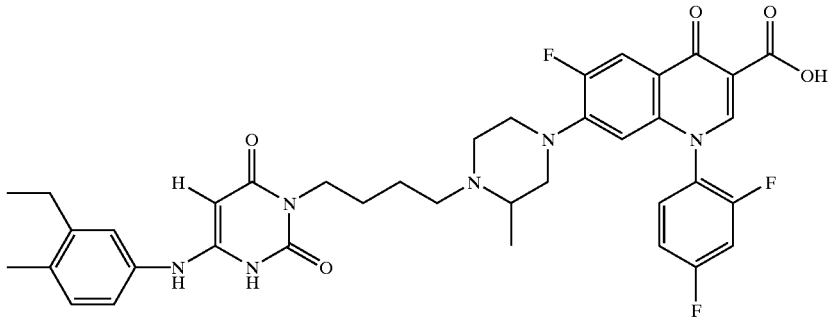

Compound 89

This compound was made as described for Compound 70, but starting with ethyl 1-(2,4-difluorophenyl)-4-oxo-6-fluoro-7-(3-methylpiperazinyl)-quinoline-3-carboxylate. Yield: 94%.

300 MHz $^1$H NMR (DMSO-d$_6$): 15.0 (s, 1H), 10.70 (s, 1H), 8.82 (s, 1H), 8.35 (s, 1H), 7.96 (m, 2H), 7.72 (t, 1H), 7.46 (t, 1H), 6.92–7.12 (m, 3H), 6.25 (d, 1H), 4.70 (s, 1H), 3.68 (t, 2H), 2.2–3.4 (m, 1H), 2.18 (s, 3H), 1.3–1.62 (m, 4H), 1.10–1.22 (m, 6H) ppm A mixture of ethyl 1-cyclopropyl-6,8-difluoro-4-oxo-7-[3-(hydroxymethyl)-piperazinyl]quinoline-3-carboxylate (400 mg, 1 mmol), sodium bicarbonate (250 mg, 3 mmol), and 3-(4-iodobutyl)-6-(3-ethyl-4-methylanilino)uracil (1.1 g, 2.6 mmol) in 80 ml N,N-dimethylformamide was stirred at room temperature overnight. The solvent was removed, and water was added, extracted with chloroform, and dried over sodium sulfate. After removal of solvents, the residue was purified by chromatography on silica gel using 7–15%

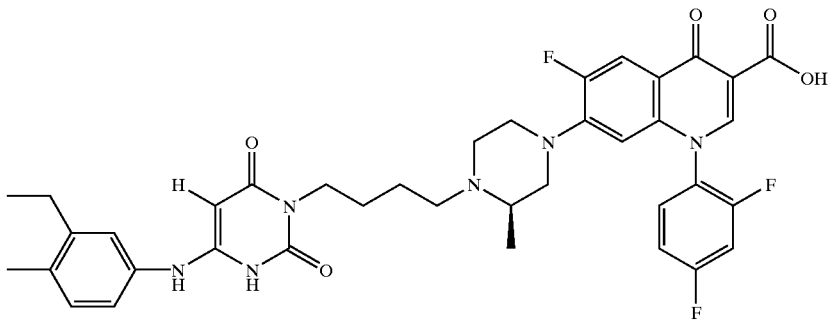

Compound 90

This compound was made as described for Compound 89, but starting with (R)-ethyl 1-(2,4-difluorophenyl)-4-oxo-6-fluoro-7-(3-methylpiperazinyl)-quinoline-3-carboxylate. Yield: 92%.

300 MHz $^1$H NMR (DMSO-d$_6$): 15.0 (s, 1H), 10.38 (s, 1H), 8.82 (s, 1H), 8.40 (s, 1H), 7.96 (d, 1H), 7.90 (m, 1H), 7.72 (t, 1H), 7.46 (t, 1H), 6.92–7.12 (m, 3H), 6.23 (d, 1H), 4.72 (s, 1H), 3.68 (t, 2H), 2.2–3.4 (m, 11H), 2.18 (s, 3H), 1.3–1.62 (m, 4H), 1.10–1.22 (m, 6H) ppm methanol in chloroform as eluent to give 320 mg of ethyl ester 46%) as a white solid.

The above ethyl ester (200 mg) was dissolved in 80 ml of a 4:1 mixture of methanol and water. Lithium hydroxide (60 mg) was added to the solution, and the mixture was stirred at room temperature overnight. The mixture was brought to pH 5–6 with acetic acid, and the solvents were evaporated to dryness and a small amount of water was added. The

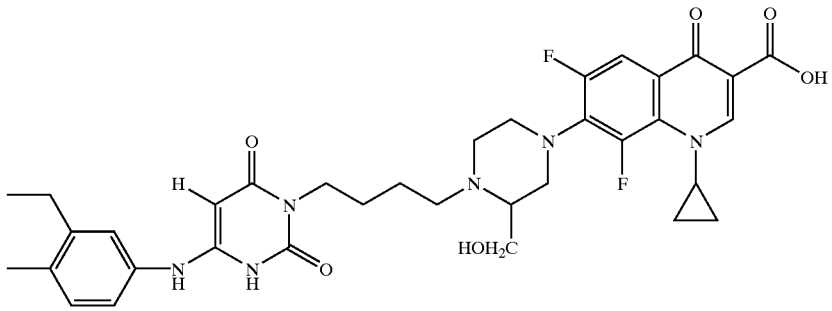

Compound 91 suspension was filtered and the solid dried in vacuo to give compound 91, 176 mg (yield 92%), as an off-white solid.

300 MHz $^1$H NMR (DMSO-d$_6$): 15.20 (s, 1H), 10.45 (s, 1H), 8.68 (s, 1H), 8.42 (s, 1H), 7.8 (d, 1H), 6.86–7.14 (m, 3H), 4.76 (s, 1H), 4.57 (s, 1H), 4.08 (m, 1H), 3.74 (m, 4H), 2.3–3.6 (m, 11H), 2.18 (s, 3H), 1.38–1.6 (m, 4H), 1.05–1.26 (m, 7H) ppm.

mg, 0.83 mmol) in DMSO (5 mL) was stirred at room temperature for 24 hours. A solution of 5% potassium hydroxide in 90% methanol (5 ml) was added, the mixture was stirred for 4 hours at room temperature, methanol was removed at reduced pressure, and 50 ml of 1% aqueous potassium hydroxide was added. The mixture was filtered Compound 92

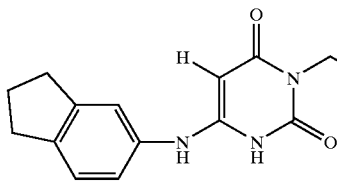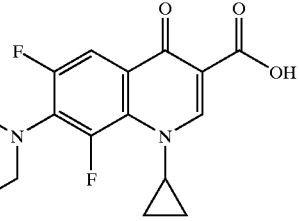

This compound was prepared as described for Compound 70, but with the use of 3-(4-iodobutyl)-6-(5-indanylamino)uracil. Yield: 91%.

300 MHz $^1$H NMR (DMSO-d$_6$): 14.80 (s, 1H), 10.75 (s, 1H), 8.68 (s, 1H), 8.40 (s, 1H), 7.82 (d, 1H), 7.23 (d, 1H), 7.08 (s, 1H), 6.96 (d, 1H), 4.72 (s, 1H), 4.14 (m, 1H), 3.75 (t, 2H), 1.95–3.45 (m, 15H), 1.3–1.6 (m, 4H), 1.15 (m, 4H), 1.0 (d, 3H) ppm.

over a glass filter, and the residue was thoroughly washed with small portions of 1% aqueous potassium hydroxide. The clear filtrate was extracted with dichloromethane (5×5 ml). The aqueous phase was separated, and placed under vacuum for a short time to remove all traces of dichloromethane. The clear aqueous solution was neutralized by dropwise addition of acetic acid (until pH 6–7). The slurry was filtered, and the solid was washed thoroughly with Compound 93

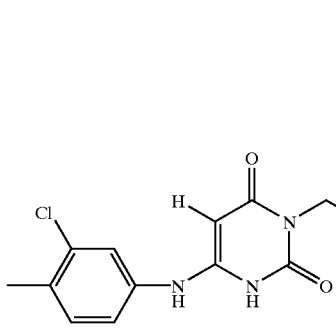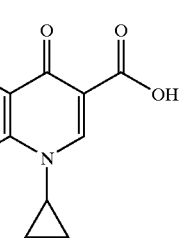

A mixture of ethyl 1-cyclopropyl-6,8-difluoro-4-oxo-7-(3-methyl piperazinyl)quinoline-3-carboxylate (210 mg, 0.54 mmol), sodium bicarbonate (72 mg, 0.86 mmol), and 3-(4-iodobutyl)-6-(3-chloro-4-methylanilino)uracil (361 water, dried on the filter, then in air, ground and dried in air overnight to afford 310 mg (86%) of compound 93.

300 MHz $^1$H NMR (DMSO-d$_6$): 14.80 (s, 1H), 10.80 (s, 1H), 8.65 (s, 1H), 8.43 (s, 1H), 7.76 (d, 1H), 7.0–7.4 (m, 3H), 4.81 (s, 1H), 2.20–4.2 (m, 15H), 1.0–1.6 (m, 11H) ppm Compound 94

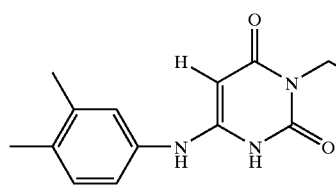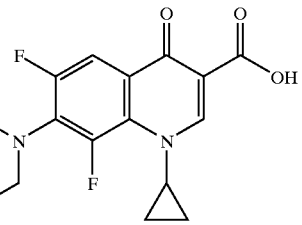

This compound was prepared as described for Compound 93, but by the use of 3-(4-iodobutyl)-6-(3,4-dimethylanilino)uracil. Yield 92%.

300 MHz $^1$H NMR (DMSO-d$_6$): 14.80 (s, 1H), 10.48 (s, 1H), 8.65 (s, 1H), 8.45 (s, 1H), 7.80 (d, 1H), 7.0–7.4 (m, 3H), 4.72 (s, 1H), 4.1 (m, 1H), 3.68 (m, 2H), 2.10–3.5 (m, 15H), 1.0–1.6 (m, 11H) ppm methylpiperazine (41.0 g, 0.41 mol) and 800 ml dimethylsulfoxide was heated under nitrogen at 80° C. for 19 hours. Sodium bicarbonate (34 g, 0.41 mol) was added in portions to the stirring mixture at 80° C., and the mixture was allowed to cool to room temperature. Acetone (400 ml) was added, and the mixture was stirred at room temperature for 30 minutes, then at 0–5° C. for 30 minutes. The solid was Compound 95

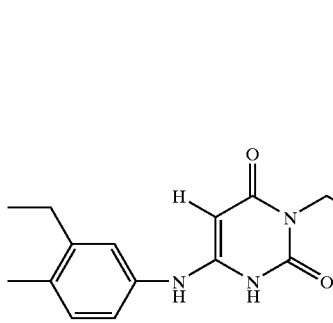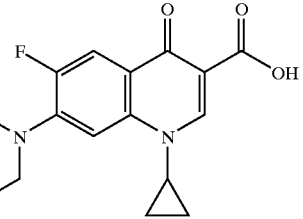

This compound was prepared by the same procedure as the preparation of Compound 91, but with the use of (R)-ethyl 1-cyclopropyl-6-fluoro-4-oxo-7-(3-methylpiperazinyl)quinoline-3-carboxylate. Yield: 82%.

300 MHz $^1$H NMR (DMSO-d$_6$): 15.20 (s, 1H), 10.50 (s, 1H), 8.65 (s, 1H), 8.2 (s, 1H), 7.90 (d, 1H), 7.53 (d, 1H), 7.13 (d, 1H), 6.92–6.97 (m, 2H), 4.73 (s, 1H), 2.2–3.80 (m, 17H), 1.0–1.9 (m, 14H) ppm filtered and washed with 200 ml of cold acetone. The solid was dissolved in 1.5 liter (L) of dichloromethane, and 500 ml of saturated aqueous sodium bicarbonate was added. After stirring at room temperature for 30 minutes, the organic phase was separated, washed with 500 ml of saturated aqueous sodium bicarbonate and 500 ml water. The organic phase was dried over magnesium sulfate and concentrated under vacuum. The crude solid was mixed in 500

Compound 96

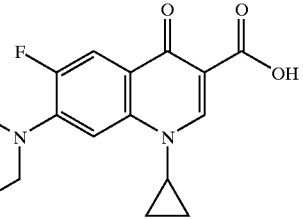

This compound was prepared as described for Compound 95, but by the use of 3-(4-iodobutyl)-6-(3,4-dimethylanilino)uracil. Yield: 91%.

300 MHz $^1$H NMR (DMSO-d$_6$): 15.20 (s, 1H), 10.46 (s, 1H), 8.65 (s, 1H), 8.14 (s, 1H), 7.88 (d, 1H), 7.56 (d, 1H), 7.12 (d, 1H), 6.96 (s, 1H), 6.87 (d, 1H), 4.72 (s, 1H), 3.88 (m, 1H), 3.69 (t, 2H), 3.50 (t, 2H), 2.20–3.40 (m, 7H), 2.14 (m, 6H), 1.04–1.60 (m, 11H) ppm ml of hot acetone and allowed to cool down to room temperature, then to 10° C. while stirring. The suspension was filtered and the solid was washed with 200 ml of cold acetone, then 200 ml of hexane. After drying in vacuum 43.3 g (53% yield) of fluoro ester intermediate.

A mixture of the fluoro ester intermediate (3.73 g, 10 mmol, 1 eq), IB-DMAU (6.2 g, 15 mmol, 1.50 eq), sodium bicarbonate (1.7 g, 20 mmol, 2.0 eq) and dimethylsulfoxide Compound 97

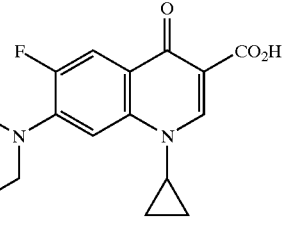

A mixture of ethyl 1-cyclopropyl-7,8-difluoro-4-quinolone-3-carboxylate (80.0 g, 0.273 mol), (S)-2-

(70 ml, 20 vol.) was stirred at room temperature for 3 days under nitrogen. Water (30 ml) was added, and the mixture was stirred for 30 minutes at room temperature. The mixture was filtered, and the solid was mixed with acetone (60 ml) at room temperature for 30 min. The mixture was filtered to get a pale-yellow solid, which was heated in ethyl acetate (60 ml) at reflux for 30 min. The mixture was cooled to room temperature and filtered to get a pale-yellow solid. The solid was stirred in MeOH (60 mL) for 1 hour, filtered and dried under high vacuum overnight to give 4.76 g of ester as a light yellow solid (yield 65%).

The ethyl ester (4 g, 6.07 mmol) was suspended in 280 ml of 4:1 methanol:water, and sodium hydroxide (1.58 g, 39.5 mmol) was added. The suspension was stirred at room temperature overnight. The mixture was acidified with acetic acid (2.3 ml, 40 mmol) to pH 5–6 and concentrated to dryness. Water (25 ml) was added and the suspension was stirred at room temperature for 1 hr. The suspension was filtered and the solid washed with water. The solid was treated with methanol (50 ml) and stirred at room temperature for 1 hr. The mixture was filtered to get 3.2 g of Compound 97 (84% yield) as a pale yellow solid.

400 MHz $^1$H NMR (DMSO): 8.62 (s, 1H, FQ-C$_2$—H), 8.58 (s, 1H, NH), 7.85 (d, 1H, FQ-C$_5$—H), 7.52 (d, 1H, FQ-C$_8$—H), 6.90–7.10 (m, 3H, Ar—H), 4.72 (s, 1H, C$_5$—H), 3.62–3.85 (m, 3H), 3.40–3.50 (m, 2H), 3.10 (m, 1H), 2.95–2.58 (m, 4H), 2.39 (m, 1H), 2.3–2.05 (m, 7H), 1.60–1.1 (m, 8H), 1.05 (d, 3H).

A mixture of (R)-ethyl 1-cyclopropyl-6,8-difluoro-4-oxo-7-(3-methylpiperazinyl) quinoline-3-carboxylate (391 mg, 1.0 mmol), sodium bicarbonate (252 mg, 3.0 mmol), and 3-(4-iodobutyl)-6-(3,4-dimethylanilino)uracil (1.03 g, 2.5 mmol) in 100 ml of N,N-dimethylformamide was stirred at room temperature overnight. After the solvent was removed, water was added and extracted with chloroform. The extracts were dried over sodium sulfate, and, after removal of solvents, the residue was purified by chromatography on silica gel using 5–10% methanol in chloroform as eluent to give 352 mg of ethyl ester (yield: 52%) as a white solid.

The above ethyl ester (300 mg) was dissolved in a 4:1 mixture of methanol and water (100 ml). Lithium hydroxide (60 mg) was added to the solution, and the mixture was stirred at room temperature overnight. The mixture was brought to pH 5–6 with acetic acid, the solvent was evaporated to dryness, and a small amount of water was added. The suspension was filtered, and the solid was dried in vacuo to give compound 98, 267 mg (yield: 93%), as an off-white solid. Yield: 93%.

300 MHz $^1$H NMR (DMSO-d$_6$): 14.80 (s, 1H), 10.48 (s, 1H), 8.65 (s, 1H), 8.20 (s, 1H), 7.80 (d, 1H), 7.0–7.4 (m, 3H), 4.72 (s, 1H), 4.1 (m, 1H), 3.68 (m, 2H), 2.10–3.5 (m, 15H), 1.0–1.6 (m, 11H) ppm Compound 99

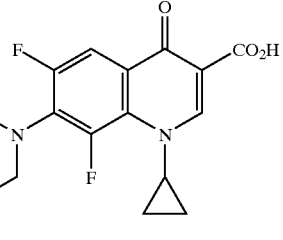

A suspension of ethyl 1-cyclopropyl-6,7,8-trifluoro-4-quinolone-3-carboxylate (58 g 0.188 mol) and (S)-2-methylpiperazine (28.5 g, 0.282 mol) in dimethylsulfoxide (500 ml) was stirred overnight at 80° C. The solvent was removed under reduced pressure, solids were dissolved in dichloromethane (300 ml) and water (200 ml). Sodium bicarbonate (18 g) was added portionwise, and the mixture was stirred for 30 min, filtered through a sintered glass filter to remove suspended solids. The organic layer was separated, and the aqueous layer washed with dichloromethane (4×50 ml). The organic extracts were combined and concentrated to dryness under reduced pressure. The residue was dissolved in hot toluene (200 ml). The toluene Compound 98

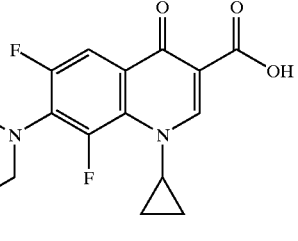

solution was cooled and concentrated to dryness under reduced pressure. The residue was crystallized from acetone (380 ml), and the product was filtered and washed with cold acetone (200 ml) to give 54 g (73%) of difluoro ester intermediate. Reaction of the difluoro ester intermediate with IB-DMAU as described above for Compound 98 gave 0.95 g of Compound 99 (79% yield) as a pale yellow solid.

400 MHz $^1$H NMR (DMSO): 8.64 (s, 1H), 8.42 (broad s, 1H), 7.78 (d, 1H, J=12.1 Hz), 7.1 (d, 1H, J=7.9 Hz), 6.97 (s, 1H), 6.91 (d, 1H, J=7.9 Hz), 4.72 (s, 1H), 4.1 (m, 1H), 3.7 (m, 2H), 2.98 (m, 1H), 2.81 (m, 1H), 2.64 (m, 1H), 2.38–2.02 (m, 9H), 1.58–1.36 (m, 4H), 1.08 (m, 5H), 1.00 (d, 3H, J=6 Hz)

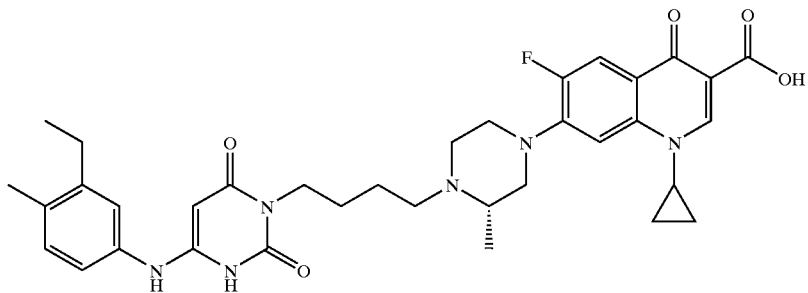

Compound 100

Reaction of IB-EMAU as described for the synthesis of Compound 97 gave Compound 100 (97% yield) as a light yellow powder.

400 MHz $^1$H NMR (DMSO): 8.62 (s, 1H, FQ-C$_2$—H), 8.25 (s, 1H, NH), 7.85 (d, 1H, FQ-C$_5$—H), 7.52 (d, 1H, FQ-C$_8$—H), 6.90–7.10 (m, 3H, Ar—H), 4.72 (s, 1H, C$_5$—H), 3.62–3.85 (m, 3H), 3.40–3.50 (m, 2H), 3.10 (m, 1H), 2.78–2.95 (m, 2H), 2.70 (m, 1H), 2.58 (m, 3H), 2.39 (m, 1H), 2.20 (m, 4H), 1.35–1.60 (m, 4H), 1.30 (m, 2H), 1.0–1.20 (m, 8H).

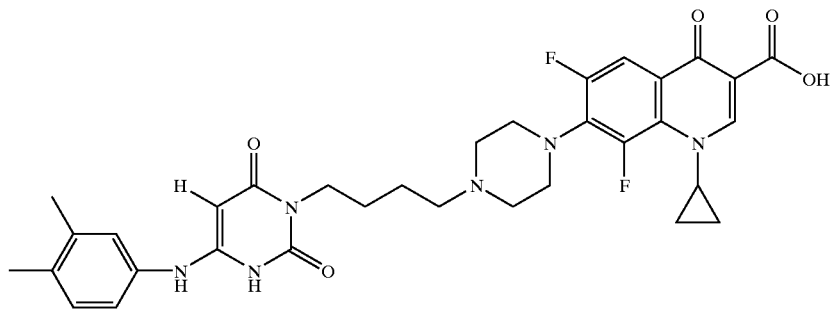

Compound 101

This compound was prepared by the same procedure as the preparation of Compound 97, but with the use of ethyl 1-cyclopropyl-6,8-difluoro-4-oxo-7-(1-piperazinyl)quinoline-3-carboxylate. Yield: 82%.

300 MHz $^1$H NMR (DMSO-d$_6$): 14.75 (s, 1H), 10.35 (s, 1H), 8.65 (s, 1H), 8.1 (s, 1H), 7.81 (d, 1H), 7.12 (d, 1H), 6.92–6.97 (m, 2H), 4.71 (s, 1H), 4.1 (m, 1H), 3.68 (m, 2H), 2.15–3.4 (m, 16H), 1.5 (m, 4H), 1.2 (m, 4H) ppm

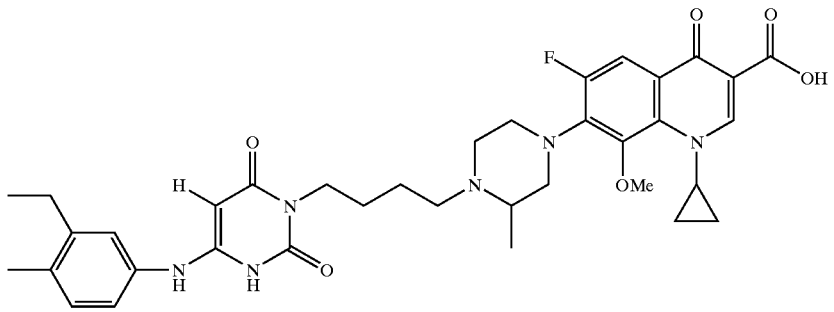

Compound 102

Synthesized as described for Compound 70. Yield: 89%. 300 MHz $^1$H NMR (DMSO-d$_6$): 14.83 (s, 1H), 10.45 (s, 1H), 8.75 (s, 1H), 8.12 (s, 1H), 7.80 (d, 1H), 7.15 (d, 1H), 6.98 (s, 1H), 6.95 (d, 1H), 4.73 (s, 1H), 4.18 (m, 1H), 2.5–3.8 (m, 16H), 2.21 (s, 3H), 1.0–1.7 (m, 14H) ppm Compound 103

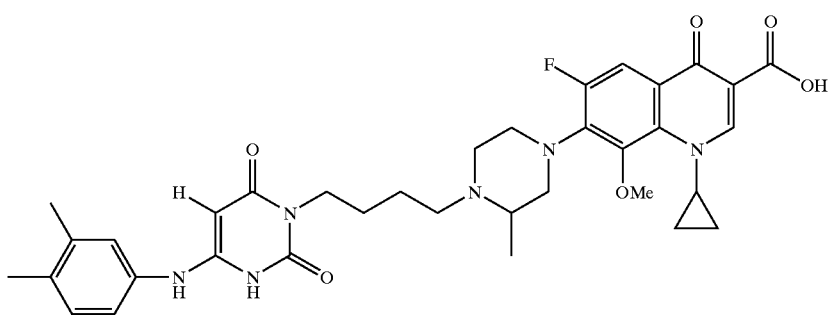

Synthesized as described for Compound 70. Yield: 87%. 300 MHz $^1$H NMR (DMSO-d$_6$): 14.80 (s, 1H), 10.40 (s, 1H), 8.75 (s, 1H), 8.15 (s, 1H), 7.80 (d, 1H), 7.15 (d, 1H), 6.98 (s, 1H), 6.95 (d, 1H), 4.72 (s, 1H), 4.18 (m, 1H), 2.5–3.8 (m, 14H), 2.21 (s, 3H), 2.2 (s, 3H), 1.0–1.7 (m, 11H) ppm Compound 104

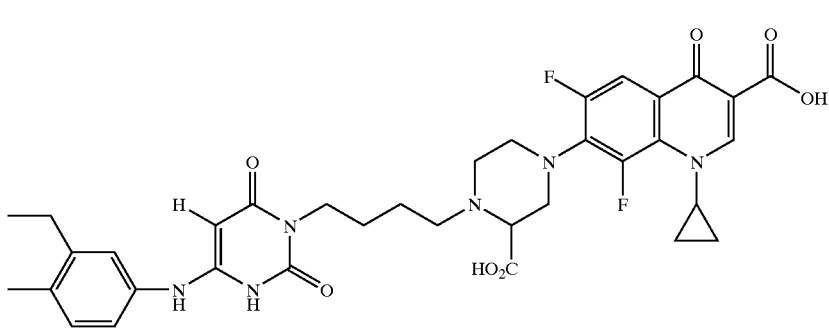

A mixture of ethyl 1-cyclopropyl-6-fluoro-4-oxo-7-[3-(ethoxycarbonyl)piperazinyl]-4-quinolone-3-carboxylate [prepared from 2-(ethoxycarbonyl)piperazine, made as described by Jucker and Rissi, Helv. Chim. Acta 1962, 272, 2383] (430 mg, 1 mmol), sodium bicarbonate (250 mg, 3 mmol) and IB-EMAU (1.1 g, 2.6 mmol) in N,N-dimethylformamide (70 ml) was stirred at room temperature for 48 hours. The solvent was removed in vacuo, and water was added. The mixture was extracted with chloroform and the extracts dried over sodium sulfate. The solution was concentrated and the residue was purified by silica gel column chromatography using methanol:chloroform (19:1-9-1) as eluent to give 270 mg (yield 37%) of the diethyl ester intermediate.

The diethyl ester intermediate (200 mg) was dissolved in 4:1 methanol:water (50 ml), and lithium hydroxide (70 mg) was added. The solution was stirred at room temperature overnight, adjusted to pH 5–6 with acetic acid, and the solvents removed in vacuo. A small amount of N,N-dimethylformamide was added to the residue, and the solid was filtered and dried in vacuo to give 97 mg (yield 52%) of Compound 104.

300 MHz $^1$H NMR (DMSO-d$_6$): 15.10 (s, 2H), 10.42 (s, 1H), 8.68 (s, 1H), 8.12 (s, 1H), 7.68 (d, 1H), 6.92–7.12 (m, 3H), 6.87 (d, 1H), 4.72 (s, 1H), 4.22 (m, 1H), 3.62 (m, 3H), 2.2–3.40 (m, 10H), 2.10 (s, 3H), 0.95–1.53 (m, 11H) ppm Compound 105

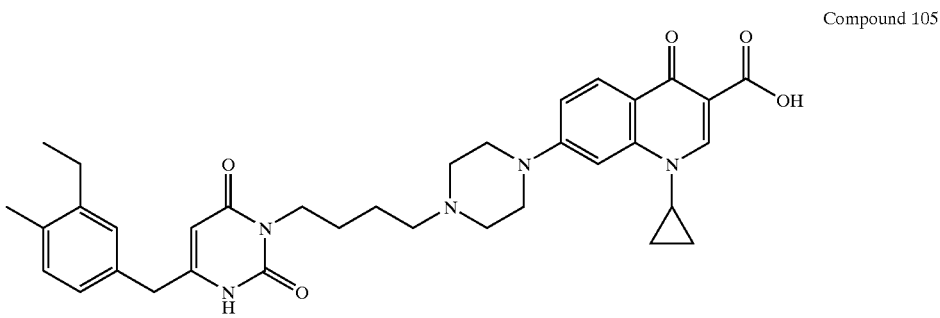

1-Cyclopropyl-7-piperazinyl-4-quinolone-3-carboxylic acid (76 mg, 0.24 mmol) and IB-EMAU (214 mg, 0.48 mmol) were dissolved in N,N-dimethylformamide (7 ml).

Sodium carbonate (51 mg, 0.48 mmol) was added, and the mixture was stirred at room temperature for 2 days. The solvent was removed under reduced pressure, and the residue was purified by flash chromatography on silica gel using dichloromethane: methanol (gradient from 100:0 to 80:20) as eluent to give 28 mg (yield 19%) of Compound 105. The product was purified a second time by HPLC. m/z=613 (M+H).

Aqueous sodium hydroxide (10%, 5 ml) was added to a suspension of the above ester intermediate in a mixture of tetrahydrofuran:water (1:1), and the mixture stirred at room temperature for 2 days. The mixture was neutralized to pH 6 by addition of acetic acid and evaporated to dryness. The resulting residue was mixed with water, and the pale yellow solid was filtered, washed with water and then diethyl ether.

Compound 106

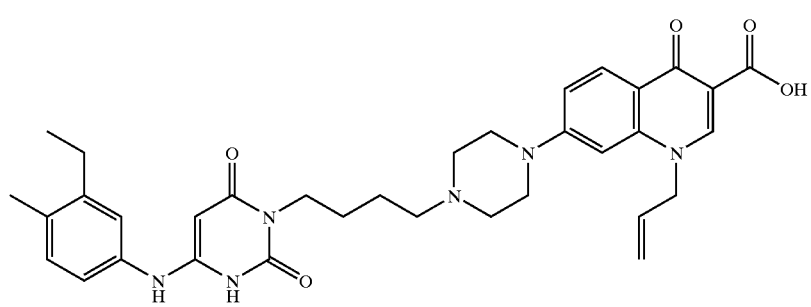

A solution of ethyl 1-allyl-7-fluoro-4-quinolone-3-carboxylate (390 mg, 1.41 mmol) and piperazine (1.22 g, 14.1 mmol) in dry N,N-dimethylformamide was heated for 7 hours at 110° C., then stirred at room temperature for 2 days. The solvent was evaporated to dryness, and the residue was purified by column chromatography on silica gel using dichloromethane:methanol (gradient from 98:2 to 85:15) as eluent affording 300 mg (62% yield) of ethyl 1-allyl-4-oxo-7-(4-piperazinyl)quinoline-3-carboxylate.

The above intermediate (300 mg, 0.88 mmol) and IB-EMAU (413 mg, 0.97 mmol) were dissolved in N,N-dimethylformamide (7 ml). Sodium carbonate (206 mg, 1.94 mmol) was added, and the mixture was stirred at room temperature overnight. The solvent was removed under reduced pressure, and the residue was purified by flash chromatography on silica gel using dichloromethane:methanol (95:5) as eluent to obtain 378 mg (67% yield) of ethyl ester intermediate.

The solid was triturated with methanol, acetonitrile and dried in vacuo to afford 153 mg of Compound 106 (48% yield) as a pale yellow solid.

400 MHz $^1$H NMR (DMSO): 8.84 (s, 1H, NH), 8.1 (d, 1H, FQ-C$_2$—H), 7.28 (dd, 1H, FQ-C$_5$—H), 6.88–7.06 (m, 5H, ArH and FQ-C$_8$—H), 5.98–6.05 (m, 1H, CH=CH$_2$), 5.13–5.26 (m, 4H, CH$_2$=CH and CH$_2$N), 4.73 (s, 1H, C$_5$—H), 3.69 (t, 2H, CH$_2$N), 3.31–3.39 (m, 8H, CH$_2$N$_{pip}$), 2.51 (q, 2H, ArCH$_2$CH$_3$), 2.30 (t, 2H, CH$_2$N), 2.18 (s, 3H, ArCH$_3$), 1.4–1.49 (m, 4H, 2×CH$_2$), 1.11 (t, 3H, ArCH$_2$CH$_3$).

Compounds 107 and 108

Compound 107

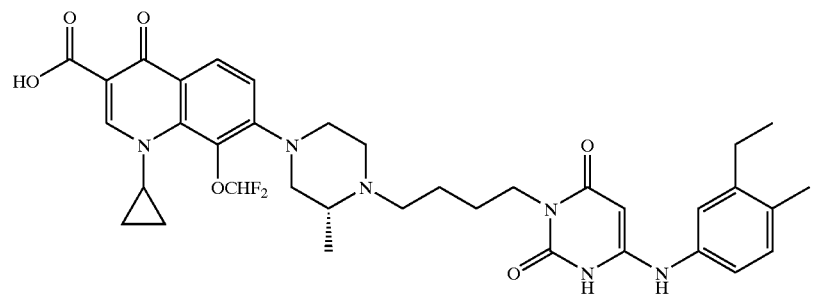

Compound 108

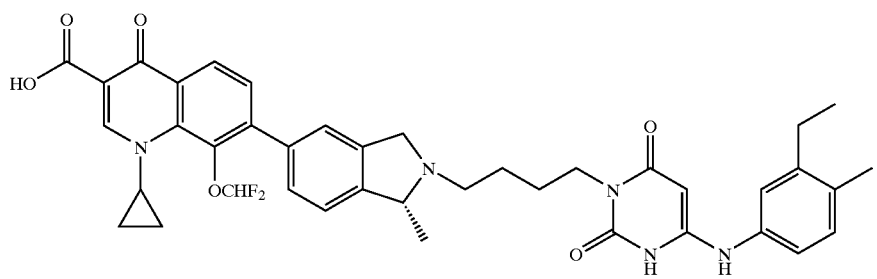

For compound 107 and compound 108, the quinolone was prepared by methods well known in the art, such as described in PCT publication WO 99/21849 (Toyama Chemical). Then, the general method III was followed to obtain compound 107 and compound 108.

Example 2

Characterization of Compounds

The following methods were used to characterize representative compounds.

Minimal Inhibitory Concentration (MIC) determinations. MIC values were determined in 96 well plates, with bacterial growth monitored at OD 600 nm in 200 µl following an initial bacterial seeding at approximately $1 \times 10^5$ colony forming units (CFU)/ml. Each drug is evaluated at five concentrations, with five data points at each dilution. MIC values (µg/ml) were determined against actively growing cultures in Heart-Brain Infusion (HBI) medium. Cell growth in cultures supplemented with a test compound was calculated as a percent of control at OD 600 nm after 16 to 18 hours at 37° C. This plate format conserves test compound and provides precise, quantitative data with low standard deviation determinations.

Polymerase IIIC (Pol IIIC) assay. DNA polymerase activity (or inhibition thereof) was measured in a 96-well plate format. B. subtilis Pol IIIC was isolated as described by Hammond and Brown (*Protein Expr. Purif.*, 3: 65–70 (1992)). Each 25 µl assay contained 30 mM Tris, pH 7.5, 10 mM magnesium acetate, 4 mM dithiothreitol, 20% glycerol, with 25 µM dATP, dCTP, dGTP and 10 µM dTTP (3H-labelled at 1.44 Ci/mmole) and 0.4 mg/ml activated calf thymus DNA as substrates, as described previously (see Barnes et al, op. cit). Assays were initiated by the addition of 0.025 to 0.06 units of enzyme 1 unit is the amount required to incorporate 250 pmoles of [$^3$H] dTMP in a standard assay), incubated for 10 minutes at 30° C. and terminated by the addition of 200 µl of cold 10% trichloroacetic acid (TCA), 10 mM sodium pyrophosphate. Precipitated labeled DNA was collected on glass fiber filter plates, washed, dried, and counted in a liquid scintillation counter.

Determination of Ki values. DNA polymerase activity was measured in a 96-well plate format in the absence of dGTP or dATP, depending on the structure of the test compound. Each 25 µl assay contained 30 mM Tris, pH 7.5, 10 mM magnesium acetate, 4 mM dithiothreitol, 20% glycerol, with 25 µM dATP, dCTP, and 10 µM dTTP (3H-labelled at 1.44 Ci/mmole) and 0.4 mg/ml activated calf thymus DNA as substrates, as described previously. To each well were added 2 µl of compound solution to give final concentrations ranging from 20–0.027 µg/ml in the assay. Assays were initiated by the addition of 0.025 to 0.06 units of enzyme (1 unit is the amount required to incorporate 250 pmoles of [$^3$H] dTMP in a standard assay), incubated for 10 minutes at 30° C. and terminated by the addition of 200 µl of cold 10% trichloroacetic acid, 10 mM sodium pyrophosphate. Precipitated labeled DNA was collected on glass fiber filter plates, washed, dried, and counted in a liquid scintillation counter. Ki is the concentration of test compound that reduces the control polymerase mc activity by 50 percent.

Results

Determination of Ki and MIC Values for Compounds.

The Ki and MIC (µg/ml) against selected bacterial species were determined for representative compounds and also for the fluoroquinolone antibiotics norfloxacin (NFN) and ciprofloxacin (CPFN) and the polymerase mc parent inhibitor compound HB-EMAU. MIC values were determined for the Gram positive bacteria *Bacillus subtilis, Staphylococcus aureus* (two strains), *Enterococcus fecalis, Enterococcus fecium*, and for the Gram negative bacterium *Escherichia coli*. The results are shown in the tables below.

| Compound | Ki (µM) Pol IIIC | MIC (µg/ml) | | | | | |
|---|---|---|---|---|---|---|---|
| | | B. subtilis | S. aureus | S. aureus (Smith) | E. fecalis | E. fecium | E. coli |
| 1 | 0.024 | 0.156 | 0.625 | 0.625 | 1.25 | 1.25 | >20 |
| 5 | 0.016 | 0.078 | 0.156 | 0.156 | 1.25 | 2.5 | 10 |
| 6 | 0.018 | 0.156 | 0.625 | 0.625 | 1.25 | 1.25 | >20 |
| 7 | 0.021 | 0.156 | 0.625 | 1.25 | 1.25 | 1.25 | >20 |
| nflxn | inactive | 0.625 | 0.625 | 0.156 | 2.5 | 20 | 0.078 |
| 2 | 0.024 | 0.156 | 0.625 | 0.313 | 1.25 | 1.25 | 2.5 |
| 10 | 0.018 | 0.313 | 0.625 | 0.625 | 1.25 | 2.5 | 5 |
| 15 | 0.03 | 0.156 | 0.625 | 0.313 | 0.625 | 1.25 | 5 |
| 11 | 0.03 | 1.25 | 5 | 2.5 | 10 | 5 | >80 |
| 8 | 0.013 | 0.313 | 1.25 | 0.625 | 10 | >80 | 40 |
| cflxn | inactive | 0.156 | 0.156 | 0.078 | 0.625 | 10 | 0.078 |
| 12 | 0.018 | 0.156 | 0.313 | 0.313 | 2.5 | 5 | 2.5 |
| HB-EMAU | 0.066 | 1.25 | 10 | 5 | 5 | 5 | >80 | nfln = norfloxacin;
cflxn = ciprofloxacin

| Compound | Ki (µM) Pol IIIC | MIC (µg/ml) | | | | | |
|---|---|---|---|---|---|---|---|
| | | B. subtilis | S. aureus | S. a. (Smith) | E. fecalis | E. fecium | E. coil |
| 64 | 0.055 | 0.313 | 1.25 | 0.625 | 1.87 | 3.7 | 7.5 |
| 65 | 0.095 | 0.23 | 0.95 | 0.46 | 1.87 | 1.87 | 10 |
| 66 | 0.26 | 0.313 | 0.95 | 0.625 | 1.25 | 3.7 | 6.1 |
| 67 | 0.034 | 0.23 | 0.625 | 0.313 | 1.25 | 2.5 | 10 |
| 68 | 0.047 | 0.95 | 1.25 | 0.625 | 40 | 1.25 | 12.5 |
| 69 | 0.026 | 0.23 | 0.625 | 0.46 | 0.95 | 1.25 | 30 |

-continued

| | Ki (μM) | MIC (μg/ml) | | | | | |
|---|---|---|---|---|---|---|---|
| Compound | Pol IIIC | B. subtilis | S. aureus | S. a. (Smith) | E. fecalis | E. fecium | E. coil |
| 70 | 0.019 | 0.156 | 0.313 | 0.156 | 0.95 | 1.25 | >80 |
| 71 | 0.007 | 0.156 | 0.313 | 0.156 | 1.25 | 1.87 | 5 |
| 72 | 0.004 | 0.156 | 0.625 | 0.625 | 1.25 | 1.25 | 20 |
| 77 | 8 | 5 | 2.5 | 2.5 | >80 | >80 | >80 |
| 78 | 2.4 | 0.625 | 1.25 | 2.5 | 5 | 5 | >80 |
| 79 | 0.028 | 0.156 | 1.25 | 0.95 | 2.5 | 3.7 | >80 |
| 80 | 0.037 | 2.5 | 7.5 | 5 | 12.5 | 20 | 0.8 |
| 81 | 0.04 | 1.25 | 5 | 2.5 | 3.7 | 12.5 | >80 |
| 82 | 0.041 | 1.25 | 2.5 | 1.25 | 20 | >80 | >80 |
| 83 | 0.041 | 3.7 | 20 | 5 | 5 | 40 | >80 |
| 84 | 0.033 | 0.313 | 1.25 | 0.625 | 2.5 | 25 | >80 |
| 85 | 0.059 | 0.313 | 5 | 6.1 | 7.5 | 12.5 | >80 |
| 86 | 0.054 | 2.5 | 5 | 2.5 | 10 | 40 | >80 |
| 87 | 0.088 | 0.313 | 1.87 | 0.625 | 2.5 | 7.5 | >40 |
| 88 | 0.024 | 0.625 | 1.25 | 1.25 | 2.5 | 5 | >20 |
| 89 | 0.018 | 0.156 | 0.313 | 0.156 | 0.625 | 0.625 | >80 |
| 90 | 0.017 | 0.236 | 0.625 | 0.313 | 1.25 | 1.25 | >40 |
| 91 | 0.011 | 0.235 | 1.25 | 0.625 | 2.5 | 2.5 | >80 |
| 92 | 0.016 | 0.117 | 0.313 | 0.235 | 0.625 | 0.937 | 2.5 |
| 94 | 0.026 | 0.156 | 0.625 | 0.313 | 1.25 | 2.5 | 2.5 |
| 95 | 0.012 | 0.235 | 1.25 | 0.625 | 0.625 | 0.625 | 10 |
| 96 | 0.019 | 0.156 | 0.625 | 0.313 | 0.625 | 0.625 | 5 |
| 97 | 0.037 | 0.235 | 1.25 | 0.625 | 0.625 | 1.25 | 40 |
| 98 | 0.029 | 0.313 | 1.25 | 0.625 | 1.25 | 1.25 | 5 |
| 99 | 0.03 | 0.156 | 0.313 | 0.156 | 0.625 | 1.25 | 0.625 |
| 100 | 0.011 | 0.156 | 0.937 | 0.625 | 0.475 | 0.937 | 50 |
| 101 | 0.024 | 0.235 | 0.625 | 0.313 | 0.937 | 1.25 | 5 |

The data in the above tables show that the compounds are mostly potent inhibitors of Pol IIIC and also have potent antibacterial activity against clinically relevant Gram positive bacteria. Some of the compounds also demonstrate activity against the Gram negative bacteria *Escherichia coli*.

Compounds were also tested for antibacterial activity against certain clinically relevant strains, e.g., methicillin sensitive (MSSA) and methicillin resistant (MRSA) strains of *Staphylococcus aureus*. The results of this analysis are show in the table below.

| | MIC (μg/ml) | | | | | |
|---|---|---|---|---|---|---|
| Compound | S. aureus | S. aureus (Smith) | MSSA108 | MRSA1094 | MRSA1123 | MRSA1132 |
| 1 | 0.313 | 0.313 | 0.313 | 0.625 | 0.625 | 0.625 |
| 5 | 0.156 | 0.156 | 0.625 | 0.625 | 0.625 | 0.625 |
| 6 | 0.625 | 0.625 | 0.625 | 1.25 | 0.625 | 0.625 |
| 7 | 0.625 | 0.625 | 0.313 | 0.625 | 0.625 | 0.625 |
| 2 | 0.625 | 0.313 | 0.313 | 0.625 | 0.625 | 0.625 |
| 10 | 0.625 | 0.625 | 0.625 | 1.25 | 1.25 | 0.625 |
| 12 | 0.313 | 0.313 | 0.625 | 0.625 | 1.25 | 0.625 |
| 70 | 0.390 | 0.210 | N.D. | 0.940 | 0.940 | 0.310 |

MSSA = methicillin sensitive *S. aureus* strain;
MRSA = methicillin resistant *S. aureus* strain;
N.D. = not determined The data in the above table show that representative compounds have potent antibacterial activity against clinical isolates of antibiotic sensitive and antibiotic resistant strains of *S. aureus*.

Example 3
Characterization of Compounds: in vivo Antibiotic Activity

Swiss Webster mice, ca. 20 g each, were infected with *Staphylococcus aureus* (Smith strain) by the intraperitoneal route. Test compounds (2, 4, 5, 6, 7, 8, 10, 12) were dissolved in 10% dimethylsulfoxide in peanut oil to a concentration of 2 mg/ml. Vancomycin was used as positive control drug (i.e., protection from lethal infection). Fifteen minutes after infection, test compounds, vancomycin, or vehicle alone were given intraperitoneally to groups of five mice each. Animals were monitored for three days, and the number of mice surviving was tabulated for each treatment.

Figure 1B:
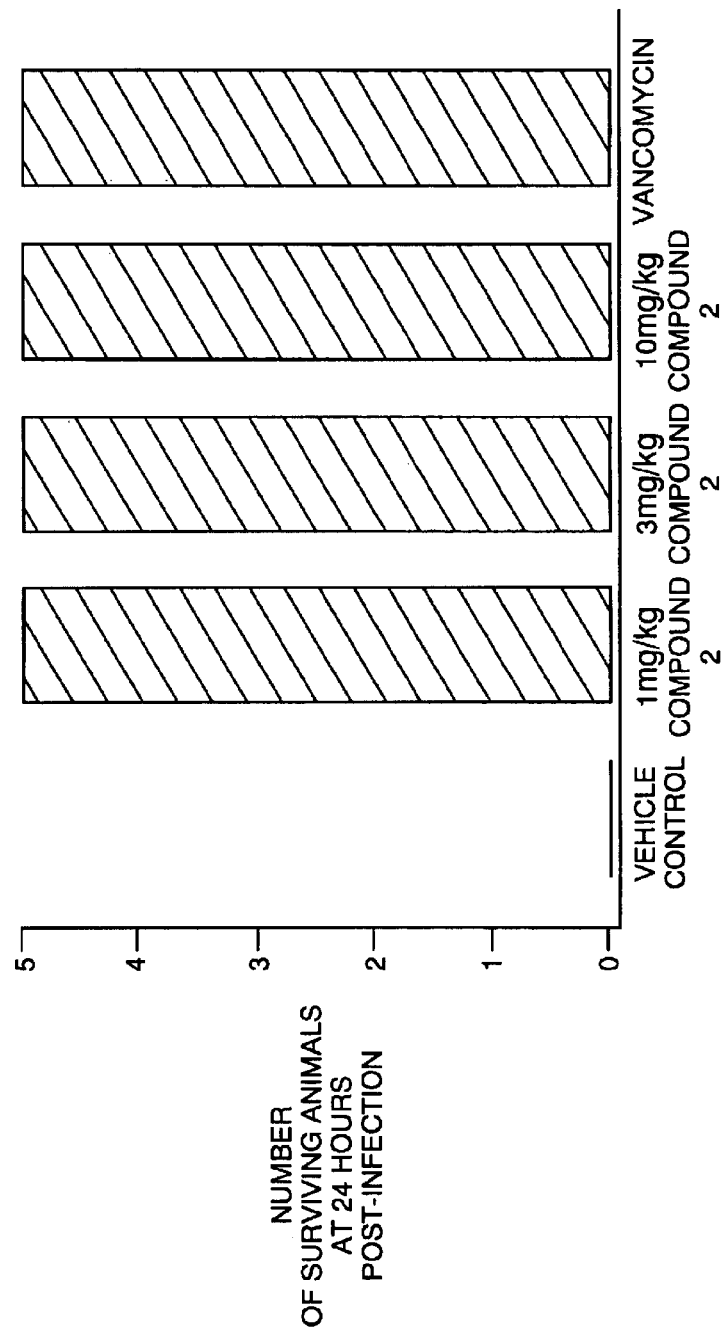
Figure 2A:
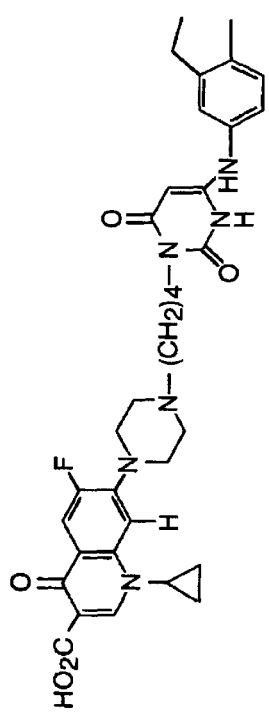
FIGS. 2A and 2B.
Figure 2B:
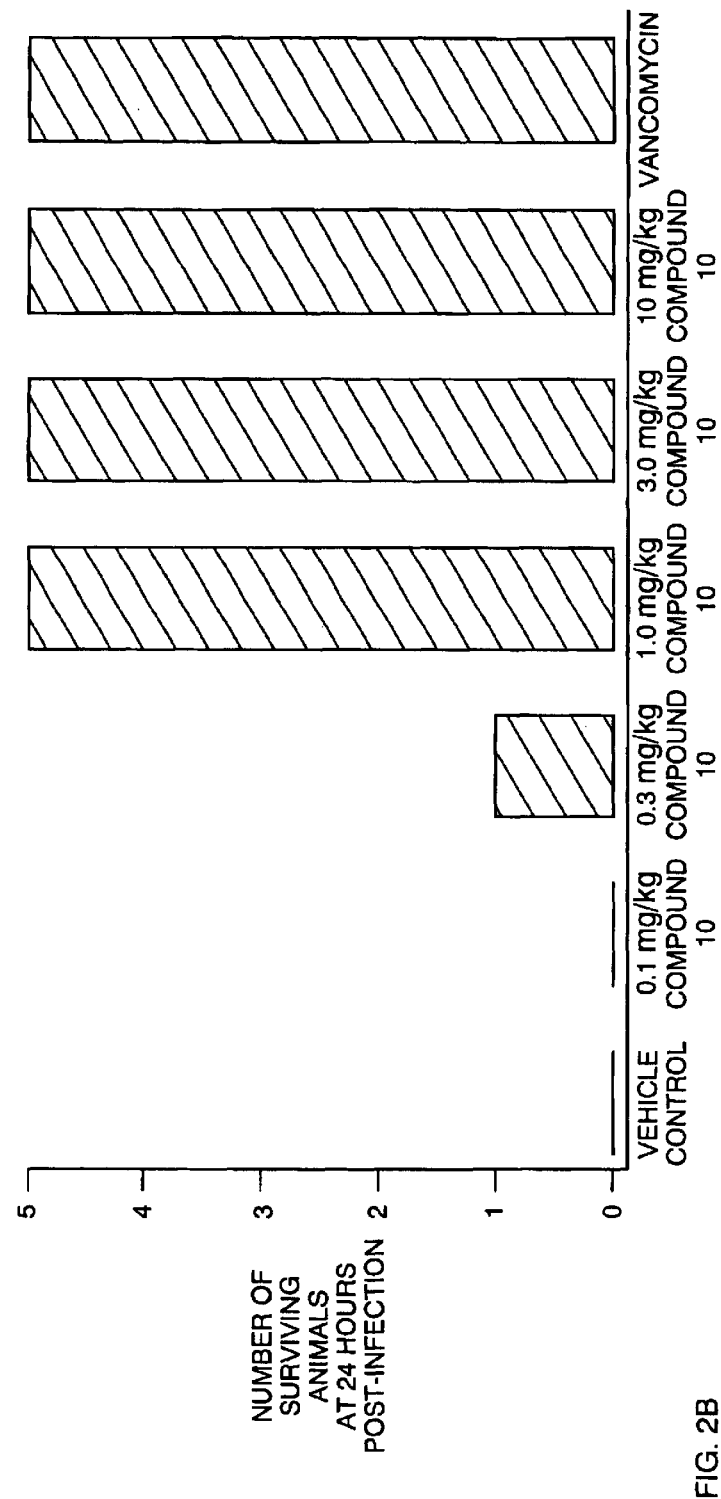
Figure 3A:
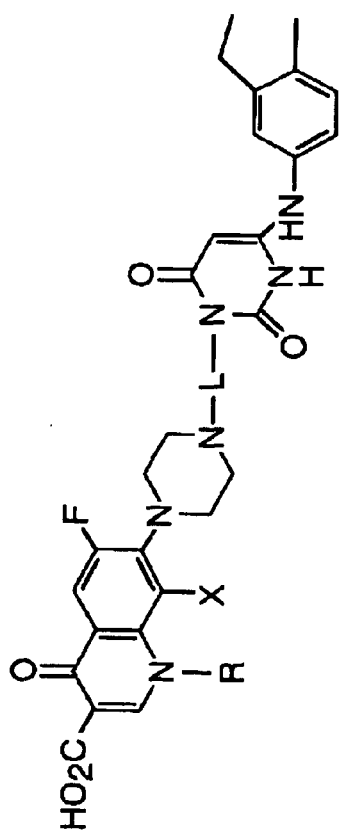
FIGS. 3A and 3B.
Figure 3B:
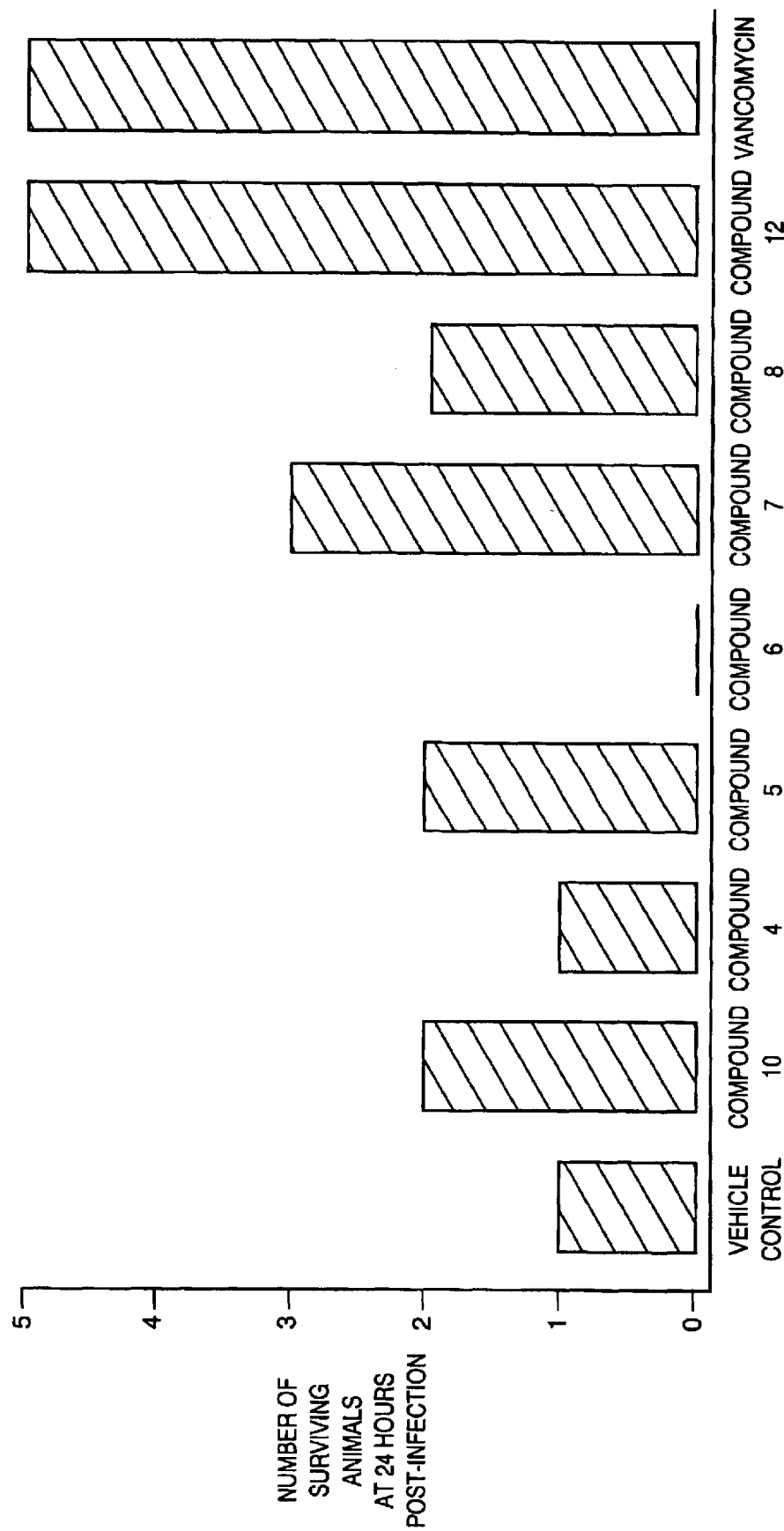

As shown in FIG. 1, protection was afforded all five infected mice that received compound Compound 2 intraperitoneally in the dosage range of 1–10 mg/kg body weight. Compound 10, which is the mesylate salt (i.e., the methanesulfonate salt) of Compound 2, provided protection in the same dosage range as Compound 2. As shown in FIG. 2, a dose of 0.3 mg of Compound 10 per kg body weight only protected one of five infected mice from death, whereas a dose of 1 mg/kg or higher provided complete protection. However, as shown in FIG. 3, depending on the compound tested, a dose of 0.5 mg/kg provided varying degrees of protection from infection with a *S. aureus* (Smith strain) bacteria.

Using the same basic procedure as described above, the in vivo efficacy of Compound 70 was also evaluated at various doses in mice infected with *S. aureaus* (Smith), MRSA 1094, *Enterococcus faecalis*, or vancomycin-resistant *Enterococcus faecalis* strain VRE 700802. As positive controls for antibiotic activity, mice infected with each strain of bacteria received vancomycin (30 or 100 mg/kg body weight) or ciprofloxacin (100 mg/kg body) at t=0. Negative controls were mice infected that received no treatment. Mucin was employed as an adjuvant to facilitate bacterial infection in mice, where indicated. Upon administration from distant parenteral sites (i.e., iv, sc, or im), Compound 70 provided a dose-related activity against intraperitoneal challenge with enterococci or staphylococci strains, including MRSA and VRE strains, with no overt toxicity at therapeutic doses (i.e., at doses providing levels of survival above negative (no treatment) control mice). The results of this study are shown in the table below.

In vivo Efficacy of Compound 70 in Mouse Models

| Organism | Dose (mg/kg) | Regimen | % Survival at 72 hours | Mean Survival Time (h) |
|---|---|---|---|---|
| *Staphylococcus aureus* | — | — | 15% (3/20) | N.D. |
| (Smith) | 3.125 | 1 (t = 0) | 0% (0/5) | N.D. |
| 10⁸ CFU/mouse | 6.25 | 1 (t = 0) | 0% (0/5) | N.D. |
|  | 12.5 | 1 (t = 0) | 40% (6/15) | N.D. |
|  | 25 | 1 (t = 0) | 100% (20/20)** | N.D. |
|  | 50 | 1 (t = 0) | 100% (10/10)** | N.D. |
| positive control | vancomycin | (30 mg/kg, t = 0) | 100% (20/20)** | N.D. |
| MRSA 1094 | — | — | 5%(1/20) | N.D. |
| 10⁷ CFU/mouse | 25 | 2 (t = 0, 2) | 0% (0/5) | N.D. |
| +5% Mucin | 50 | 2 (t = 0, 2) | 55% (11/20)* | N.D. |
|  | 75 | 2 (t = 0, 2) | 80% (4/5) | N.D. |
| positive control | vancomycin | (30 mg/kg, t = 0) | 95% (19/20)** | N.D. |
| *Enterococcus faecalis* | — | — | 13% (2/15) | N.D. |
| (ATCC 29212) | 25 | 1 (t = 0) | 40% (2/5) | N.D. |
| 3 × 10⁷ CFU/mouse | 50 | 1 (t = 0) | 60% (3/5) | N.D. |
| +5% Mucin | 75 | 1 (t = 0) | 80% (4/5) | N.D. |
|  | 25 | 2 (t = 0, 2) | 40% (2/5) | N.D. |
|  | 50 | 2 (t = 0, 2) | 80% (8/10)** | N.D. |
| positive control | vancomycin | (100 mg/kg, t = 0) | 100% (10/10)** | N.D. |
| VRE 700802 | — | — | 13% (2/15) | 17 |
| 3 × 10⁸ CFU/mouse | 100 | 1 (t = 0) | 0% (0/5) | 34 |
| +5% Mucin | 50 | 2 (t = 0, 2) | 10% (1/10) | 45 |
|  | 75 | 2 (t = 0, 2) | 0% (0/5) | 50 |
|  | 50 | 2 (t = 0, 3) | 0% (0/5) | 35 |
|  | 75 | 2 (t = 0, 3) | 40% (2/5) | 50 |
| positive control | ciprofloxacin | (100 mg/kg, t = 0) | 90% (9/10)** | N.D. |

* = p < 0.05,
** = p < 0.001,
N.D. = not determined

The results of the in vivo studies, above, indicated that the compounds tested were therapeutically effective as antibiotics against one or more clinically relevant Gram positive bacterial species.

All publications, patent applications, patents, and other documents cited herein are incorporated by reference in their entirety. In case of conflict, the present specification, including definitions, will control. In addition, the materials, methods, and examples are illustrative only and not intended to be limiting.

Other variations and embodiments of the invention described herein will now be apparent to those of ordinary skill in art without departing from the scope of the invention or the spirit of the claims below.

What is claimed is:

1. A compound having the formula:

P-L-T, wherein P is a segment that is a pyrimidine selected from the group consisting of a uracil substituted with an optionally substituted phenylamino or benzylamino at the 6-position and an isocytosine substituted with an optionally substituted phenylamino or benzylamino at the 6-position, wherein the phenylamino or benzylamino, if substituted, is substituted at the 3-position and/or the 4-position with a lower alkyl, a lower alkenyl, a lower alkynyl or halo; or positions 3 and 4 of the phenylamino or benzylamino are linked to form a fused 5 or 6-membered carbocyclic ring, which is saturated, unsaturated, or aromatic; and further wherein the pyrimidine selectively binds and inhibits bacterial DNA polymerase IIIC in the presence of a DNA template and is linked at the 3-position to linker segment L or directly to segment T, if L is absent; L is absent or is a linker segment comprising 1 to 10 atoms in contiguous linear connectivity that links P and T segments; and segment T is a pyridone that is linked to molecular segment P and that selectively inhibits a type II bacterial topoisomerase; and wherein the compound P-L-T inhibits DNA polymerase IIIC;

and pharmaceutically acceptable salts, and hydrates thereof.

2. The compound according to claim 1, wherein segment L, when present, is selected from the group consisting of tetramethylene, pentamethylene, heptamethylene, and ethoxyethylene.

3. The compound according to claim 1, wherein the pyridone of segment T that inhibits type II bacterial topoisomerase is a quinolone.

4. The compound according to claim 1, wherein the pyridone of segment T has a substituent attached to the pyridone and to the rest of the compound using points of attachment indicated on a substituent selected from the group consisting of:

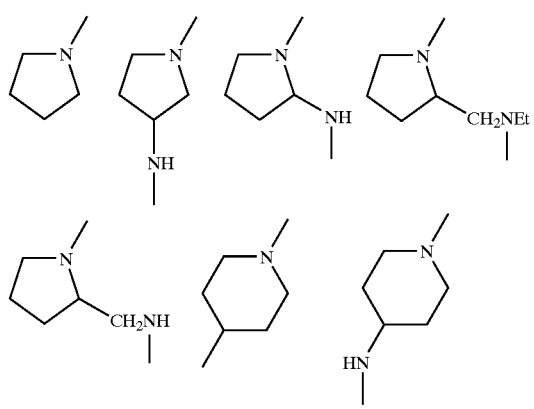

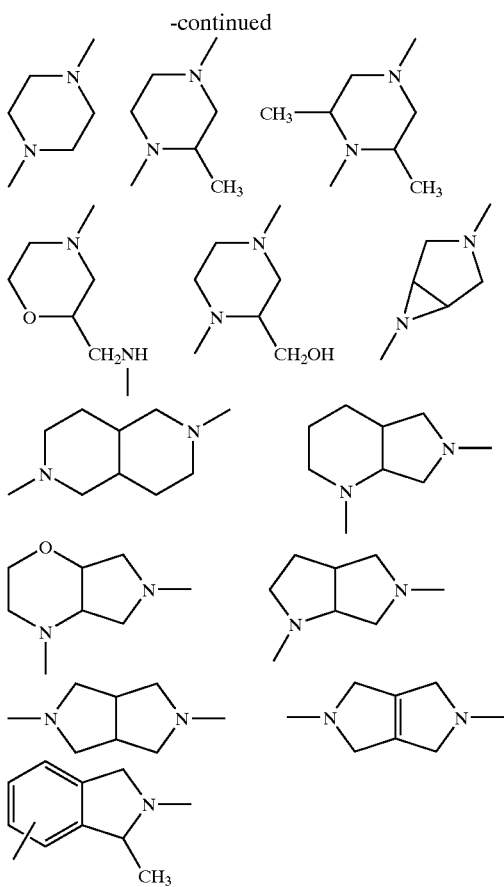

wherein Et is ethyl.

5. The compound according to claim 3, wherein the quinolone is a fluoroquinolone.

6. A compound selected from the group consisting of:

3-{4-[1-(1-ethyl-3-carboxy4-oxo-6-fluoro-7quinolyl)-4-piperazinyl]butyl}-6-(3-ethyl-4-methylanilino)uracil 3-{4-[1-(1-cyclopropyl-3-carboxy-4-oxo-6-fluoro-7-quinolyl)-4-piperazinyl]butyl}-6-(3-ethyl-4-methylanilino)uracil 3-{4-[1-(1-ethyl-3-carboxy-4-oxo-6-fluoro7quinolyl)-4-piperazinyl]butyl}-6-(3-ethyl-4-methylanilino)uracil hydrochloride 3-{4-[1-(1-ethyl-3-carboxy-4-oxo-6-fluoro-7-quinolyl)-4-piperazinyl]buty}-6-(3-ethyl-4-methylanilino)uracil methanesulfonate 3-{4-[1-(1-ethyl-3-carboxy-4-oxo-6-fluoro-8-chloro-7-quinolyl)-4-piperazinyl]butyl}-6-(3-ethyl-4-methylanilino)uracil 3-{4-[1-(1-ethyl-3-carboxy-4-oxo-6-fluoro-8-aza-7-quinolyl)-4-piperazinyl]butyl}-6-(3-ethyl-4-methylanilino)uracil 3-{4-[1-(1-ethyl-3-carboxy-4-oxo-6,8-difluoro-7-quinolyl)-4-piperazinyl]butyl}-6-(3-ethyl-4-methylanilino)uracil 3-{7-[1-(1-cyclopropyl-3-carboxy-4-oxo-6-fluoro-7-quinolyl)-4-piperazinyl]heptyl}-6-(3-ethyl-4-methylanilino)uracil 3-{4-[1-(1-cyclopropyl-3-carboxy-4-oxo-6-fluoro-7-quinolyl)-4-amino]butyl}-6-(3-ethyl-4-methylanilino)uracil 3-{4-[1-(1-cyclopropyl-3-carboxy-4-oxo-6-fluoro-7-quinolyl)-4-piperazinyl]butyl}-6-(3-ethyl-4-methylanilino)uracil methanesulfonate 3-{2-[1-(1-cyclopropyl-3-carboxy-4-oxo-6-fluoro-7-quinolyl)-4-piperazinyl]ethoxyethyl}-6-(3-ethyl-4-methylanilino)uracil 3-{4-[1-(1-{2,4-difluorophenyl}-3-carboxy-4-oxo-6-fluoro-7-quinolyl)-4-piperazinyl]butyl}-6-(3-ethyl-4-methylanilino)uracil 3-{4-[1-(1-{2-hydroxyethyl}-3-carboxy-4-oxo-6-fluoro-7-quinolyl)-4-piperazinyl]butyl}-6-(3-ethyl-4-methylanilino)uracil 3-{4-[1-(1-{4-fluorophenyl}-3-carboxy-4-oxo-6-fluoro-7-quinolyl)-4-piperazinyl]butyl}-6-(3-ethyl-4-methylanilino)uracil 3-{5-[1-(1-cyclopropyl-3-carboxy-4-oxo-6-fluoro-7-quinolyl)-4-piperazinyl]pentyl}-6-(3-ethyl-4-methylanilino)uracil 3-{5-[1-(1-ethyl-3-carboxy-4-oxo-6-fluoro-8-aza-7-quinolyl)-4-piperazinyl]pentyl}-6-(3-ethyl-4-methylanilino)uracil 3-{4-[1-(1-tert-butyl-3-carboxy-4-oxo-6-fluoro-7-quinolyl)-4-piperazinyl]butyl}-6-(3-ethyl-4-methylanilino)uracil 3-{4-[1-(1-{2,4-difluorophenyl}-3-carboxyl-4-oxo-6-fluoro-8-methoxy-7-quinolyl)-4-piperazinyl]butyl}-6-(3-ethyl-4methylanilino)uracil 3-{4-[1-(1-cyclopropyl-3-carboxy-4-oxo-6-fluoro-7-quinolyl)-4-piperazinyl]butyl}-6-(3-ethyl-4-methylanilino)isocytosine 3-{4-[1-(1-cyclopropyl-3-carboxy-4-oxo-6-fluoro-7-quinolyl)-4-piperazinyl]butyl}-6-(3-ethyl-4-methylanilino)uracil hydrochloride 3-{4-[1-(1-{ethyl}-3-carboxy-4-oxo-6-fluoro-8-methoxy-7-quinolyl)-4-piperazinyl]butyl}-6-(3-ethyl-4-methylanilino)uracil 3-{4-[1-(1-{cyclopropyl}-3-carboxy-4-oxo-6-fluoro-8-methoxy-7-quinolyl)-4-piperazinyl]butyl}-6-(3-ethyl-4-methylanilino)uracil 3-{4-[3-(1-ethyl-3-carboxy-4-oxo-6-fluoro-7-quinolyl)aminomethyl-1-pyrrolidinyl]butyl}-6-(3-ethyl-4-methylanilino)uracil 3-{4-[3-(1-cyclopropyl-3-carboxy-4-oxo-6-fluoro-7-quinolyl)aminomethyl-1-pyrrolidinyl]butyl}-6-(3-ethyl-4-methylanilino)uracil 3-{4-[3-(1-(2,4-difluorophenyl)-3-carboxy-4-oxo-6-fluoro-7-quinolyl)aminomethyl-1-pyrrolidinyl]butyl}-6-(3-ethyl-4-methylanilino)uracil 3-{4-[1-(1-ethyl-3-carboxy-4-oxo-6-pyridyl)-4-piperazinyl]butyl}-6-(3-ethyl-4-methylanilino)uracil 3-{4-[1-(1-cyclopropyl-3-carboxy-4-oxo-6-pyridyl)-4-piperazinyl]butyl}-6-(3-ethyl-4-methylanilino)uracil 3-{4-[1-(1-{2,4-difluorophenyl}-3-carboxy-4-oxo-6-pyridyl)-4-piperazinyl]butyl}-6-(3-ethyl-4-methylanilino)uracil 3-{4-[3-(1-ethyl-3-carboxy-4-oxo-6-fluoro-7-quinolyl)aminomethyl-1-pyrrolidinyl]butyl}-6-(3-ethyl-4-methylanilino)isocytosine 3-{4-[1-(1-cyclopropyl-3-carboxy-4-oxo-6-fluoro-7-quinolyl)aminomethyl-1-pyrrolidinyl]butyl}-6-(3-ethyl-4-methylanilino)isocytosine 3-{4-[1-(1-{2,4-difluorophenyl}-3-carboxy-4-oxo-6-fluoro-7-quinolyl)aminomethyl-1-pyrrolidinyl]butyl}-6-(3-ethyl4-methylanilino)isocytosine 3-{4-[1-(1-ethyl-3-carboxy-4-oxo-6-pyridyl)-4-piperazinyl]butyl}-6-(3-ethyl-4-methylanilino)isocytosine 3-{4-[1-(1-cyclopropyl-3-carboxy-4-oxo-6-pyridyl)-4-piperazinyl]butyl}-6-(3-ethyl-4-methylanilino)isocytosine 3-{4-[1-(1-{2,4-difluorophenyl}-3-carboxy-4-oxo-6-pyridyl)-4-piperazinyl]butyl}-6-(3-ethyl-4-methylanilino)isocytosine 3-{5-[1-(1-ethyl-3-carboxy-4-oxo-6-fluoro-8-methoxy-7-quinolyl)-4-pipcrazinyl]pentyl}-6-(3-ethyl-4-methylanilino)uracil 3-{5-[1-(1-{cyclopropyl}-3-carboxy-4-oxo-6-fluoro-8-methoxy-7-quinolyl)-4-piperazinyl]pentyl}-6-(3-ethyl-4-methylanilino)uracil 3-{5-[3-(1-ethyl-3-carboxy-4-oxo-6-fluoro-7-quinolyl)aminomethyl-1-pyrrolidinyl]pentyl}-6-(3-ethyl-4-methylanilino)uracil 3-{5-[3-(1-cyclopropyl-3-carboxy-4-oxo-6-fluoro-7-quinolyl)aminomethyl-1-pyrrolidinyl]pentyl}-6-(3-ethyl-4-methylanilino)uracil 3-{5-[3-(1-(2,4-difluorophenyl)-3-carboxy-4-oxo-6-fluoro-7-quinolyl)aminomethyl-1-pyrrolidinyl]pentyl}-6-(3-ethyl-4-methylanilino)uracil 3-{5-[1-(1-ethyl-3-carboxy-4-oxo-6-pyridyl)-4-piperazinyl]pentyl}-6-(3-ethyl-4-methylanilino)uracil 3-{5-[1-(1-cyclopropyl-3-carboxy-4-oxo-6-pyridyl)-4-pipcrazinyl]pentyl}-6-(3-ethyl-4-methylanilino)uracil 3-{5-[1-(1-{2,4-difluorophenyl}-3-carboxy-4-oxo-6-pyridyl)-4-piperazinyl]pentyl}-6-(3-ethyl-4-methylanilino)uracil 3-{5-[3-(1-ethyl-3-carboxy-4-oxo-6-fluoro-7-quinolyl)aminomethyl-1-pyrrolidinyl]pentyl}-6-(3-ethyl-4-methylanilino)isocytosine 3-{5-[1-(1-cyclopropyl-3-carboxy-4-oxo-6-fluoro-7-quinolyl)aminomethyl-1-pyrrolidinyl]pentyl}-6-(3-ethyl-4-methylanilino)isocytosine 3-{5-[1-(1-{2,4-difluorophenyl}-3-carboxy-4-oxo-6-fluoro-7-quinolyl)aminomethyl-1-pyrrolidinyl]pentyl}-6-(3-ethyl-4-methylanilino)isocytosine 3-{5-[1-(1-ethyl-3-carboxy-4-oxo-6-pyridyl)-4-piperazinyl]pentyl}-6-(3-ethyl-4-methylanilino)isocytosine 3-{5-[1-(1-cyclopropyl-3-carboxy-4-oxo-6-pyridyl)-4-piperazinyl]pentyl}-6-(3-ethyl-4-methylanilino)isocytosine 3-{5-[1-(1-(2,4-difluorophenyl)-3-carboxy-4-oxo-6-pyridyl)-4-piperazinyl]pentyl}-6-(3-ethyl-4-methylanilino)isocytosine 3-{4-[1-(1-cyclopropyl-3-carboxy-4-oxo-6-fluoro-7-quinolyl)-4-piperazinyl]butyl}-6-(3-chloro-4-methylanilino)uracil 3-{4-[1-(1-cyclopropyl-3-carboxy-4-oxo-6-fluoro-7-quinolyl)-4-piperazinyl]butyl}-6-(3,4-dimethylanilino)uracil 3-{4-[-(1-cyclopropyl-3-carboxy-4-oxo-6-fluoro-7-quinolyl)-4-piperazinyl]butyl}-6-(3-ethylanilino)uracil 3-{4-[1-(1-cyclopropyl-3-carboxy-4-oxo-6-fluoro-7-quinolyl)-4-piperazinyl]butyl}-6-(5-indanylamino)uracil 3-{4-[1-(1-cyclopropyl-3-carboxy-4-oxo-6-fluoro-7-quinolyl)-4-piperazinyl]butyl}-6-(3,4-dichlorobenzylamino)uracil 3-{4-[1-(1-cyclopropyl-3-carboxy-4-oxo-6-fluoro-7-quinolyl)-4-(2-methylpiperazinyl)]butyl}-6-(3-ethyl-4-methylanilino)uracil 3-{4-[1-(1-cyclopropyl-3-carboxy-4-oxo-6,8-difluoro-7-quinolyl)-4-(3-methylpiperazinyl)]butyl}-6-(3ethyl-4-methylanilino)uracil (S)-3-{4-[1-(1-cyclopropyl-3-carboxy-4-oxo-6,8-difluoro-7-quinolyl)-4-(3-methylpiperazinyl)]butyl}-6-(3-ethyl-4-methylanilino)uracil (R)-3-{4-[1-(1-cyclopropyl-3-carboxy-4-oxo-6,8-difluoro-7-quinolyl)-4(3methylpiperazinyl)]butyl}-6-(3-ethyl-4-methylanilino)uracil 3-{4-[1-(1-cyclopropyl-3-carboxy-4-oxo-6-fluoro-8-methoxy-7-quinolyl)-4-(3-methylpiperazinyl)]butyl}-6-(3-ethyl-4-methylanilino)uracil 3-{4-[1-(1-{2,4-difluorophenyl}-3-carboxy-4-oxo-6-fluoro-7-quinolyl)-4-(3-methyl)piperazinyl]butyl}-6-(3-ethyl-4-methylanilino)uracil 3-{4-[1-(1-ethyl-3-carboxy-4-oxo-6,8-diaza-7-quinolyl)-4-piperazinyl]butyl}-6-(3-ethyl-4-methylanilino)uracil 3-{5-[1-(1-ethyl-3-carboxy-4-oxo-6-fluoro-7-quinolyl)-3-(1,3-diazabicyclononyl)]pentyl}-6-(3-ethyl-4-methylanilino)uracil 3-{5-[1-(1-cyclopropyl-3-carboxy-4-oxo-6-fluoro-7-quinolyl)-3-(1,3-diazabicyclooctyl)]pentyl}-6-(3-ethyl-4-methylanilino)uracil 3-{5-[1(1-cyclopropyl-3-carboxy-4-oxo-6-fluoro-7-quinolyl)-3-(1,3-diazabicyclononyl)]pentyl}-6-(3-ethyl-4-methylanilino)uracil 3-{5-[1-(1-cyclopropyl-3-carboxy-4-oxo-6-fluoro-7-quinolyl)-3-(pyrrolidinylamino)]pentyl}-6-(3-ethyl-4-methylanilino)uracil 3-{5-[1-(1-cyclopropyl-3-carboxy-4-oxo-6-fluoro-7-quinolyl)-3-(5-oxa-1,3-diazabicyclonony)]pentyl}-6-(3-ethyl-4-methylanilino)uracil 3-{5-[1-(1-ethyl-3-carboxy-4-oxo-6,8-difluoro-7-quinolyl)-3-(5-oxa-1,3-diazabicyclononyl)]pentyl}-6-(3-ethyl-4-methylanilino)uracil 3-{5-[1-(1-cyclopropyl-3-carboxy-4-oxo-6-fluoro-7-quinolyl)-4-(1,4-diazabicyclooctyl)]pentyl}-6-(3-ethyl-4-methylanilino)uracil 3-{4-[1-(1-cyclopropyl-3-carboxy-4-oxo-6-fluoro-7-quinolyl)-3-(5-oxa-1,3-diazabicyclononyl)]butyl}-6-(3-ethyl-4-methylanilino)uracil 3-{5-[1-(1-ethyl-3-carboxy-4-oxo-6,8-difluoro-7-quinolyl)-3-(1,3-diazabicyclononyl)]pentyl}-6-(3-ethyl-4-methylanilino)uracil 3-{4-[1-(1-{2,4-difluorophenyl}-3-carboxy-4-oxo-6-fluoro-7-quinolyl)-4-(3methylpiperazinyl)]butyl}-6-(3-ethyl-4-methylanilino)uracil (R)-3-{4-[1-(1-{2,4-difluorophenyl}-3-carboxy4-oxo-6-fluoro-7-quinolyl)-4-(3-methylpiperazinyl)]butyl}-6-(3-ethyl-4-methylanilino)uracil 3-{4-[1-(1-cyclopropyl-3-carboxy-4-oxo-6,8-difluoro-7-quinolyl)-4-(3-hydroxymethylpiperazinyl)]butyl}-6-(3ethyl-4-methylanilino)uracil 3-{4-[1-(1-cyclopropyl-3-carboxy-4-oxo-6,8-difluoro-7-quinolyl)-4-(3-methylpiperazinyl)]butyl}-6-(5-indanylamino)uracil 3-{4-[1-(1-cyclopropyl-3-carboxy-4-oxo-6,8-difluoro-7-quinolyl)-4-(3-methylpiperazinyl)]butyl}-6-(3-chloro-4-methylanilino)uracil 3-{4-[1-(1-cyclopropyl-3-carboxy-4-oxo-6,8-difluoro-7-quinolyl)-4-(3-methylpiperazinyl)]butyl}-6-(3,4-dimethylanilino)uracil (R)-3-{4-[1-(1-cyclopropyl-3-carboxy-4-oxo-6-fluoro-7-quinolyl)-4-(3-methylpiperazinyl)]butyl}-6-(3-ethyl-4-methylanilino)uracil (R)-3-{4-[1-(1-cyclopropyl-3-carboxy-4-oxo-6-fluoro-7-quinolyl)-4-(3-methylpiperazinyl)]butyl}-6-(3,4-dimethylanilino)uracil (S)-3-{4-[1-(1-cyclopropyl-3-carboxy-4-oxo-6-fluoro-7-quinolyl)-4-(3-methylpiperazinyl)]butyl}-6-(3,4-dimethylanilino)uracil (R)-3-{4-[1-(1cyclopropyl-3-carboxy-4-oxo-6,8-difluoro-7-quinolyl)-4-(3-methylpiperazinyl)]butyl}-6-(3,4-dimethylanilino)uracil (S)-3-{4-[1-(1-cyclopropyl-3-carboxy-4-oxo-6,8-difluoro-7-quinolyl)-4-(3-methylpiperazinyl)]butyl}-6-(3,4-dimethylanilino)uracil (S)-3-{4-[1-(1-cyclopropyl-3-carboxy-4-oxo-6-fluoro-7-quinolyl)-4-(3-methylpiperazinyl)]butyl}-6-(3-ethyl-4-methylanilino)uracil 3-{4-[1-(1-cyclopropyl-3-carboxy-4-oxo-6,8-difluoro-7-quinolyl)-4-(piperazinyl)]butyl}-6-(3,4-dimethylanilino)uracil 3-{4-[1-(1cyclopropyl-3-carboxy-4-oxo6-fluoro-8-methoxy)-7-quinolyl)-4-(3-methylpiperazinyl)]butyl}-6-(3-ethyl-4-methylanilino)uracil 3-{4-[1-(1-cyclopropyl-3-carboxy-4-oxo-6-fluoro-8-methoxy)-7-quinolyl)-4-(3-methylpiperazinyl)]butyl}-6-(3,4-dimethylanilino)uracil 3{4-[1-(1-cyclopropyl-3-carboxy4-oxo-6,8-difluoro-7-quinolyl)-4-(3-carboxypiperazinyl)]butyl}-6-(3-ethyl-4-methylanilino)uracil 3-{4-[1-(1-cyclopropyl-3-carboxy-4-oxo-7-quinolyl)-4-piperazinyl]butyl}-6-(3-ethyl-4-methylanilino)uracil 3-{4-[1-(1-allyl-3-carboxy-4-oxo-7-quinolyl)-4-piperazinyl]butyl}-6-(3-ethyl-4-methylanilino)uracil (R)-3-{4-[1-(1-cyclopropyl-3-carboxy-4-oxo-7-quinolyl-8-difluoromethoxy)-4-(3-methylpiperazinyl)]butyl}-6-(3-ethyl-4-methylanilino)uracil (R)-3-(4-[2-(1-cyclopropyl-3-carboxy-4-oxo-7-quinolyl-8-difluoromethoxy)-2,3-dihydro-1-methyl-isoindol-5-yl)]butyl}-6-(3-ethyl-4-methylanilino)uracil 3-{4-[1-(1-ethyl-3-carboxy4-oxo-6,8-diaza-7-quinolyl)-4-(3methyl piperazinyl)]butyl}-6-(3-ethyl-4-methylanilino)uracil.

7. A compound selected from the group consisting of:

3-{4-[1-(1cyclopropyl-3-ethoxycarbonyl-4-oxo-6-fluoro-7-quinolyl)-4-piperazinyl]butyl)}6-(3-ethyl-4-methylanilino)uracil 3-{2-[1-(1cyclopropyl-3-benzyloxycarbonyl-4-oxo-6-fluoro-7-quinolyl)-4-piperazinyl]ethoxyethyl}-6-(3-ethyl-4-methylanilino)uracil 3-{4-[1-(1cyclopropyl-3-ethoxycarbonyl-4-oxo-6-fluoro-7-quinolyl)-4-piperazinyl]butyl}-6-anilinouracil 3-{4-[1-(1-{2,4-difluorophenyl}-3-ethoxycarbonyl-4-oxo-6-fluoro-7-quinolyl)-4-piperaziny]butyl}-6-(3-ethyl-4-methylanilino)uracil 3-{4-[1-(1-{2-hydroxyethyl}3-ethoxycarbonyl-4-oxo-6,8-difluoro-7-quinolyl)-4-piperazinyl]butyl}-6-(3-ethyl-4-methylanilino)uracil and 3-{4-[1-(1-{4-fluorophenyl}-3-ethoxycarbonyl-4-oxo-6-fluoro-7-quinolyl)-4-piperazinyl]butyl}-6-(3ethyl-4-methylanilino)uracil.

8. A pharmaceutical composition comprising a compound according to claim 1 and a pharmaceutically acceptable carrier.

9. The pharmaceutical composition according to claim 8, further comprising an additional compound selected from the group consisting of an antibiotic, an antiviral compound, anti-cancer compound, a vitamin, a trace metal, and combinations thereof.

10. A method of therapeutically treating a bacterial disease in a patient in need of treatment thereof comprising administering to the patient a pharmaceutical composition according to claim 8.

11. A method of treating a patient to prevent a bacterial disease comprising administering to the patient a pharmaceutical composition according to claim 8.

12. A method of inhibiting or reducing the activity of DNA polymerase IIIC in a patient in need of treatment thereof comprising administering to the patient a pharmaceutical composition according to claim 8.

13. A method of inhibiting or reducing the activity of bacterial type II topoisomerase in a patient in need of treatment thereof comprising administering to the patient a pharmaceutical composition according to claim 8.

14. A method of determining the antibiotic resistance profile of a bacterial species of interest comprising testing the ability of cells of the bacterial species of interest to grow on a growth medium supplemented with a compound according to claim 1.

15. A kit comprising a compound according to claim 1 and instructions describing use of the compound in treating a bacterial disease.

16. A kit comprising a compound according to claim 1 and instructions describing use of the compound for inhibiting a DNA polymerase IIIC and/or type II topoisomerase.

* * * * *